(12) United States Patent
Tiwari et al.

(10) Patent No.: US 11,986,467 B2
(45) Date of Patent: May 21, 2024

(54) MATERIALS AND METHODS USEFUL TO INDUCE CANCER CELL DEATH VIA METHUOSIS OR AUTOPHAGY OR A COMBINATION THEREOF

(71) Applicant: The University of Toledo, Toledo, OH (US)

(72) Inventors: Amit K. Tiwari, Toledo, OH (US); Chandrabose Karthikeyan, Toledo, OH (US); Haneen A. Amawi, Toledo, OH (US); Paul W. Erhardt, Toledo, OH (US); Piyush Trivedi, Toledo, OH (US)

(73) Assignee: The University of Toledo, Toledo, OH (US)

( * ) Notice: Subject to any disclaimer, the term of this patent is extended or adjusted under 35 U.S.C. 154(b) by 0 days.

(21) Appl. No.: 17/861,946

(22) Filed: Jul. 11, 2022

(65) Prior Publication Data

US 2022/0370430 A1   Nov. 24, 2022

Related U.S. Application Data

(62) Division of application No. 16/650,986, filed as application No. PCT/US2018/052809 on Sep. 26, 2018, now Pat. No. 11,406,626.

(60) Provisional application No. 62/564,018, filed on Sep. 27, 2017.

(51) Int. Cl.
*A61K 31/4439* (2006.01)
*A61K 31/122* (2006.01)
*C07D 401/14* (2006.01)
*C07D 513/04* (2006.01)

(52) U.S. Cl.
CPC ........ *A61K 31/4439* (2013.01); *A61K 31/122* (2013.01); *C07D 401/14* (2013.01); *C07D 513/04* (2013.01)

(58) Field of Classification Search
CPC .............. A61K 31/4439; A61K 31/122; C07D 401/14; C07D 513/04
USPC ........................................................ 514/338
See application file for complete search history.

(56) References Cited

PUBLICATIONS

Kumar et al. Chemical Biology & Drug Design (2011), 77(3), 182-188.*

* cited by examiner

*Primary Examiner* — Kahsay Habte
(74) *Attorney, Agent, or Firm* — MacMillan, Sobanski & Todd, LLC

(57) ABSTRACT

Compounds, compositions, and methods useful for inducing cancer cell death via methuosis, autophagy, or a combination thereof, are described. The compounds have a 4-pyridyl group linked by a heterocyclic group to an aryl, heteroaryl, aralkyl, or heteroaryl alkyl.

13 Claims, 57 Drawing Sheets
(26 of 57 Drawing Sheet(s) Filed in Color)

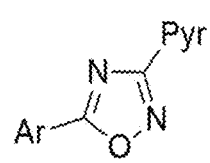
XVI
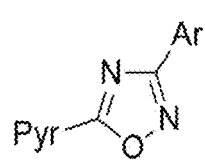
XVII
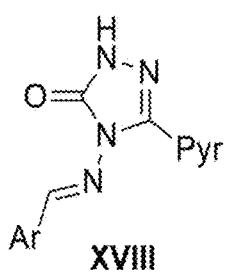
XVIII
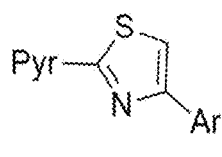
XIX
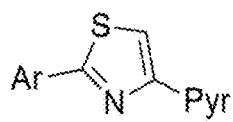
XX
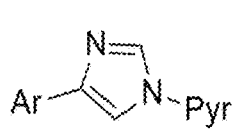
XXI
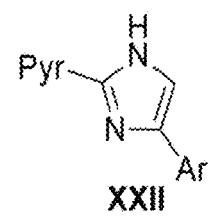
XXII
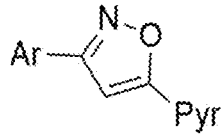
XXIII
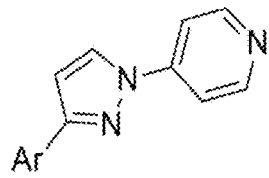
XXIV
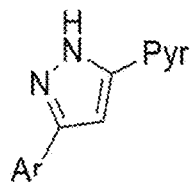
XXV
FIG. 1 Cont.

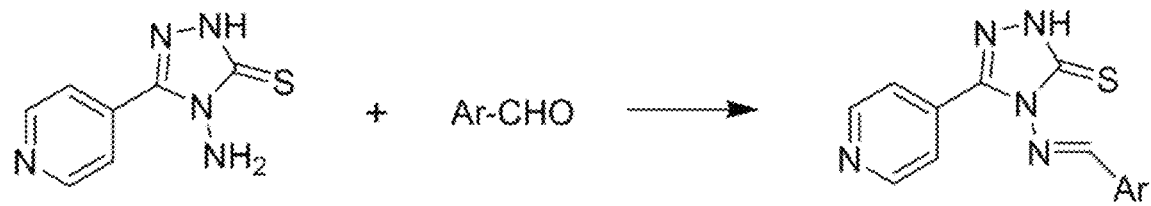
FIG. 2 – Scheme 1
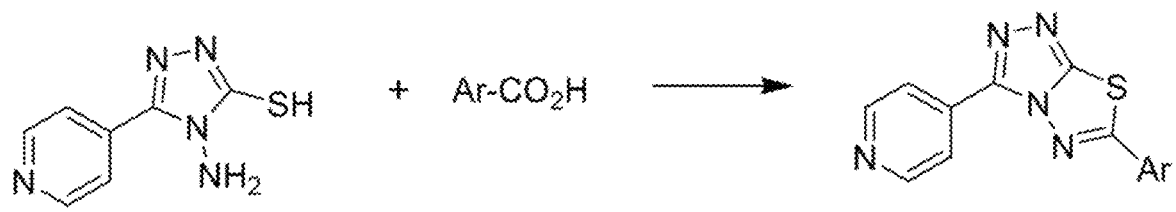
FIG. 3 – Scheme 2
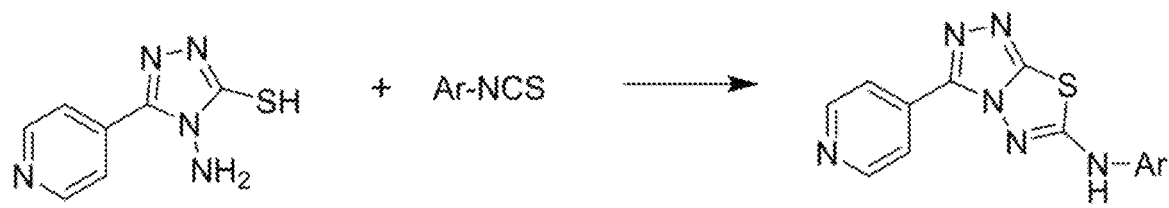
FIG. 4 – Scheme 3
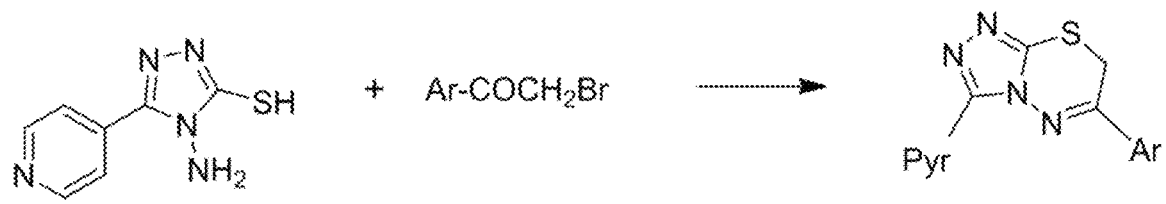
FIG. 5 – Scheme 4

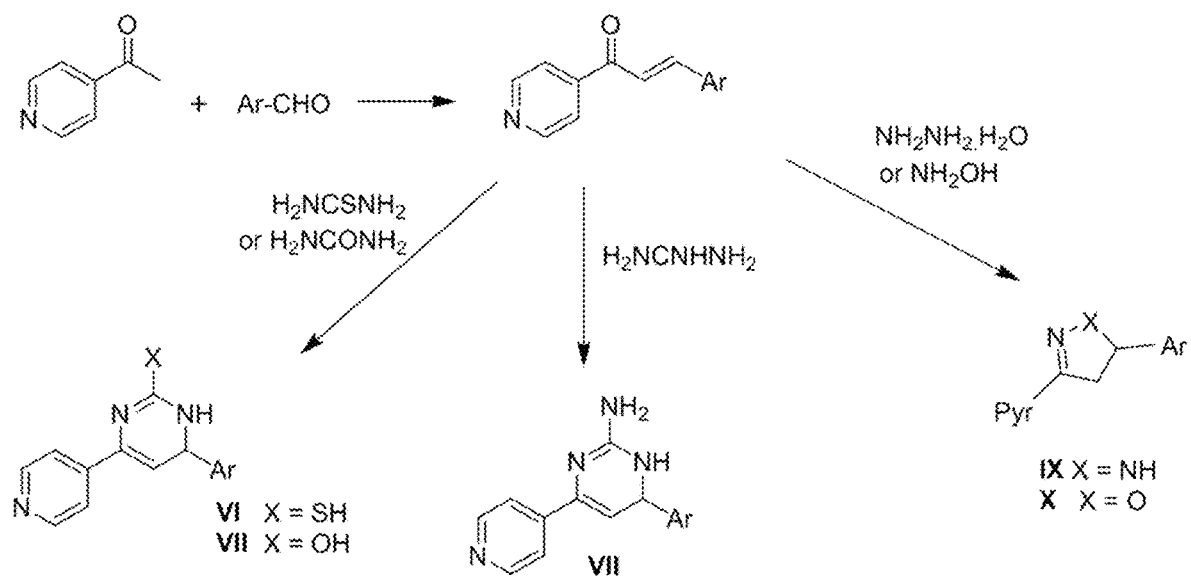
FIG. 6 – Scheme 5
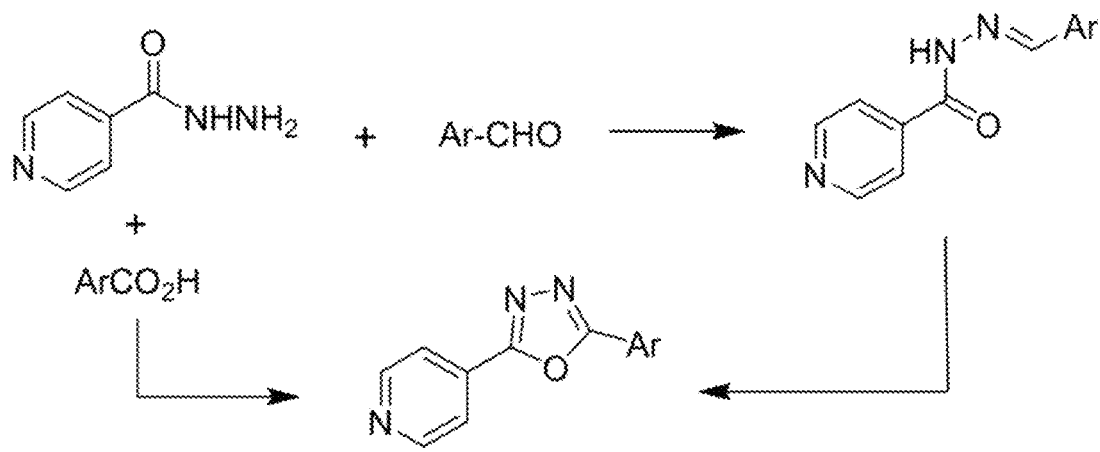
FIG. 7 – Scheme 6

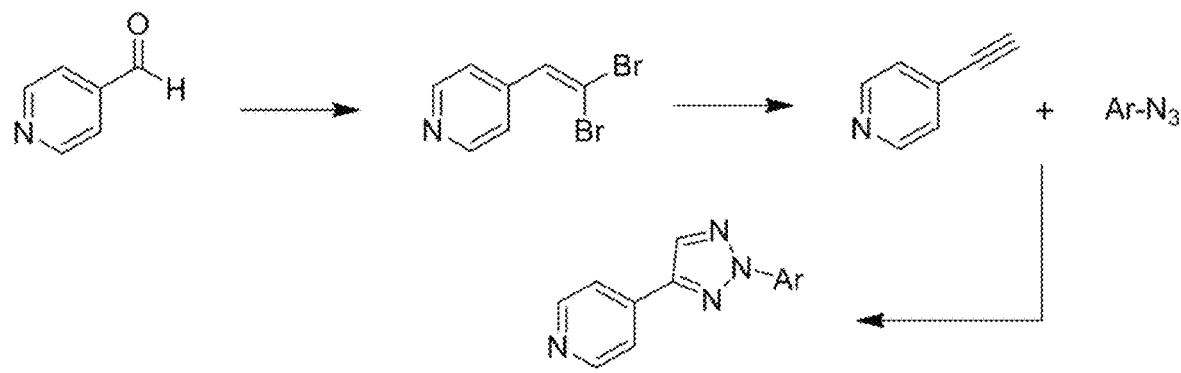
FIG. 8 – Scheme 7
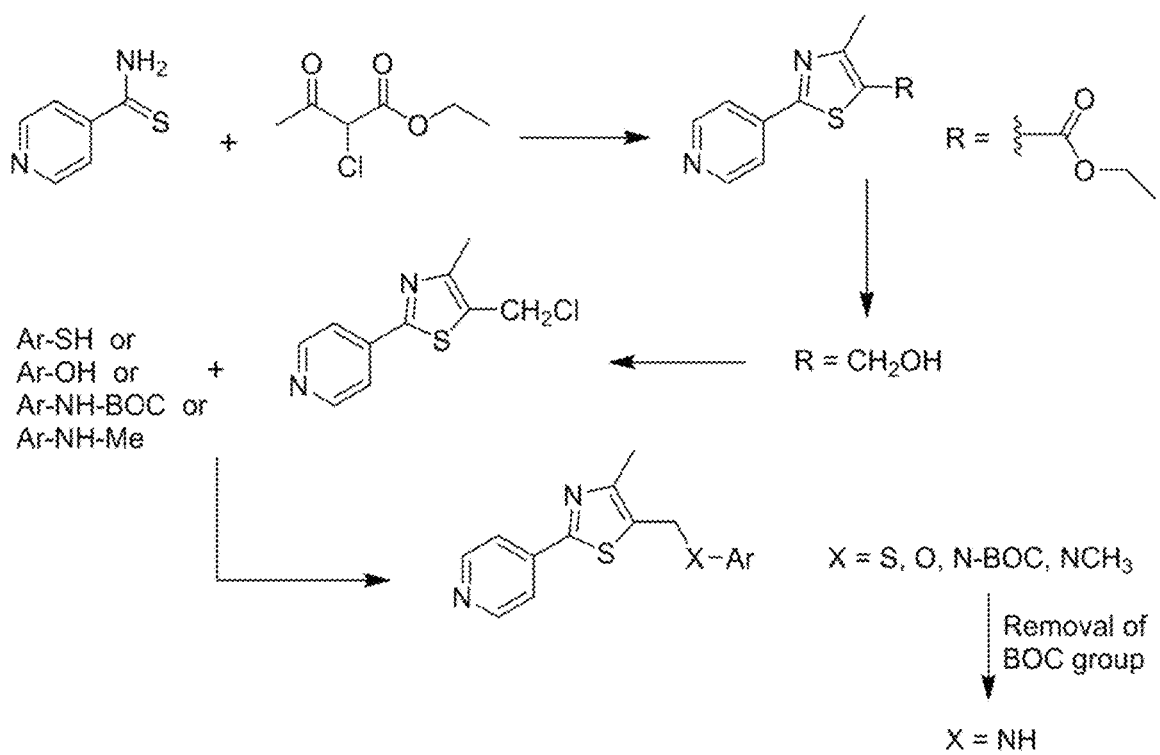
FIG. 9 – Scheme 8

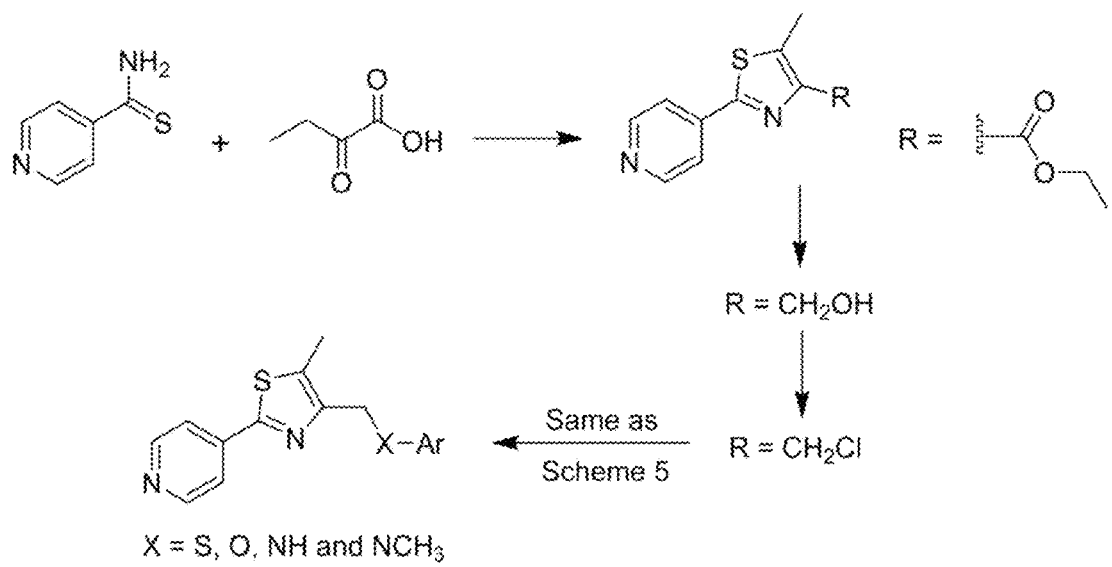
FIG. 10 – Scheme 9
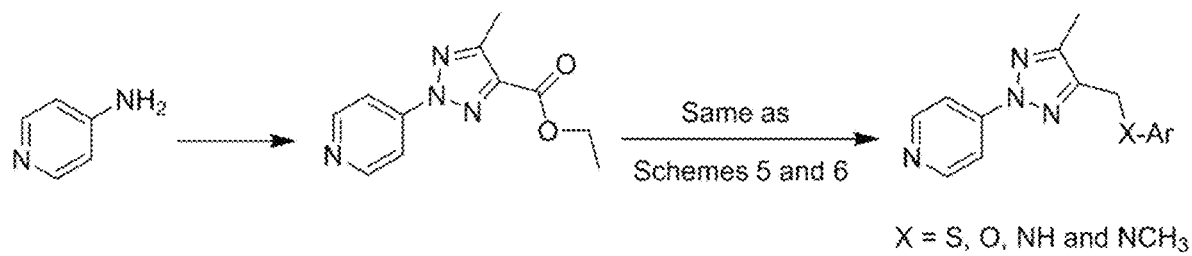
FIG. 11 – Scheme 10

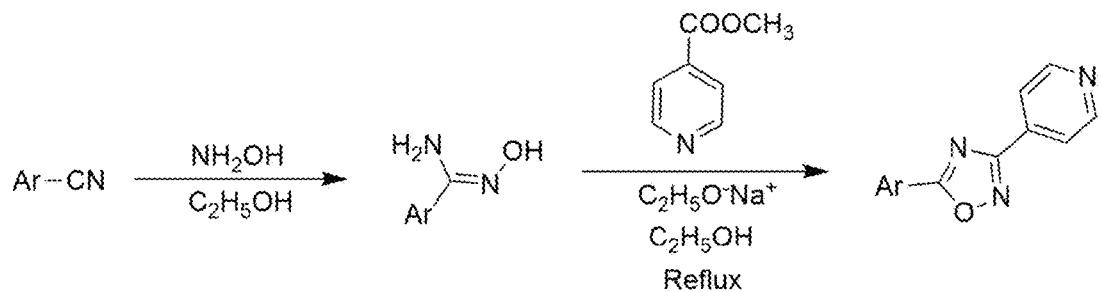
FIG. 12 – Scheme 11
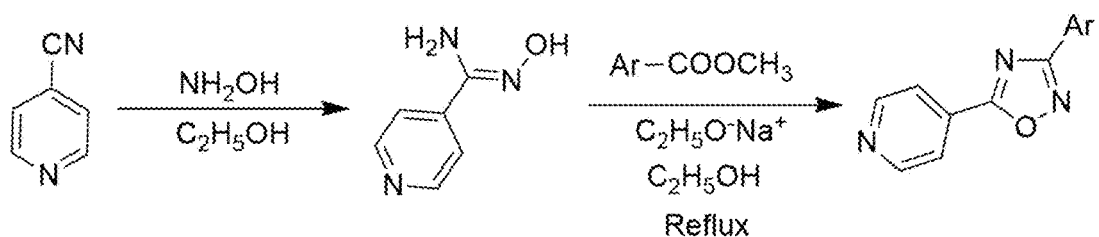
FIG. 13 – Scheme 12
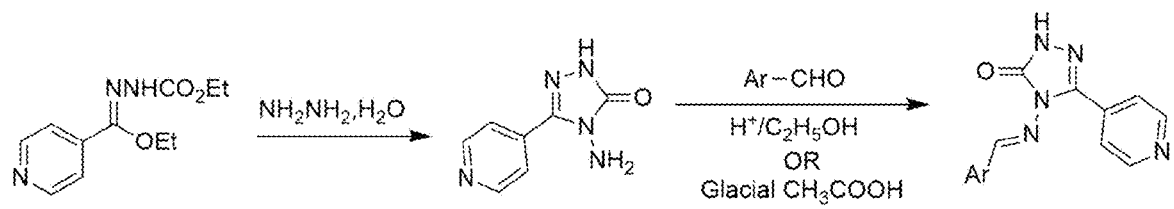
FIG. 14 – Scheme 13

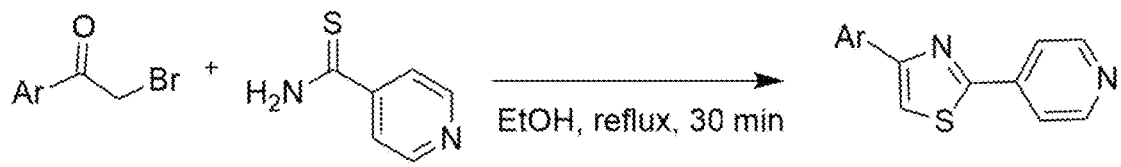
FIG. 15 – Scheme 14
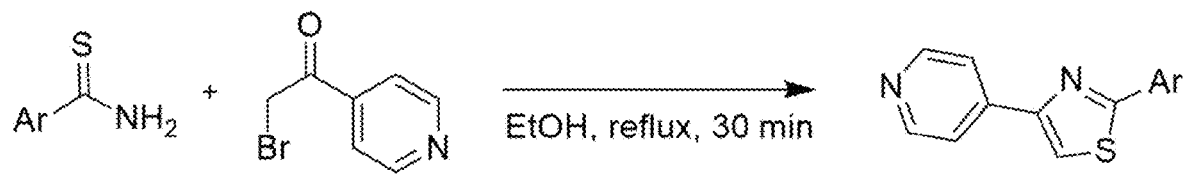
FIG. 16 – Scheme 15
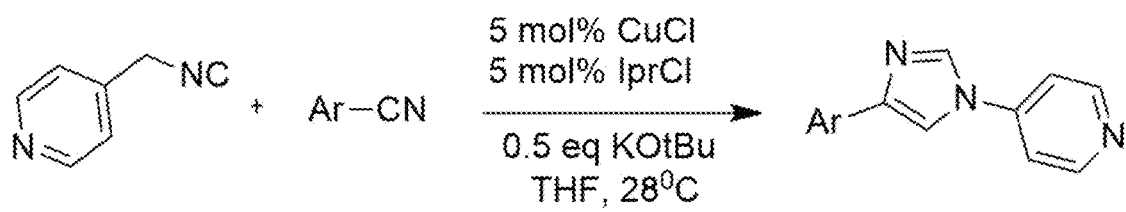
FIG. 17 – Scheme 16
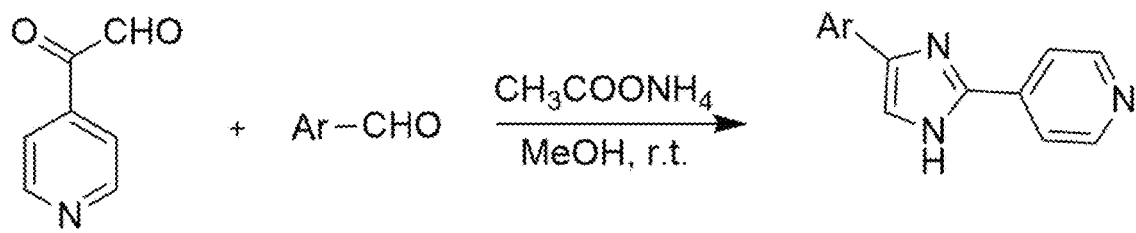
FIG. 18 – Scheme 17

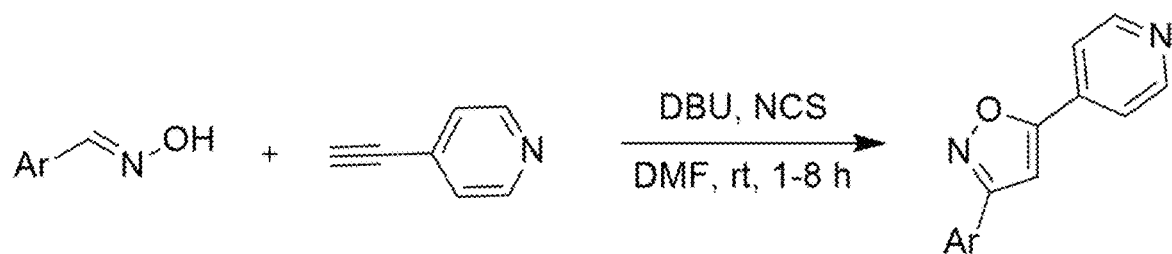
FIG. 19 – Scheme 18
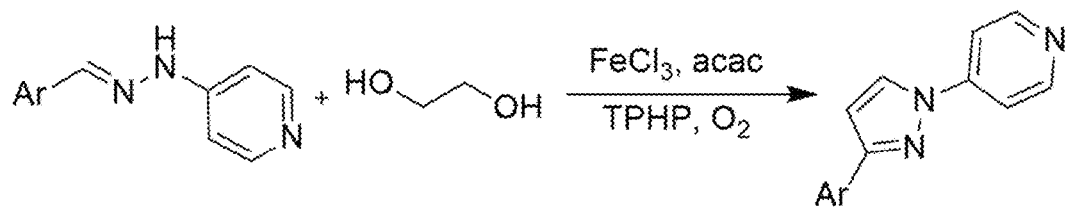
FIG. 20 – Scheme 19
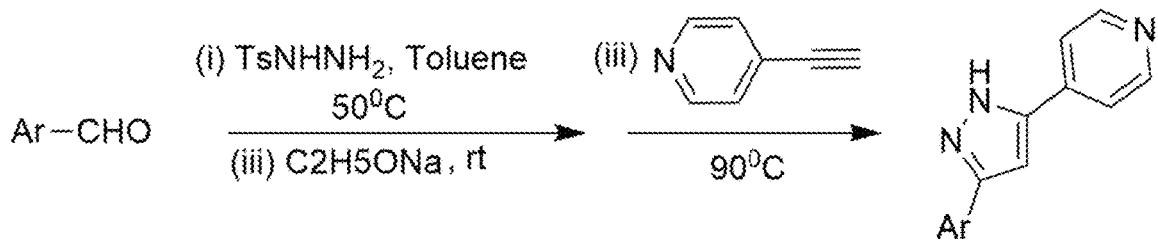
FIG. 21 – Scheme 20

Scheme 21
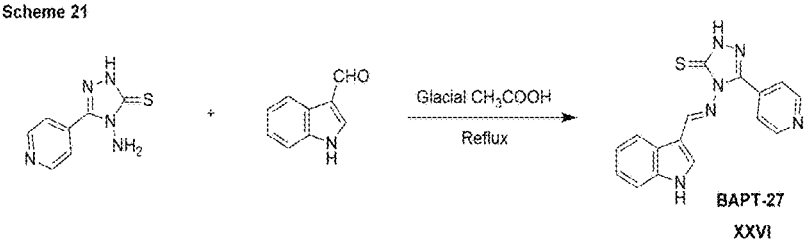
BAPT-27
XXVI
Scheme 22
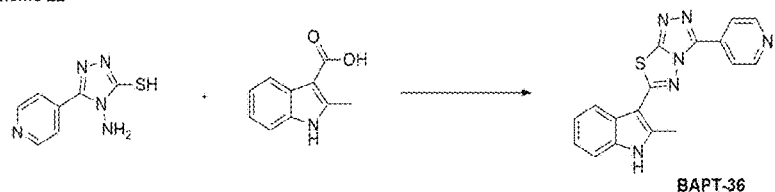
BAPT-36
Scheme 23
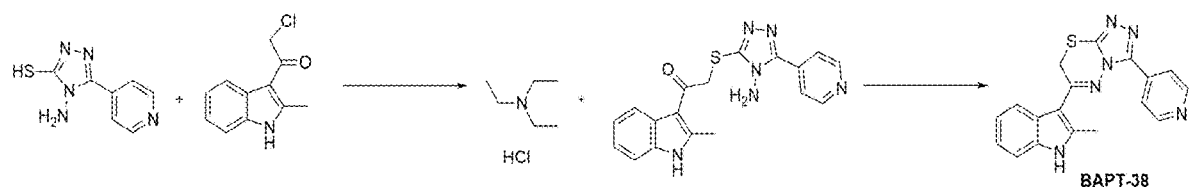
BAPT-38
Scheme 24
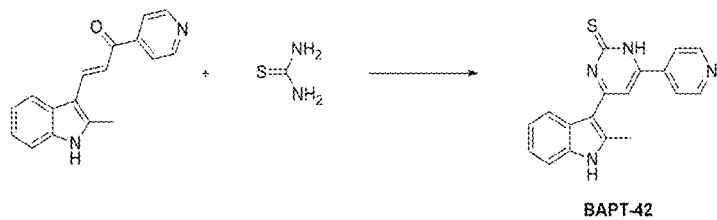
BAPT-42
Scheme 25
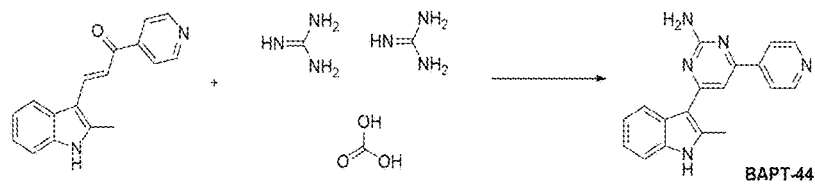
BAPT-44
FIG. 24A

Scheme 26
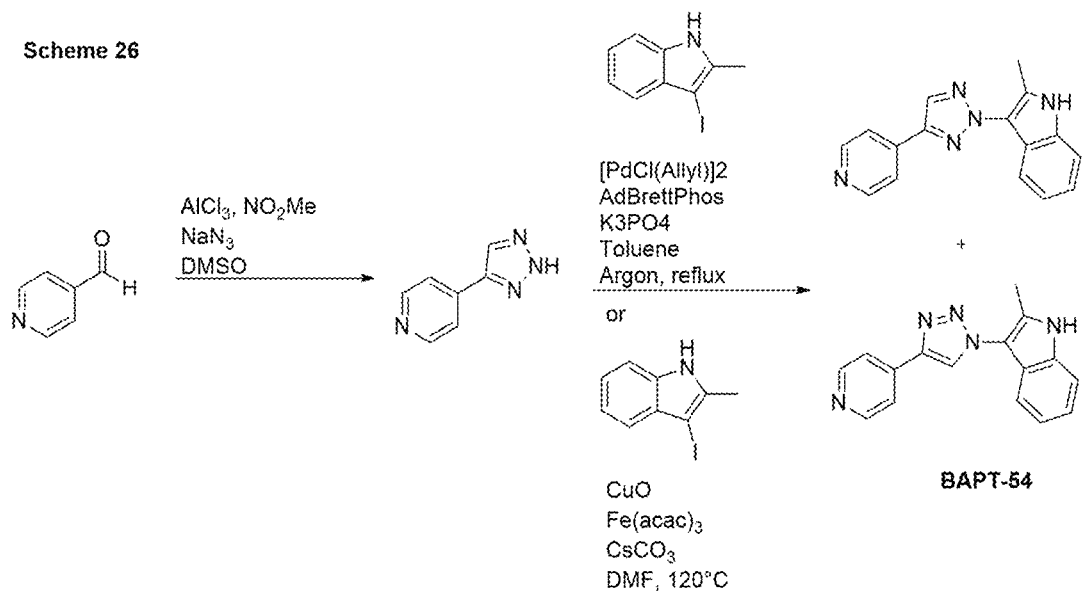
Scheme 27
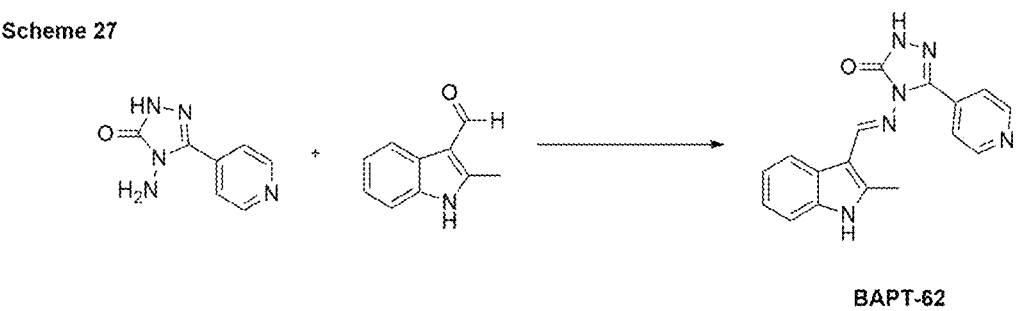
Scheme 28
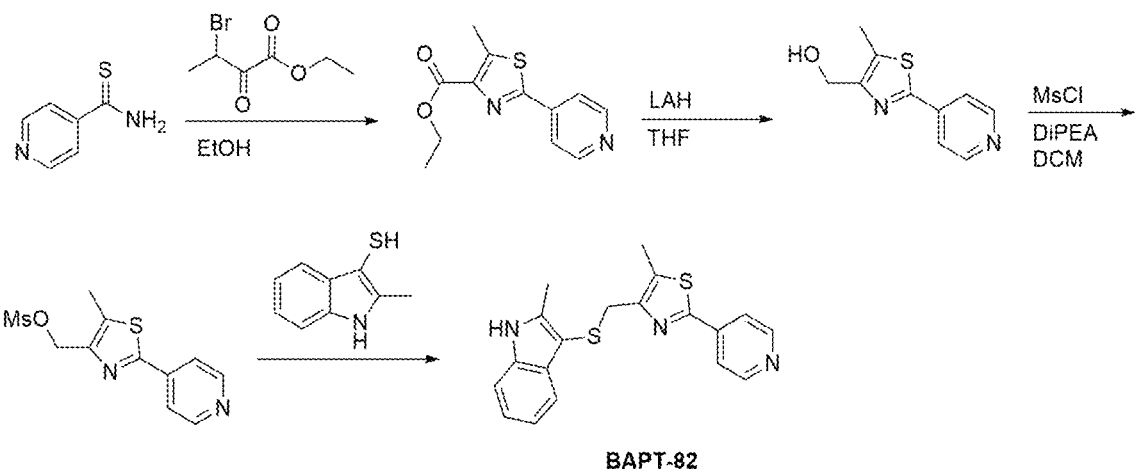
FIG. 24B

BT-20

U-251

BAPT-27

Lucifer Yellow

- BAPT-27 treatment results in:
- Vacuoles accumulation
- Cells expansion, no shrinkage

| Compound Codes | HCT-116 (colon cancer) | | | | BT-20 (TNBC) | | | | U251 (GBM) | | | |
|---|---|---|---|---|---|---|---|---|---|---|---|---|
| | Vacuoles (µM) | | Cell death (µM) | | Vacuoles (µM) | | Cell death (µM) | | Vacuoles (µM) | | Cell death (µM) | |
| | Small (<6 µm) | Large (≥6 µm) | With Vac | No Vac | Small (<6 µm) | Large (≥6 µm) | With Vac | No Vac | Small (<6 µm) | Large (≥6 µm) | With Vac | No Vac |
| BAPT-36 | <0.1 | 0.1 | 3 | > | <0.1 | 0.1 | 3 | > | 0.1 | 0.1 | 30 | > |
| BAPT-44 | 1 | 3 | 30 | > | 0.3 | 1 | 30 | > | 0.3 | 3 | >100 | > |
| BAPT-38 | 0.3 | 1 | 30 | > | 1 | 3 | 30 | > | 0.3 | 3 | 30 | > |
| BAPT-62 | NV | NV | NV | 100 | NV | NV | NV | >100 | NV | NV | NV | >100 |
| BAPT-42 | 10 | 30 | 10 | > | 10 | 30 | 30 | > | 3 | 10 | >100 | > |
| BAPT-86 | 30 | NV | >100 | > | 30 | NV | >100 | > | 30 | NV | >100 | > |
| BAPT-82 | NV | NV | >100 | > | NV | NV | NV | > | NV | NV | NV | 30 |
| BAPT-54 | 1 | 3 | 30 | > | 0.3 | 3 | 30 | > | 1 | 30 | 100 | > |
| BAPT-32 | 3 | 10 | 100 | > | 1 | NV | 100 | > | 0.3 | 3 | 100 | > |
| BAPT-78 | 100 | 100 | 100 | > | 100 | NV | 100 | > | 100 | 100 | >100 | > |
| BAPT-71 | 10 | 10 | 100 | > | 1 | NV | 100 | > | 3 | 30 | >100 | > |
| BAPT-30 | 3 | 10 | 30-100 | > | 1 | 10 | 30 | > | 0.3 | 3 | 100 | > |
| BAPT-28 | 1 | 10 | 100 | > | 3 | 10 | 30 | > | 1 | 3 | 100 | > |
| BAPT-31 | 10 | 30 | 30 | > | 30 | NV | 100 | > | 10 | 100 | >100 | > |
| BAPT-29 | 3 | 30 | 30 | > | 3 | 30 | 30 | > | 3 | 10 | 10 | > |
| BAPT-27 | 3 | 10 | 30 | > | 3 | 10 | 30 | > | 10 | 30 | >100 | > |

FIG. 54 - Table 1

| Compound Codes | HCT-116 (colon cancer) | | | | BT-20 (TNBC) | | | | U251 (GBM) | | | |
|---|---|---|---|---|---|---|---|---|---|---|---|---|
| | Vacuoles (µM) | | Cell death (µM) | | Vacuoles (µM) | | Cell death (µM) | | Vacuoles (µM) | | Cell death (µM) | |
| | Small (<6 µm) | Large (≥6 µm) | With Vac | No Vac | Small (<6 µm) | Large (≥6 µm) | With Vac | No Vac | Small (<6 µm) | Large (≥6 µm) | With Vac | No Vac |
| BAPT-36 | 0.1 | 0.1 | 3 | > | 0.1 | 0.1 | 3 | > | 0.1 | 0.1 | 3 | > |
| BAPT-44 | 0.3 | 1 | 30 | > | 0.3 | 1 | 30 | > | 0.3 | 3 | 30 | > |
| BAPT-38 | 0.3 | 1 | 30 | > | 1 | 3 | 30 | > | 0.3 | 1 | 10 | > |
| BAPT-62 | 10 | 100 | 100 | > | 30 | NV | 100 | > | 10 | 100 | >100 | > |
| BAPT-42 | 3 | 10 | 3 | > | 3 | 10 | 30 | > | 1 | 3 | 10 | > |
| BAPT-86 | 10 | NV | 30-100 | > | NV | NV | NV | > | 30 | NV | 30 | > |
| BAPT-82 | 100 | 100 | >100 | > | 30 | NV | >100 | >100 | NV | NV | NV | 30 |
| BAPT-54 | 1 | 3 | 3 | > | 0.3 | 1 | 30 | > | 0.3 | 1 | 10 | > |
| BAPT-32 | 3 | 3 | 30 | > | 1 | 10 | 30 | > | 0.3 | 3 | 30 | > |
| BAPT-78 | 100 | 100 | 100 | > | 100 | NV | 100 | > | 100 | 100 | >100 | > |
| BAPT-71 | 1 | 10 | 30 | > | 1 | 3 | 30-100 | > | 3 | 30 | 100 | > |
| BAPT-30 | 0.3 | 1 | 3 | > | 0.3 | 1 | 3 | > | 0.3 | 3 | 30 | > |
| BAPT-28 | 1 | 3 | 10 | > | 0.3 | 1 | 10 | > | 0.3 | 3 | 30 | > |
| BAPT-31 | 10 | 10 | 30 | > | 10 | 30 | 30 | > | 10 | 30 | 100 | > |
| BAPT-29 | 3 | 10 | 30 | > | 3 | 30 | 30 | > | 3 | 10 | 10 | > |
| BAPT-27 | 1 | 3 | 10 | > | 0.3 | 1 | 10 | > | 3 | 10 | 30 | > |

FIG. 55 - Table 2

MATERIALS AND METHODS USEFUL TO INDUCE CANCER CELL DEATH VIA METHUOSIS OR AUTOPHAGY OR A COMBINATION THEREOF

RELATED APPLICATIONS

This application is divisional application of Ser. No. 16/650,986 filed Mar. 26, 2020, now allowed, which is a national stage application filed under 35 U.S.C. § 371 of international application PCT/US2018/052809, filed under the authority of the Patent Cooperation Treaty on Sep. 26, 2018, which claims priority to U.S. Provisional Application No. 62/564,018 filed under 35 U.S.C. § 111(b) on Sep. 27, 2017, the disclosure of which is incorporated herein by reference in its entirety.

STATEMENT REGARDING FEDERALLY SPONSORED RESEARCH

This invention was made with no government support. The government has no rights in this invention.

BACKGROUND OF THE INVENTION

Current cancer chemotherapy uses a diverse array of chemotherapeutic agents that generally induce programmed cell death in cancer cells through activation of apoptosis pathways. However, during the course of treatment, cancer cells acquire mutations in genes that are normally associated with the promotion of efficient apoptotic responses. These mutations can diminish apoptosis and lead to chemo-resistant cancers when coupled with increased capacity for drug efflux and DNA repair. This renders many chemotherapeutic agents ineffective, and is especially relevant in recurrent and aggressive tumors. Therefore, there is a need in the art, especially for apoptosis-resistance cancers, to develop new therapeutics which target cancer cells via nonapoptotic cell death mechanisms.

SUMMARY OF THE INVENTION

Provided is a compound comprising Formula A:

Pyr-HET-Ar            Formula A wherein Pyr is a 4-pyridyl group, optionally substituted by up to three R groups each independently having various atoms up to 10; Ar is aryl, heteroaryl, aralkyl, or heteroaryl alkyl having 5 to 15 atoms, optionally substituted by up to three R groups each independently having various atoms up to 10; and HET is a linkage comprising a heterocyclic group; provided, however, that in some embodiments the compound is not BAPT-27:

BAPT-27

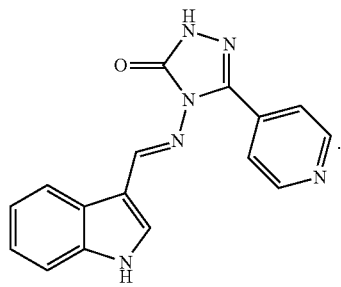

Also provided are salts, stereoisomers, solvates, hydrates, racemates, prodrugs, and polymorphs of Formula A.

In certain embodiments, the heterocyclic group is monocyclic or bicyclic. In certain embodiments, the heterocyclic group includes a one- or two-ring system having from one to four nitrogens, wherein the rings are either five-membered rings or six-membered rings. In certain embodiments, the heterocyclic group comprises a triazole thione.

In certain embodiments, Ar comprises pyridinyl, pyrimidinyl, thienyl, benzothiophenyl, pyrazolyl, oxazolyl, thiazolyl, indolyl, benzofuryl, indazolyl, or quinolinyl. In certain embodiments, Ar is selected from the group consisting of indol-3-yl, benzo[b]thiophen-3-yl, benzofuran-3-yl, 1H-indazol-3-yl, or quinolin-3-yl.

In certain embodiments, the compound comprises one of Formula II-XXII, or tautomers thereof:

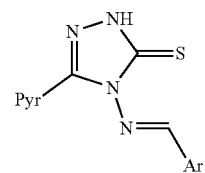

II

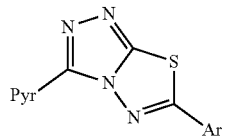

III

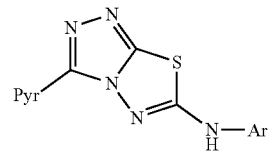

IV

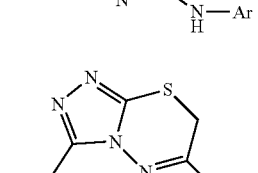

V

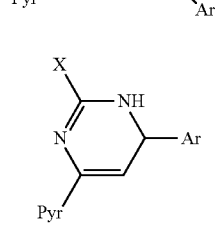

VI VII

X = SH
X = OH

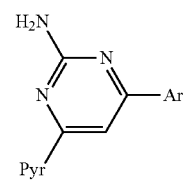

VIII

IX 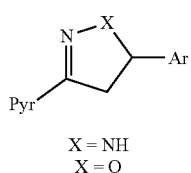
X = NH
X = O
XI 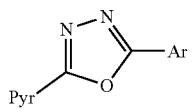
XII 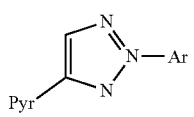
XIII 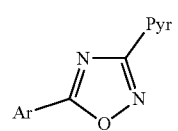
XIV 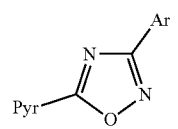
XV 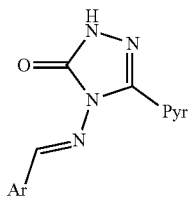
XVI 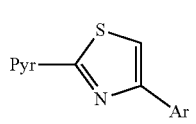
XVII 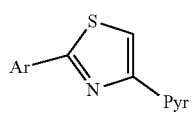
XVIII 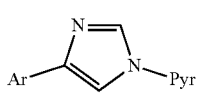
XIX 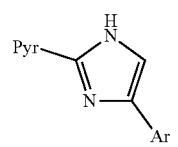
XX 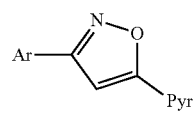
XXI 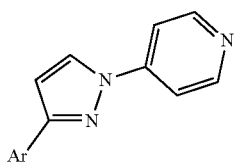
XXII 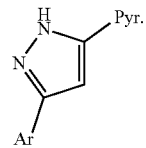
In particular embodiments, the tautomers comprise one of:
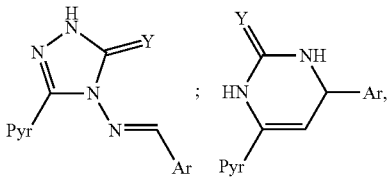
wherein Y is S or O; or
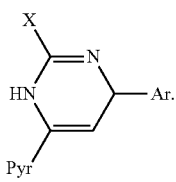
In certain embodiments, the compound comprises BAPT-15:
BAPT-15
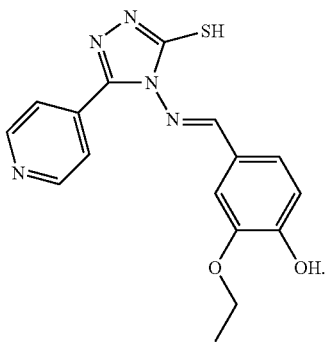

In certain embodiments, the compound comprises BAPT-27:

BAPT-27

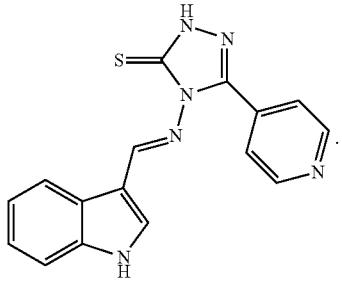

In certain embodiments, the compound comprises BAPT-36:

BAPT-36

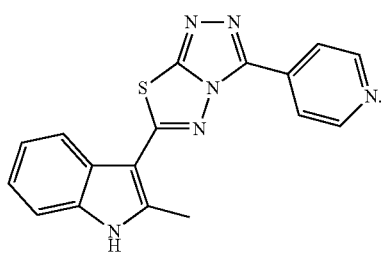

In certain embodiments, the compound comprises BAPT-54:

BATP-54

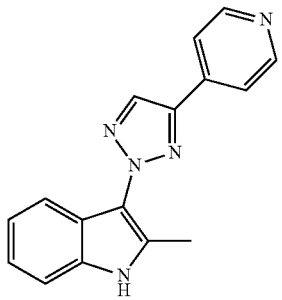

In certain embodiments, the 4-pyridyl group is not substituted.

Further provided is a pharmaceutical composition comprising a therapeutically effective amount of a compound of Formula A, where Formula A may include BAPT-27:

BAPT-27

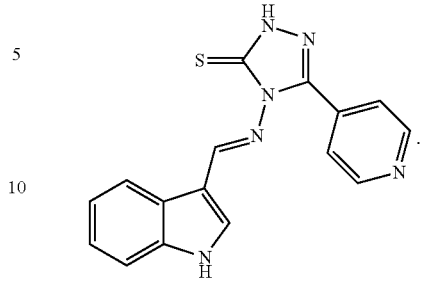

and a pharmaceutically acceptable carrier, adjuvant, or diluent. In certain embodiments, the pharmaceutical composition further comprises an anticancer agent which induces cancer cell death by an apoptotic process.

Further provided is a method of making a compound, the method comprising reacting a 4-pyridyl-containing triazole thione with a heteroaromatic aldehyde to produce a compound, wherein the compound comprises a 4-pyridyl group linked by a heterocyclic group to an aryl, heteroaryl, aralkyl, or heteroaryl alkyl. In certain embodiments, the 4-pyridyl-containing triazole thione comprises 4-amino-5-(pyridine-4-yl)-2,4-dihydro-3H-1,2,4-triazole-3-thione. In certain embodiments, the heteroaromatic carboxaldehyde comprises indole-3-carboxaldehyde.

Further provided is a method of inducing cell death in a cancer cell, the method comprising administering an effective amount of a compound of Formula A (where Formula A may include BAPT-27) to a cancer cell and inducing death of the cancer cell by methuosis, autophagy, or a combination of methuosis and autophagy. In certain embodiments, the compound comprises BAPT-15 or BAPT-27 or BAPT-36 or BAPT-54. In certain embodiments, the cancer cell is missing a pro-apoptotic gene comprising Bax, Bak, or both Bax and Bak. In certain embodiments, the cell death is independent of necrosis or necroptosis.

In certain embodiments, the compound induces rapid accumulation of extensive fluid filled cytoplasmic vacuoles in the cancer cell. In particular embodiments, the vacuoles are not inhibited by necroptosis inhibitors. In particular embodiments, the vacuoles comprise activated acidic compartments, and the cell death comprises alteration in autophagic signaling pathways. In certain embodiments, the cancer cell loses viability within 72 hours of the administering. In certain embodiments, the method further comprises administering an apoptosis-inducing agent to the cancer cell. In certain embodiments, the cancer cells resistant to mitoxantrone and/or doxorubicin are sensitized by the compounds.

In certain embodiments, the cancer cell is refractory to death by apoptosis-inducing anticancer agents. In certain embodiments, the cancer is colon cancer, lung cancer, ovarian cancer, prostate cancer, brain cancer, breast cancer or pancreatic cancer.

Further provided is a method of sensitizing a resistant cancer cells to cytotoxicity, the method comprising administering to a resistant cancer cell a combination therapy and sensitizing the resistant cancer cell to cytotoxicity, wherein the combination therapy comprises an antineoplastic agent in combination with a compound of Formula A (where Formula A may include BAPT-27). In certain embodiments, the antineoplastic agent comprises mitoxantrone. In certain embodiments, the cancer is colon cancer or lung cancer.

Further provided is a method of inhibiting cell growth, the method comprising administering an effective amount of a compound of Formula A (where Formula A may include BAPT-27) to a cell and inhibiting growth of the cell. In certain embodiments, the cell is a cancer cell. In certain embodiments, the compound comprises BAPT-15 or BAPT-27 or BAPT-36 or BAPT-54.

Further provided is a method of treating or ameliorating a cancer, the method comprising administering an effective amount of a compound to a patient having cancer and treating or ameliorating the cancer, where the compound comprises Formula A (where Formula A may include BAPT-27). In certain embodiments, the cancer is selected from the group consisting of colon cancer, lung cancer, ovarian cancer, prostate cancer, and pancreatic cancer. In certain embodiments, the compound comprises BAPT-15 or BAPT-27 or BAPT-36 or BAPT-54. In certain embodiments, the method further comprises administering an apoptosis-inducing agent to the patient.

Further provided is a method of activating lysosomes in a cell, the method comprising administering an effective amount of a compound to a cell and activating lysosomes in the cell, wherein the compound comprises Formula A (where Formula A may include BAPT-27). In certain embodiments, the compound comprises BAPT-27. In certain embodiments, the cell is a cancer cell.

Further provided is a pro-drug comprising a drug molecule linked to a compound of Formula A (where Formula A may include BAPT-27).

Further provided is a method of studying biological events, the method comprising administering to cells an effective amount of a compound of Formula A (where Formula A may include BAPT-27) to induce autophagy, methuosis, or a combination thereof in the cells, and studying biological events in the cells.

Further provided is a kit comprising a first container housing a 4-pyridyl-containing triazole thione compound, and a second container housing a phenolic aldehyde or indole-3-carboxaldehyde.

BRIEF DESCRIPTION OF THE DRAWINGS

The patent or application file may contain one or more drawings executed in color and/or one or more photographs. Copies of this patent or patent application publication with color drawing(s) and/or photograph(s) will be provided by the U.S. Patent and Trademark Office upon request and payment of the necessary fees.

FIG. 2: Scheme 1, depicting a general route for synthesizing compounds having a HET II linkage.

FIG. 3: Scheme 2, depicting a general route for synthesizing compounds having a HET III linkage.

FIG. 4: Scheme 3, depicting a general route for synthesizing compounds having a HET IV linkage.

FIG. 5: Scheme 4, depicting a general route for synthesizing compounds having a HET V linkage.

FIG. 6: Scheme 5, depicting a general route for synthesizing compounds having HET VI, VII, VIII, IX, and X linkages.

FIG. 7: Scheme 6, depicting a general route for synthesizing compounds having a HET XI linkage.

FIG. 8: Scheme 7, depicting a general route for synthesizing compounds having a HET XII linkage.

FIG. 9: Scheme 8, depicting a general route for synthesizing compounds having a HET XIII linkage.

FIG. 10: Scheme 9, depicting a general route for synthesizing compounds having a HET XIV linkage.

FIG. 11: Scheme 10, depicting a general route for synthesizing compounds having a HET XV linkage.

FIG. 12: Scheme 11, depicting a general route for synthesizing compounds having a HET XVI linkage.

FIG. 13: Scheme 12, depicting a general route for synthesizing compounds having a HET XVII linkage.

FIG. 14: Scheme 13, depicting a general route for synthesizing compounds having a HET XVIII linkage.

FIG. 15: Scheme 14, depicting a general route for synthesizing compounds having a HET XIX linkage.

FIG. 16: Scheme 15, depicting a general route for synthesizing compounds having a HET XX linkage.

FIG. 17: Scheme 16, depicting a general route for synthesizing compounds having a HET XXI linkage.

FIG. 18: Scheme 17, depicting a general route for synthesizing compounds having a HET XXII linkage.

FIG. 19: Scheme 18, depicting a general route for synthesizing compounds having a HET XXIII linkage.

FIG. 20: Scheme 19, depicting a general route for synthesizing compounds having a HET XXIV linkage.

FIG. 21: Scheme 20, depicting a general route for synthesizing compounds having a HET XXV linkage.

FIG. 24A: Schemes depicting synthesis of schemes 21-25 (BAPT-27, 36, 38, 42 and 44).

FIG. 24B: Schemes depicting synthesis of schemes 26-28 (BAPT-54, 62, 82).

FIG. 35A shows cells show vacuoles accumulation, cell expansion, and no shrinkage. FIG. 35B shows the BAPT-27 produces no alteration in the intrinsic apoptoic pathways (no activation of proapototic proteins and no inhibition of antiapoptotic proteins). FIG. 35C shows the nuclei show no apoptotic changes (no chromatin condensation or DNA fragmentation). FIG. 35D shows the annexin fluorescence was not changed upon treatment with BAPT-27.

FIGS. 50B-50C show increased autophagic vesicles (yellow) and increased lysosomal cargo (green).

FIG. 51C shows BAPT-27 significantly downregulated mTOR and increased Beclin-1 and LC3B-II autophagy related markers indicating significant autophagy.

FIG. 54—Table 1: Shows treatment of different BAPT compounds on HCT-116 (colon cancer), BT-20 (triple negative breast cancer) and U-251 (glioblastoma) cancer cell lines at 72 h. Formation of small or large vacuoles by different BAPT compounds leading to dell death at different concentrations, were observed and recorded. Vac or V; Vacuoles.

FIG. 55—Table 2: Shows treatment of different BAPT compounds on HCT-116 (colon cancer), BT-20 (triple negative breast cancer) and U-251 (glioblastoma) cancer cell lines at 72 h. Formation of small or large vacuoles by different BAPT compounds leading to dell death at different concentrations, were observed and recorded. Vac or V; Vacuoles.

DETAILED DESCRIPTION

Figure 1:
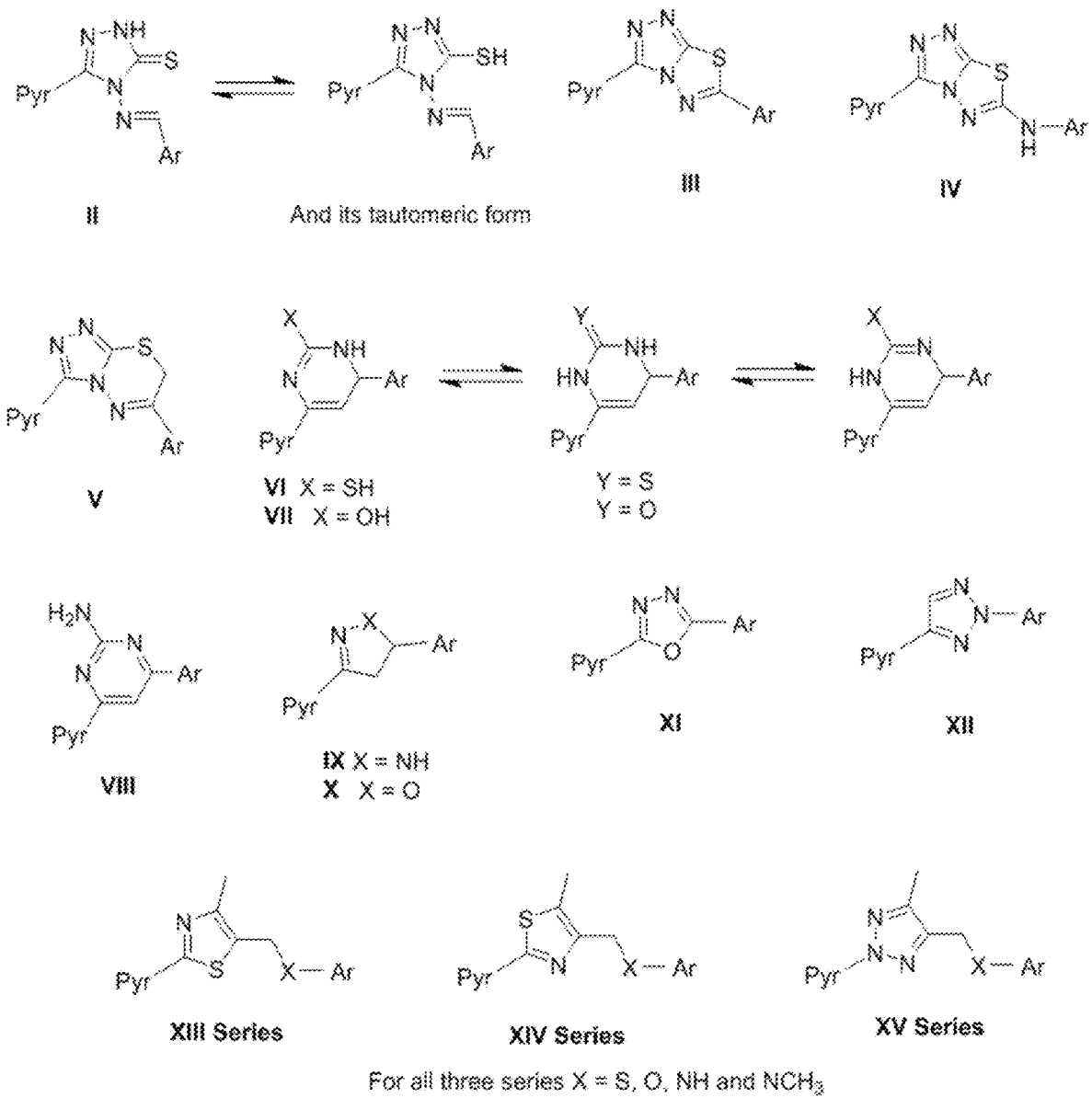
FIG. 1: Formulas II-XXV (also referred to as HET II-XXV), which are non-limiting example HET linkages in Formula A.

Throughout this disclosure, various publications, patents, and published patent specifications are referenced by an identifying citation. The disclosures of these publications, patents, and published patent specifications are hereby incorporated by reference into the present disclosure in their entirety to more fully describe the state of the art to which this invention pertains.

Definitions

For convenience, certain terms are defined, and certain concepts are established, prior to further description of the present disclosure.

Unless stereochemistry is specifically indicated, all stereoisomers of the compounds herein are included, as pure compounds as well as mixtures thereof. It will be appreciated by one of ordinary skill in the art that asymmetric centers may exist in any of the compounds disclosed herein. Thus, the compounds and compositions thereof may be in the form of an individual enantiomer, diastereomer, or geometric isomer, or may be in the form of a mixture of stereoisomers. In certain embodiments, the compounds herein are enantiopure compounds. In certain other embodiments, mixtures of stereoisomers or diastereomers are provided. Additionally, the compounds encompass both (Z) and (E) double bond isomers (or cis and trans isomers) unless otherwise specifically designated. Thus, compounds generally depicted in structures herein encompass those structures in which double bonds are (Z) or (E).

The term "composition" as used herein is intended to encompass a product comprising the specified ingredients in the specified amounts, as well as any product that results, directly or indirectly, from combinations of the specified ingredients in the specified amounts.

The term "solvate" refers to a pharmaceutically acceptable solid form of a specified compound containing solvent molecules as part of the crystal structure. A solvate typically retains at least some of the biological effectiveness of such compound. Solvates can have different solubilities, hygroscopicities, stabilities, and other properties. Examples of solvates include, but are not limited to, compounds in combination with water, isopropanol, ethanol, methanol, DMSO, ethyl acetate, acetic acid, or ethanolamine. Solvates are sometimes termed "pseudopolymorphs."

The term "hydrate" refers to a solvate with water.

The term "racemate" refers to a mixture that contains an equal amount of enantiomers.

The term "polymorph" means a crystalline form of a substance that is distinct from another crystalline form of the substance but that shares the same chemical formula.

It will be appreciated that any of the compounds described herein may be substituted with any number of substituents or functional moieties. In general, the term "substituted," whether preceded by the term "optionally" or not, and substituents contained in formulas, refer to the replacement of hydrogen atoms in a given structure with a specified substituent. When more than one position in any given structure may be substituted with more than one substituent selected from a specified group, the substituent may be either the same or different at every position. The term "substituted" is contemplated to include all permissible substituents of organic compounds. In a broad aspect, the permissible substituents include acyclic and cyclic, branched and unbranched, carbocyclic and heterocyclic, aromatic and nonaromatic substituents or organic compounds. For purposes of explanation herein, heteroatoms such as nitrogen may have hydrogen substituents and/or any permissible substituents of organic compounds described herein which satisfy the valencies of the heteroatoms. Furthermore, there is not any intention to be limited in any manner by the permissible substituents of organic compounds. Combinations of substituents and variables envisioned are, in some embodiments, those that result in the formation of stable compounds useful in the treatment, for example, of cancers.

The term "pharmaceutically acceptable carrier" means a medium that is used to prepare a desired dosage form of a compound. A pharmaceutically acceptable carrier includes solvents, diluents, or other liquid vehicles; dispersion or suspension aids; surface active agents; isotonic agents; thickening or emulsifying agents; preservatives; solid binders; lubricants; and the like.

The term "alkyl" refers to monovalent alkyl groups having from 1 to 50 carbon atoms, preferably having from 1 to 10 carbon atoms, and more preferably having from 1 to 6 carbon atoms. This term is exemplified by groups such as methyl, ethyl, n-propyl, iso-propyl, n-butyl, iso-butyl, n-hexyl, and the like. "Substituted alkyl" refers to an alkyl group, preferably of from 1 to 10 carbon atoms, having from 1 to 3 substituents selected from the group consisting of alkoxy, substituted alkoxy, acyl, acylamino, amino, aminoacyl, aminocarboxy esters, cyano, cycloalkyl, halogen, hydroxyl, carboxyl, carboxylalkyl, oxyacyl, oxyacylamino, thiol, thioalkoxy, substituted thioalkoxy, aryl, heteroaryl, heterocyclic, aryloxy, thioaryloxy, heteroaryloxy, thioheteroaryloxy, nitro, and mono- and di-alkylamino, mono- and di-(substituted alkyl)amino, mono- and di-arylamino, mono- and di-heteroarylamino, mono- and di-heterocyclic amino, and unsymmetric di-substituted amines having different substituents selected from alkyl, substituted alkyl, aryl, heteroaryl, and heterocyclic.

The term "aryl" refers to an unsaturated aromatic carbocyclic group, preferably of from 6 to 14 carbon atoms, having a single ring (e.g., phenyl) or multiple condensed rings (e.g., naphthyl or anthryl), preferably having from 1 to 3 rings. Some example aryls include phenyl, naphthyl, and the like. Unless otherwise constrained by the definition for the aryl substituent, such aryl groups can optionally be substituted with from 1 to 3 substituents selected from the group consisting of hydroxy, acyl, alkyl, alkoxy, alkenyl, alkynyl, substituted alkyl, substituted alkoxy, substituted alkenyl, substituted alkynyl, amino, aminoacyl, aminocarboxy esters, alkaryl, aryl, aryloxy, carboxyl, carboxylalkyl, acylamino, cyano, halo, nitro, heteroaryl, heterocyclic, oxyacyl, oxyacylamino, thioalkoxy, substituted thioalkoxy, trihalomethyl, mono- and di-alkylamino, mono- and di-(substituted alkyl)amino, mono- and di-arylamino, mono- and di-heteroarylamino, mono- and di-heterocyclic amino, and unsymmetric di-substituted amines having different substituents selected from alkyl, substituted alkyl, aryl, heteroaryl, heterocyclic, and the like. Some example substituents include alkyl, alkoxy, halo, cyano, nitro, trihalomethyl, and thioalkoxy.

The terms "heteroaryl" or "hetaryl" refer to a group that is both heterocyclic and aromatic.

The term "aralkyl" refers to a group derived from an alkyl radical by replacing one or more hydrogen atoms with aryl groups. Thus, the term "aralkyl" refers to alkylene-aryl groups. In some examples, aralkyl groups have from 1 to 10 carbon atoms in the alkylene moiety and from 6 to 10 carbon atoms in the aryl moiety, however other aralkyl groups are entirely possible and encompassed within the present disclosure.

GENERAL DESCRIPTION

Provided herein are materials and methods to induce cell death through a nonapoptotic mechanism, namely methuosis or autophagy, or a combination of both (i.e., methuophagy). Small molecules are described which act through these mechanisms with therapeutic applications in disorders or anomalies that involve cell proliferation, metastasis, and drug resistance, such as, but not limited to, cancers. The structure activity relationship and the pharmacophore important for producing this cell death are also described. The methuophagy induces cell death by the formation of extensive cytoplasmic fluid-filled vacuoles with autophagic features. The vacuolated cells finally burst, detached, and die in a mechanism that is independent of apoptosis and necroptosis. Without wishing to be bound by theory, it is believed that such mechanism is due to targeting the metabolic reprogramming and cellular organelles. Several small molecules have been discovered to act through methuosis, autophagy, or methuophagy, with therapeutic applications in disorders involving cell proliferation such as human and animal cancer.

Methuosis is a recently identified nonapoptotic cell death mechanism observed in glioblastoma cells. The hallmark of this form of cell death is displacement of the cytoplasm by large fluid-filled vacuoles derived from macropinosomes. Autophagy is another type of nonapoptotic cell death that is known. Autophagy occurs in the absence of chromatin condensation but is accompanied by large-scale autophagic vacuolization of the cytoplasm.

Simultaneously targeting both autophagy and methuosis represents an attractive strategy for development of cancer therapeutics, especially for apoptosis-resistant cancers where the current proapoptotic chemotherapeutic agents are not effective. This newly characterized form of nonapoptotic cell death in cancer cells is termed "methuophagy". Other applications for agents which induce methuophagy include use as a delivery vehicles, prodrug activators, chemoadjuvants, and chemosensitizers.

Various embodiments of compounds, compositions, and methods of the present disclosure can induce cancer cell death via methuosis, autophagy, or a combination of both methuosis and autophagy (i.e., methuophagy). The examples herein demonstrate that certain of these compounds can be effective for treatment of different types of cancers.

Disclosed herein are compounds that induce cell death with hallmarks of methuophagy (methuosis, autophagy, or a combination of both), a non-apoptotic cell death mechanism. In general, the compounds contain a 4-substituted-pyridyl group (Pyr) and an aryl group (Ar) linked in a conformationally constrained arrangement by heterocyclic systems (HET). This general pattern is depicted in Formula A:

Pyr-HET-Ar    Formula A

The 4-pyridyl group may be further substituted by up to three R groups each independently having various atoms up to 10. Ar may be aryl, heteroaryl, aralkyl, or heteroaryl alkyl having 5 to 15 atoms, and may also be further substituted by up to three R groups each independently having various atoms up to 10.

HET is a linkage that comprises a heterocyclic group. In some embodiments, HET is a constrained heterocyclic group. Non-limiting examples of specific HET linkages are shown in FIG. 1, in Formulas II to XXV. Tautomers are depicted in FIG. 1 for the amino-triazole-thione (hereinafter ATT) II and for linkages VI and VII. The compounds II-XXV can be accessed synthetically using synthetic protocols depicted in general Schemes 1 to 20 (FIGS. 2-21). The HET linkage can include either monocyclic or bicyclic heterocycles. As seen from compounds II-XXV, the heterocyclic group can include one- or two-ring systems having from one to four nitrogens, where the rings are either five-membered rings or six-membered rings. In some non-limiting examples, the HET linkage includes a triazole thione.

Figure 22:
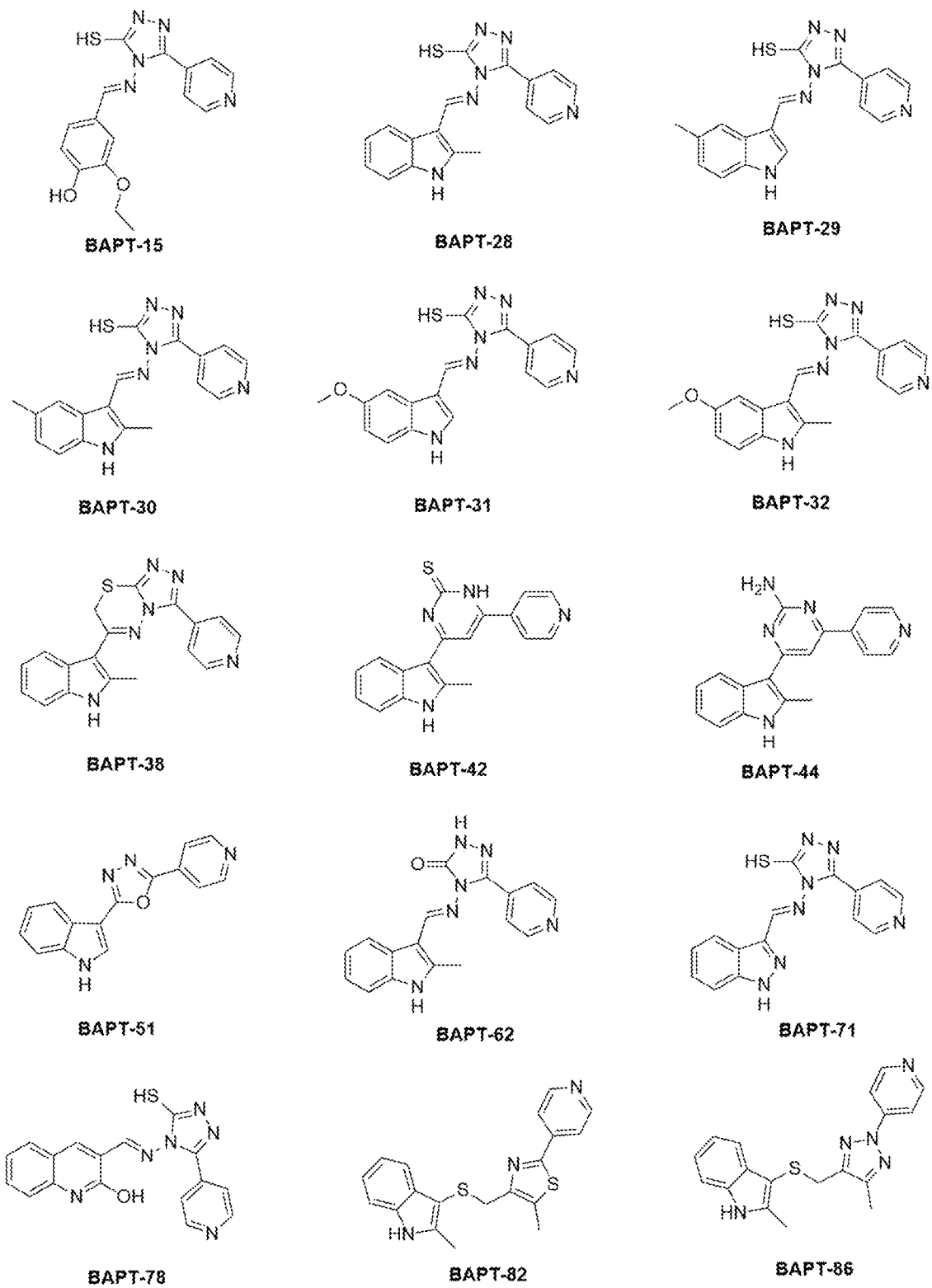
FIG. 22: Structural formulas of non-limiting example compounds of Formula A, namely BAPT-15, BAPT-28, BAPT-29, BAPT-30, BAPT-31, BAPT-32, BAPT-38, BAPT-42, BAPT-44, BAPT-51, BAPT-62, BAPT-71, BAPT-78, BAPT-82, and BAPT-86.

Non-limiting examples of compounds of Formula A are depicted in FIG. 22. These compounds are named BAPT-15, BAPT-28, BAPT-29, BAPT-30, BAPT-31, BAPT-32, BAPT-38, BAPT-42, BAPT-44, BAPT-51, BAPT-62, BAPT-71, BAPT-78, BAPT-82, and BAPT-86.

Figure 23:
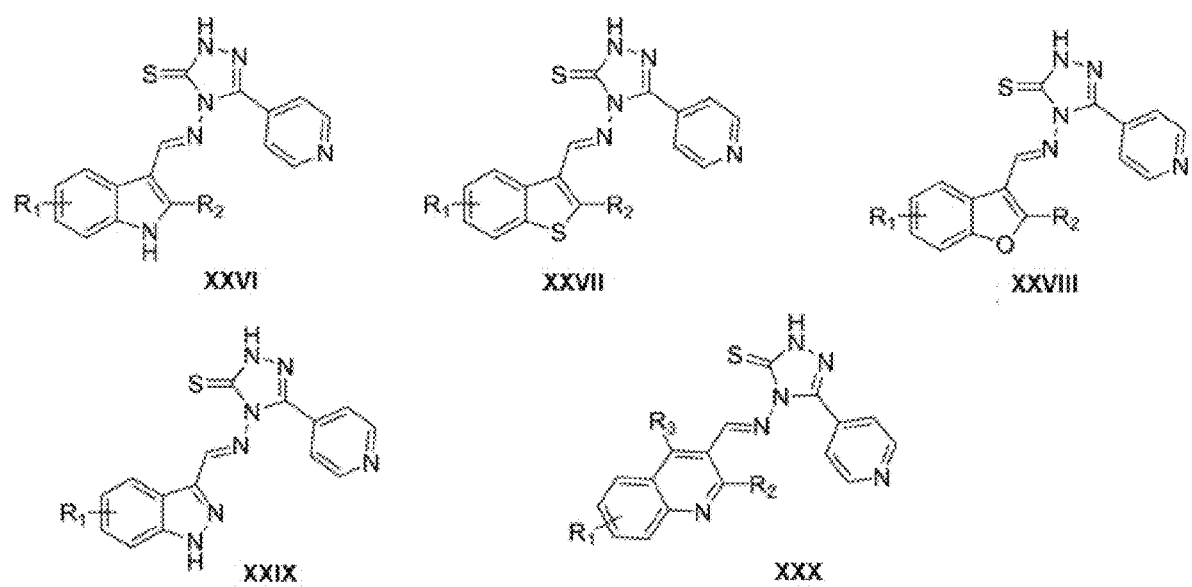
FIG. 23: Structural formulas of non-limiting example compounds of Formula A, namely Formulas XXVI-XXX. The substitutions $R_1$, $R_2$, and $R_3$ are optional.

In some embodiments, Ar is a hetaryl group such as, but not limited to, pyridinyl, pyrimidinyl, thienyl, benzothiophenyl, pyrazolyl, oxazolyl, thiazolyl, indolyl, benzofuryl, indazolyl, or quinolinyl. Some non-limiting examples of heteraryl rings are indol-3-yl (Formula XXVI), benzo[b]thiophen-3-yl (Formula XXVII), benzofuran-3-yl (Formula XXVIII), 1H-indazol-3-yl (Formula XXIX), or quinolin-3-yl (Formula XXX), with or without substitutions $R_1$, $R_2$, and/or $R_3$. These embodiments are depicted in FIG. 23.

Another non-limiting example of a compound of Formula A, where Ar is a hetaryl group, is BAPT-27, which has structural formula XXXI, and its equilibrium tautomer:

BAPT-27

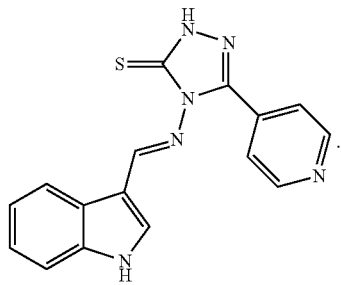

XXXI

Another non-limiting example of a compound of Formula A, where Ar is a hetaryl group, is BAPT-36, which has structural formula XXXII:

BAPT-36

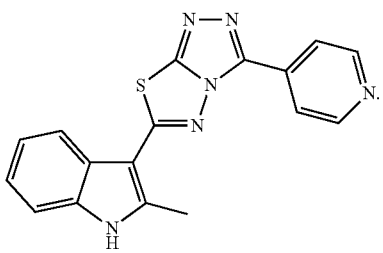

XXXIII

Another non-limiting example of a compound of Formula A, where Ar is a hetaryl group, is BAPT-27, which has structural formula XXXIII:

BAPT-54

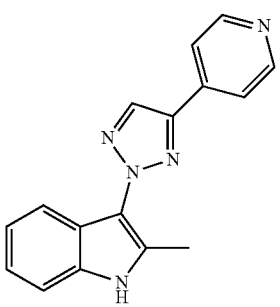

XXXIII

The compounds of the present disclosure are prepared, for example, by the reaction sequences shown in the general synthetic Schemes 1-20 (FIGS. 2-21). A person skilled in the art could readily adapt such synthesis to prepare the corresponding compounds. For example, a 4-pyridyl-containing triazole thione compound can be reacted with a indole-3-carboxaldehyde to produce a compound of Formula A. As one particular non-limiting example of such an adaptation, BAPT-27 (XXXI) can be prepared according to Scheme 21 (FIG. 24), in which 4-amino-5-(pyridine-4-yl)-2,4-dihydro-3H-1,2,4-triazole-3-thione is reacted with indole-3-carboxaldehyde under reflux in acetic acid to afford BAPT-27.

Therapeutic Uses

In general, the compounds of Formula A are useful for inducing vacuolization and/or cell death. The present disclosure can therefore be exploited in several pathological conditions such as cancer, infection, pro-drug, drug delivery, and overcoming drug resistance. The cancers include colorectal cancer, pancreatic cancer, glioblastoma, lung cancer, brain cancer, breast cancer, prostate cancer, leukemia, melanoma, cervical cancer, bladder cancer, kidney cancer, multiple myeloma, or other blood cancers. The cancer may include mitoxantrone-resistant, doxorubicin-resistant, apoptotic-resistant, and/or multidrug-resistant tumor cells. Other uses will also be recognized by those skilled in the art.

The compounds of Formula A, such as but not limited to BAPT-27, can be used in treating many different types of primary cancers including colon, lung, pancreatic, ovarian, brain, gastrointestinal, and skin, among other types of cancers. The compounds can also be used as chemo-adjuvant agents and added to the treatment regimens in case of recurrent cancer that usually become refractory to conventional treatment after initial response. This combination is believed to improve patient responsiveness and restore cancer sensitivity to anticancer agents. The compounds may also be used to target and reverse cancer metastasis in all the above-mentioned types of cancer. Further, the clinical uses of this compound can be extended to veterinary medicine.

One or more of the compounds of Formula A may be administered without additional anticancer agents. Alternatively, combination therapies are possible. In some embodiments, one or more of the compounds of Formula A are administered in combination with one or more other anticancer agents, including with those anticancer agents that act via inducing apoptotic cell death or drugs that act via damaging DNA. The dosage of the one or more compounds of the present disclosure is optionally less than the dosage when they are administered alone. Similarly, the dosage of the other anticancer agent is optionally less than the dosage of the other anticancer agent when administered alone.

Drug Delivery Systems

The present disclosure can also be used for and along with drug delivery systems for important drugs and therapeutics macromolecules that are unable to penetrate cellular membranes (thereby limiting their beneficial effects). As shown in the Examples herein, BAPT-27 (as an example Formula A compound) forms macropinocytic vacuoles that start to form from projections at the cellular membranes called ruffles that transfer round and trap the extracellular fluids, and transfer them inside of the cells. Such an ability can be used to transfer therapeutic macromolecules including, but not limited to, large proteins, monoclonal antibodies, siRNA, oligonucleotide, and hydrophilic compounds, among others. Similarly, the compounds of Formula A can also be used to transfer and enhance the uptake of microparticulate & nanoparticulate drug delivery systems with or without drugs including, but not limited to, microparticles, microcapsules, microspheres, nanoparticles, vesicular systems, e.g., liposomes, multiwalled carbon nanotubes (MWCNTs), and quantum dots, among others. The macromolecules/microparticles/nanoparticles in the extracellular fluid can get the benefit from the vacuole forming capacities of Formula A compounds such as BAPT-27 to become trapped inside the cell to exert their required activities. Additionally, as shown in the Examples, the compounds of Formula A produce enhanced lysosomal activity, increase lysosomal numbers, and increase size, indicating further usefulness in pro-drugs therapy.

Research Use

The compounds of Formula A, such as BAPT-27, can have a wide range of applications in research. The compounds can be used a positive control to induce autophagy, methuosis, or their combination 'methuophagy' and vacuolization for studying the biological events related to its effects. These agents can be used to understand the cellular metabolic reprogramming. They can be used to analyze the formation of vacuoles and tracking their fusion and burst, membrane fusion events, analyze the changes in intracellular trafficking signaling, as well as the effects on cellular organelles including mitochondria, lysosomal, and endosomal compartments, golgi apparatus, and nuclei, among others. BAPT-27 and other Formula A compounds can be used as lead compounds for future drug discovery development of more generations of more potent methuophagy inducing agents, vacuole-inducing agents, as well as non-apoptotic cell-death inducing agents. The compounds can be used for high throughput screening in many in vitro assays to identify molecular targets for such compounds. The compounds can be used in overcoming drug resistance mediated by conventional efflux ABC transporters, i.e., Pgp and ABCG2, and understanding ways to overcome non-conventional drug resistance mechanisms, i.e., apoptotic drug resistance.

Formulations

The compounds described herein can be used and administrated in different type of simple and complex formulations. They can be formulated simply by dissolving it in different solutions. Alternatively, they can be formulated as complex pharmaceutical delivery systems such as tablets, capsules, powders, with a range of reagents, excipients, stabilizers, etc.

Pharmaceutical compositions of the present disclosure comprise an effective amount of a compound of Formula A (such as, but not limited to, BAPT-27), and/or additional agents, dissolved or dispersed in a pharmaceutically acceptable carrier. The phrases "pharmaceutical" or "pharmacologically acceptable" refer to molecular entities and compositions that produce no adverse, allergic, or other untoward reaction when administered to an animal, such as, for example, a human. The preparation of a pharmaceutical composition that contains at least one compound or additional active ingredient will be known to those of skill in the art in light of the present disclosure, as exemplified by Remington's Pharmaceutical Sciences, 2003, incorporated herein by reference. Moreover, for animal (e.g., human) administration, it is understood that preparations should meet sterility, pyrogenicity, general safety, and purity standards as required by FDA Office of Biological Standards.

A composition disclosed herein may comprise different types of carriers depending on whether it is to be administered in solid, liquid or aerosol form, and whether it need to be sterile for such routes of administration as injection. Compositions disclosed herein can be administered intravenously, intradermally, transdermally, intrathecally, intraarterially, intraperitoneally, intranasally, intravaginally, intrarectally, intraosseously, periprosthetically, topically, intramuscularly, subcutaneously, mucosally, intraosseosly, periprosthetically, in utero, orally, topically, locally, via inhalation (e.g., aerosol inhalation), by injection, by infusion, by continuous infusion, by localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 2003, incorporated herein by reference).

The actual dosage amount of a composition disclosed herein administered to an animal or human patient can be determined by physical and physiological factors such as body weight, severity of condition, the type of disease being treated, previous or concurrent therapeutic interventions, idiopathy of the patient, and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In certain embodiments, a composition herein and/or additional agent is formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsules, they may be compressed into tablets, or they may be incorporated directly with the food of the diet.

In further embodiments, a composition described herein may be administered via a parenteral route. As used herein, the term "parenteral" includes routes that bypass the alimentary tract. Specifically, the pharmaceutical compositions disclosed herein may be administered, for example but not limited to, intravenously, intradermally, intramuscularly, intraarterially, intrathecally, subcutaneous, or intraperitoneally (U.S. Pat. Nos. 6,753,514, 6,613,308, 5,466,468, 5,543,158; 5,641,515; and 5,399,363 are each specifically incorporated herein by reference in their entirety).

Solutions of the compositions disclosed herein as free bases or pharmacologically acceptable salts may be prepared in water suitably mixed with a surfactant, such as hydroxypropylcellulose. Dispersions may also be prepared in glycerol, liquid polyethylene glycols and mixtures thereof, and in oils. Under ordinary conditions of storage and use, these preparations may contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In some cases, the form should be sterile and should be fluid to the extent that easy injectability exists. It should be stable under the conditions of manufacture and storage and should be preserved against the contaminating action of microorganisms, such as bacteria and fungi. The carrier can be a solvent or dispersion medium containing, for example, water, ethanol, polyol (i.e., glycerol, propylene glycol, liquid polyethylene glycol, and the like), suitable mixtures thereof, and/or vegetable oils. Proper fluidity may be maintained, for example, by the use of a coating, such as lecithin, by the maintenance of the required particle size in the case of dispersion, and/or by the use of surfactants. The prevention of the action of microorganisms can be brought about by various antibacterial and antifungal agents, such as, but not limited to, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption such as, for example, aluminum monostearate or gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

Sterile injectable solutions are prepared by incorporating the compositions in the required amount in the appropriate solvent with various other ingredients enumerated above, as required, followed by filtered sterilization. Generally, dispersions are prepared by incorporating the various sterilized compositions into a sterile vehicle which contains the basic dispersion medium and the required other ingredients from those enumerated above. In the case of sterile powders for the preparation of sterile injectable solutions, some methods of preparation are vacuum-drying and freeze-drying techniques which yield a powder of the active ingredient plus any additional desired ingredient from a previously sterile-filtered solution thereof. A powdered composition is combined with a liquid carrier such as, but not limited to, water or a saline solution, with or without a stabilizing agent.

In other embodiments, the compositions may be formulated for administration via various miscellaneous routes, for example, topical (i.e., transdermal) administration, mucosal administration (intranasal, vaginal, etc.), and/or via inhalation.

Pharmaceutical compositions for topical administration may include the compositions formulated for a medicated application such as an ointment, paste, cream, or powder. Ointments include all oleaginous, adsorption, emulsion, and water-soluble based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones, and luarocapram. Possible bases for compositions for topical application include polyethylene glycol, lanolin, cold cream, and petrolatum, as well as any other suitable absorption, emulsion, or water-soluble ointment base. Topical preparations may also include emulsifiers, gelling agents, and antimicrobial preservatives as necessary to preserve the composition and provide for a homogenous mixture. Transdermal administration of the compositions may also comprise the use of a "patch." For example, the patch may supply one or more compositions at a predetermined rate and in a continuous manner over a fixed period of time.

In certain embodiments, the compositions may be delivered by eye drops, intranasal sprays, inhalation, and/or other aerosol delivery vehicles. Methods for delivering compositions directly to the lungs via nasal aerosol sprays has been described in U.S. Pat. Nos. 5,756,353 and 5,804,212 (each specifically incorporated herein by reference in their entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts and could be employed to deliver the compositions described herein. Likewise, transmucosal drug delivery in the form of a polytetrafluoroetheylene support matrix is described in U.S. Pat. No. 5,780,045 (specifically incorporated herein by reference in its entirety), and could be employed to deliver the compositions described herein.

It is further envisioned the compositions disclosed herein may be delivered via an aerosol. The term aerosol refers to a colloidal system of finely divided solid or liquid particles dispersed in a liquefied or pressurized gas propellant. The typical aerosol for inhalation consists of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

In particular embodiments, the compounds and compositions described herein are useful for treating various cancers such as, but not limited to: colorectal cancer, pancreatic cancer, glioblastoma, lung cancer, brain cancer, breast cancer, prostate cancer, leukemia, melanoma, cervical cancer, bladder cancer, kidney cancer, multiple myeloma, or other blood cancers. The cancers may be mitoxantrone-resistant, doxorubicin-resistant, apoptotic-resistant, and/or multidrug-resistant cancers. Furthermore, as noted above, the compounds and compositions herein can be used in combination therapies. That is, the compounds and compositions can be administered concurrently with, prior to, or subsequent to one or more other desired therapeutic or medical procedures or drugs. The particular combination of therapies and procedures in the combination regimen will take into account compatibility of the therapies and/or procedures and the desired therapeutic effect to be achieved. Combination therapies include sequential, simultaneous, and separate administration of the active compound in a way that the therapeutic effects of the first administered procedure or drug is not entirely disappeared when the subsequent procedure or drug is administered.

By way of a non-limiting example of a combination therapy, the compounds or compositions described herein can be administered in combination with one or more suitable anti-cancer agents including, but not limited to: chemotherapeutic agents; cytotoxins; antimetabolites; alkylating agents; protein kinase inhibitors; anthracyclines; antibiotics; miRNAs; anti-miRNAs; antimitotic agents (e.g. antitubulin agents); corticosteroids; radiopharmaceuticals; proteins such as cytokines, enzymes, or interferons; biological response modifiers such as krestin, lentinan, sizofiran, picibanil, ubenimex; anti-angiogenic compounds such as acitretin, fenretinide, thalidomide, zoledronic acid, angiostatin, aplidine, cilengtide, combretastatin A-4, endostatin, halofuginone, rebimastat, Removab®, Revlimid®, squalamine, ukrain, or Vitaxin®; platinum-coordinated compounds such as cisplatin, carboplatin, nedaplatin, or oxaliplatin; camptothecin derivatives such as camptothecin, 10-hydroxycamptothecin, 9-aminocamptothecin, irinotecan, SN-38, edotecarin, or topotecan; compounds or chelates that include radionuclides; or combinations thereof. Examples of suitable interferons include, but are not limited to interferon alpha, interferon alpha-2a, interferon, alpha-2b, interferon beta, interferon gamma-1a, interferon gamma-1 b (Actimmune), interferon gamma-n1, or combinations thereof.

In certain embodiments, the anti-cancer agent is one or more of hydroxyureas, Taxol®, adriamycin, 5-fluorouracil, cyclophosphamide, etoposide, altretamine, ifosfamide, vinblastine sulfate, estramustine phosphate, suramin, strontium-89, filgrastim, lentinan, sizofilan, TheraCys®, ubenimex, WF-10, aldesleukin, alemtuzumab, BAM-002, dacarbazine, daclizumab, denileukin, gemtuzumab ozogamicin, ibritumomab, imiquimod, lenograstim, lentinan, Corixa, molgramostim, OncoVAX-CL, sargramostim, tasonermin, tecleukin, thymalasin, tositumomab, Virulizin®, Z-100, epratuzumab, mitumomab, oregovomab, pemtumomab (Y-muHMFGI), Provenge® (Dendreon), alitretinoin, ampligen, atrasentan bexarotene, bortezomib, bosentan, calcitriol, exisulind, finasteride, fotemustine, ibandronic acid, miltefosine, mitoxantrone, 1-asparaginase, procarbazine, dacarbazine, hydroxycarbamide, pegaspargase, pentostatin, tazarotne, Telcyta® (TLK-286, Telik Inc.), Velcade® (bortemazib, Millenium), or tretinoinor.

Another non-limiting example of a combination therapy for cancers or other diseases is the combination of Formula A compounds or Formula A compound-containing composition with one or more surgical treatments. Suitable surgical treatments include, but are not limited to, a polypectomy, a colectomy, a transanal resection, a wedge resection, a lobectomy, a pneumonectomy, a sleeve reduction, a hysterectomy, a bilateral salpingo-oophorectomy, an omentectomy, or a nephrectomy. Other possible therapies suitable for combination with a Formula A compound or Formula A compound-containing composition include, but are not limited to, immunotherapy, hormone therapy, radiation therapy, or a combination thereof.

As shown in the Examples herein, the compounds of Formula A are also useful for sensitizing resistant cancer cells to cytotoxicity by other agents, such as antineoplastic agents. For example, a combination of BAPT-27 and the antineoplastic agent mitoxantrone renders resistant colon cancer cells and resistant lung cancer cells vulnerable to cytoxicity by mitoxantrone. Thus, further provided herein are methods and compositions useful for sensitizing resistance cancers to cytotoxicity by anticancer agents.

Embodiments of the present disclosure further include methods of determining coverage or denial of health insurance reimbursement and/or payment for treatments of disease comprising the compounds or compositions described herein. In certain embodiments, the treatment comprises a compound of Formula A, and a provider of health insurance denies coverage or reimbursement for the treatment.

Kits

It is envisioned that the compounds, compositions, and methods described herein could be embodied as parts of a kit or kits. A non-limiting example of such a kit is a kit for making a compound of Formula A, the kit comprising a 4-pyridyl-containing triazole thione and an aryl/heteroaryl aldehyde in separate containers, where the containers may or may not be present in a combined configuration. Many other kits are possible, such as kits further comprising a pharmaceutically acceptable carrier, diluent, or excipient. The kits may further include instructions for using the components of the kit to practice the subject methods. The instructions for practicing the subject methods are generally recorded on a suitable recording medium. For example, the instructions may be present in the kits as a package insert or in the labeling of the container of the kit or components thereof. In other embodiments, the instructions are present as an electronic storage data file present on a suitable computer readable storage medium, such as a flash drive. In other embodiments, the actual instructions are not present in the kit, but means for obtaining the instructions from a remote source, such as via the internet, are provided. An example of this embodiment is a kit that includes a web address where the instructions can be viewed and/or from which the instructions can be downloaded. As with the instructions, this means for obtaining the instructions is recorded on a suitable substrate.

Examples

By way of example that is not meant to be exhaustive, BAPT-27 (formula XXVI) was prepared according to Scheme 21 (FIG. 24A) by treating an 4-amino-5-(pyridin-4-yl)-2,4-dihydro-3H-1,2,4-triazole-3-thione with indole-3-carboxaldehyde in acetic acid under reflux conditions (FIG. 24).

By way of example that is not meant to be exhaustive, BAPT-36 (formula XXXII) was prepared according to Scheme 22 (FIG. 24A).

By way of example that is not meant to be exhaustive, BAPT-38 was prepared according to Scheme 23 (FIG. 24A).

By way of example that is not meant to be exhaustive, BAPT-42 was prepared according to Scheme 24 (FIG. 24A).

By way of example that is not meant to be exhaustive, BAPT-44 was prepared according to Scheme 25 (FIG. 24A).

By way of example that is not meant to be exhaustive, BAPT-54 was prepared according to Scheme 26 (FIG. 24B).

By way of example that is not meant to be exhaustive, BAPT-62 was prepared according to Scheme 27 (FIG. 24B).

By way of example that is not meant to be exhaustive, BAPT-82 was prepared according to Scheme 28 (FIG. 24B).

Figure 24C:
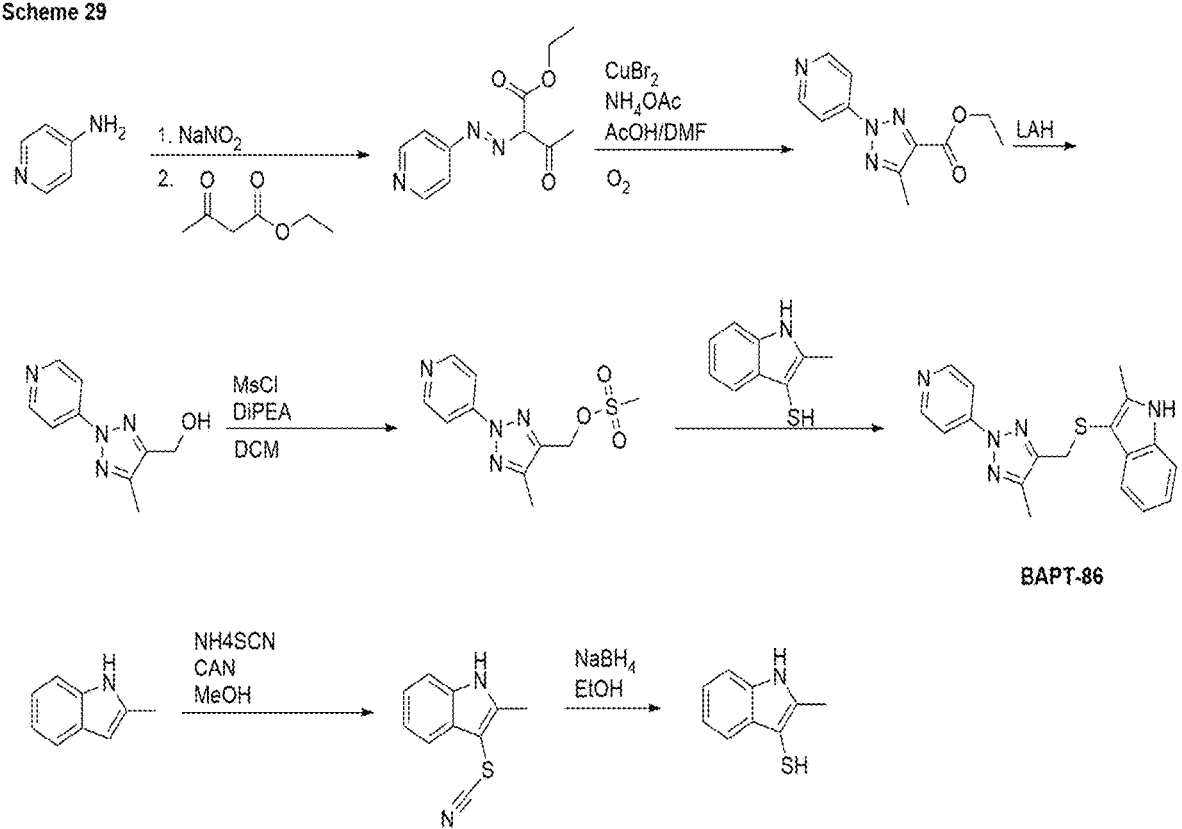
FIG. 24C: Scheme depicting synthesis of scheme 29 (BAPT-86).

By way of example that is not meant to be exhaustive, BAPT-86 was prepared according to Scheme 29 (FIG. 24C).

Test Compounds and Reagents

Compounds BAPT-02 to BAPT-23, BAPT-25 were purchased from Vitas-M Laboratory, Ltd, Champaign, IL 61820, USA. Each of these compounds was stored at −20° C. as a 5 mg/ml stock solution in DMSO, and then diluted to the mentioned final concentration in cell culture medium. All compounds were certified by the vendor to be at least 90% pure with NMR confirmation of structure.

Synthesis and characterization of 4-(((1H-indol-3-yl)methylene)amino)-5-(pyridin-4-yl)-4H-1,2,4-triazole-3-thiol (BAPT-27)

Synthetic Procedure 0.7965 g (4.1 mmol) of 4-amino-5-(4-pyridyl)-4H-1,2,4-triazole-3-thiol, 0.6315 g (4.4 mmol) of indole-3-carboxaldehyde, and 41 mL of glacial acetic acid were consecutively added to a 100 mL round bottom flask with a reflux condenser and a stir bar. The flask was heated in an oil bath up to 115° C. The reaction components gradually formed a clear orange solution which was gently refluxed for 1 hour wherein a solid began to precipitate. The solution was allowed to stir more on heat for 20 minutes and then cooled to room temperature. The solid was collected by vacuum filtration, washed with 20 mL of ice-cold water, and triturated with 125 mL of ethanol. The solid was collected by vacuum filtration and dried under high vacuum for 10 hours to yield 0.567 g (43% yield) of pure product.

M.p. 249-255° C. TLC $R_f$(10% MeOH/90% EtOAc) =0.15. $^1$H NMR (DMSO, 400 mHz): δppm: 14.35 (1H, s), 12.15 (1H, s), 9.44 (1H, s), 8.73-8.71 (2H, d, J=5.60), 8.20 (1H, s), 8.10-8.08 (1H, d, J=8.00), 7.96-7.95 (2H, d, J=6.00), 7.55-7.53 (1H, d, J=8.00), 7.30-7.20 (2H, m). $^{13}$C NMR (DMSO, 150 mHz): δppm: 164.9, 163.6, 150.7, 146.6, 137.9, 136.5, 133.5, 124.8, 123.9, 122.3, 122.1, 113.0, 110.2. Anal. Calcd for $C_{16}H_{12}N_6S$: C, 59.98; H, 3.78; N, 26.23. Found: C, 60.02; H, 3.78; N, 26.33.

Biological Evaluation of BAPT Derivatives

BAPT-27 induces the rapid accumulation of extensive fluid filled-cytoplasmic vacuoles in colon, pancreatic, ovarian, lung, and prostate cancer cell lines. The vacuoles are originated from macropinocytosomes as confirmed by extracellular fluid phase tracers. Vacuolization has been described previously as methuosis. However, the vacuoles induced here combine the characteristics of methuosis, autophagy, enhanced lysosomal activity, and other distinct characteristics.

Cells treated with BAPT-27 lose their viability within 72 h. The mechanisms of death involve non-apoptotic cell death where the cells' nuclei show no apoptotic changes (no chromatin condensation or DNA fragmentation). Through electron microscopy there were clearly no signs of apoptosis (i.e., cell shrinkage, nuclear condensation, blebbing) seen. Only one in 100 cells were observed to have died through apoptosis at a very high concentration, which is non-significant. The annexin fluorescence was not changed upon treatment with BAPT-27, and the inhibition of caspase activity by pan-caspase inhibitor z-VAD-fmk did not protect the cells from death, which further confirmed non-apoptotic cell death mechanisms.

BAPT-27 reversed multidrug resistance in resistant colon cancer cell lines S1M180, as well as resistant lung cancer cell lines H460-MX20. The cells became sensitive to the cytotoxicity of mitoxantrone when combined with BAPT-27. Further, BAPT-27 induced death in apoptosis resistant cell lines including colon cancer cell lines that are missing important pro-apoptotic genes Bax and Bak using well established models (HCT116, HCT116 Bax −/−, HCT116 Bak −/−, HCT116 Bax/Bak−/−). Accordingly, BAPT-27 represents a family of compounds that induce cell death in sensitive and resistant cancers, as well as those cancers that are refractory to death by conventional apoptosis inducing anticancer agents.

BAPT-27 induces a type of death that is also independent of necrosis or necroptosis. The vacuoles formation and cell death was not inhibited by the addition of necrostatin-1, a necroptosis inhibitor, even at high concentrations (up to 30 μM).

BAPT-27 induced vacuoles that combine both methuosis and autophagy characteristics. The vacuoles showed accumulation of acridine orange, indicating activated acidic compartments. BAPT-27 also induced the cleavage of LC3B and the formation of LC3B loci at the borders of the vacuoles, indicating alteration in the autophagic signaling pathways. At the same time, treatment with autophagy inhibitors including 3-MA (early autophagy inhibitor) and chloroquine (late autophagy inhibitor) did not inhibit the vacuoles formation or cytotoxic effects of BAPT-27. Such results indicate the altering of autophagy is part of BAPT-27 mechanisms but not the only mechanism involved. The author mechanism involved in this non-conventional cell death mechanism is a special type of micropinocytosis that has been termed methuosis. The treatment of cells by BAPT-27 caused the displacement of the cytoplasm by vacuoles derived from macropinosomes. At early time points, the vacuoles are small in size. The small vacuoles then increase in number, and then fuse with each other over time forming larger vacuoles that cover the whole cytoplasm. Eventually, this causes a disturbance of the cell membrane and burst of the cells, release of fluids, detachment of cell, and death. The vacuoles showed the accumulation of Lucifer yellow dye, which further confirms the presence of macropinosomes-derived methuosis. Accordingly, alteration in both autophagic and methuosis mechanisms are involved in the BAPT-27 cell death process.

The small molecule BAPT-27 produced methuophagy induced cell death where small fluid-vacuoles were observed to be formed in the time line studies in different types of cancer cell lines (colon, lung, ovarian, pancreatic, and prostate) as well as resistant cancer cell lines that are multidrug-resistant cell lines overexpressing ABC efflux transporters, and apoptosis-resistant cell lines lacking some important proapoptotic genes (Bax, Bak, or both).

Figure 25:
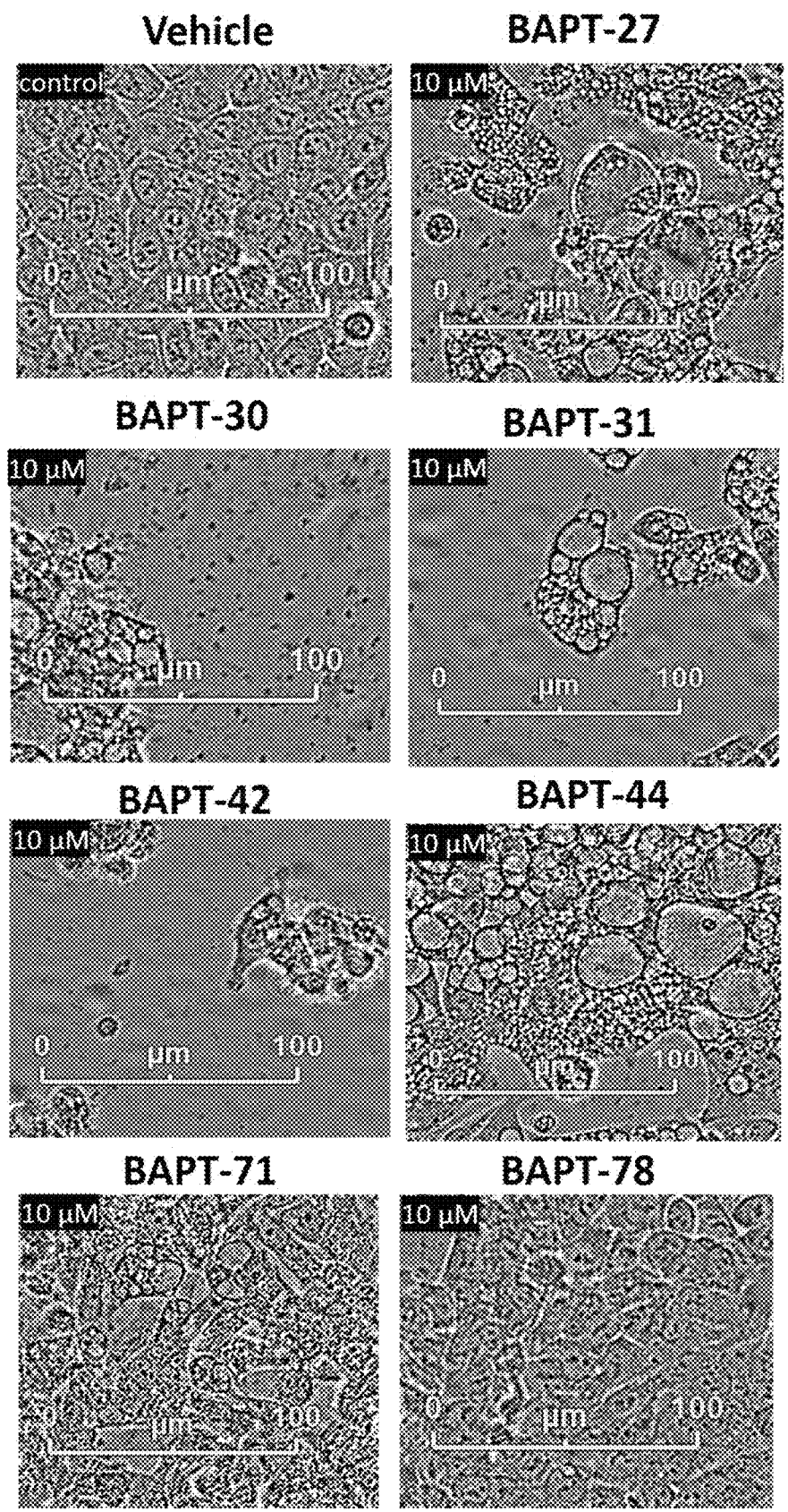
FIG. 25: Morphological assessment of BAPT Derivatives induced vacuolization in HCT-116 colon cancer cells.
Figure 25:
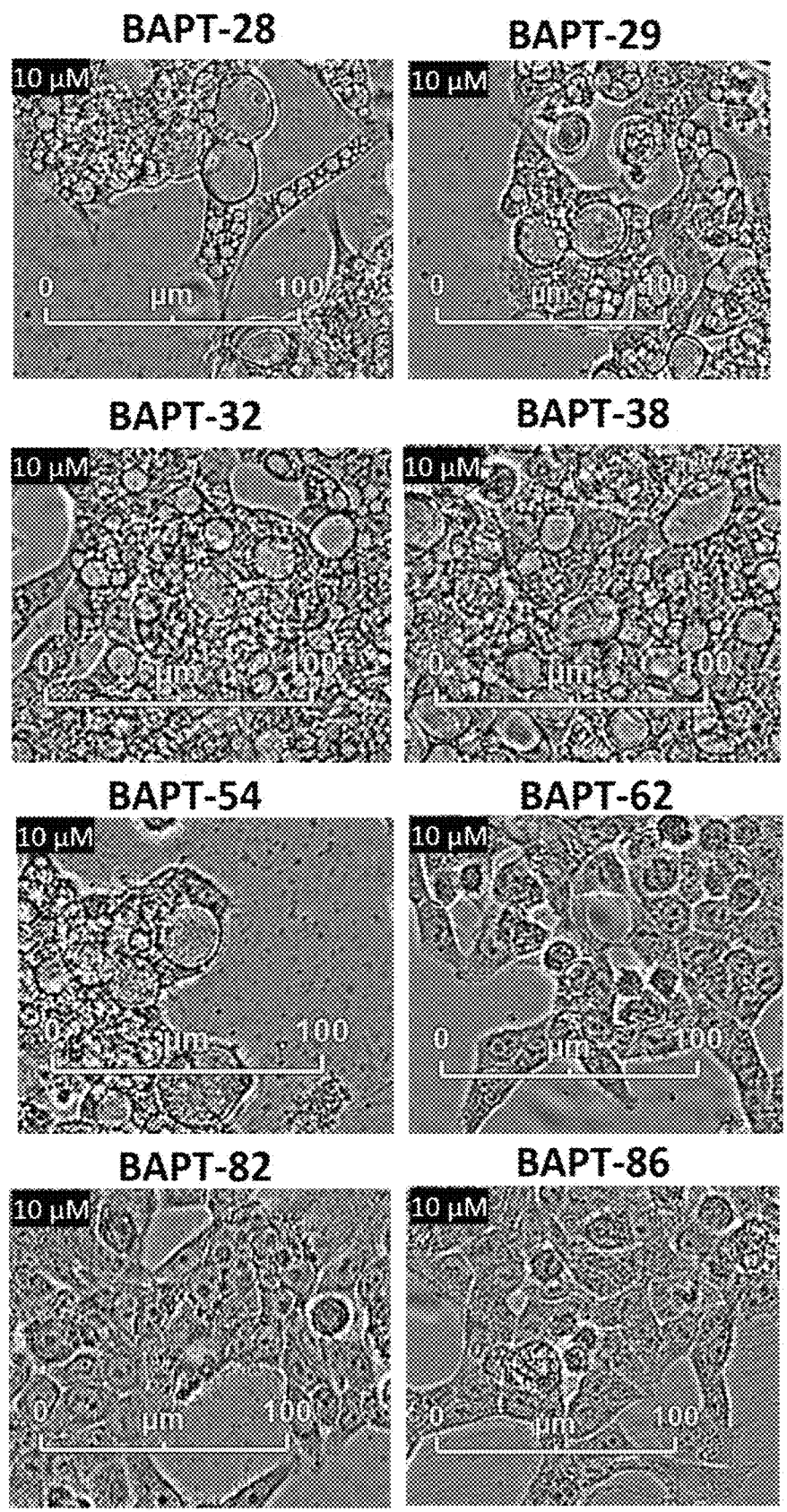
Figure 26:
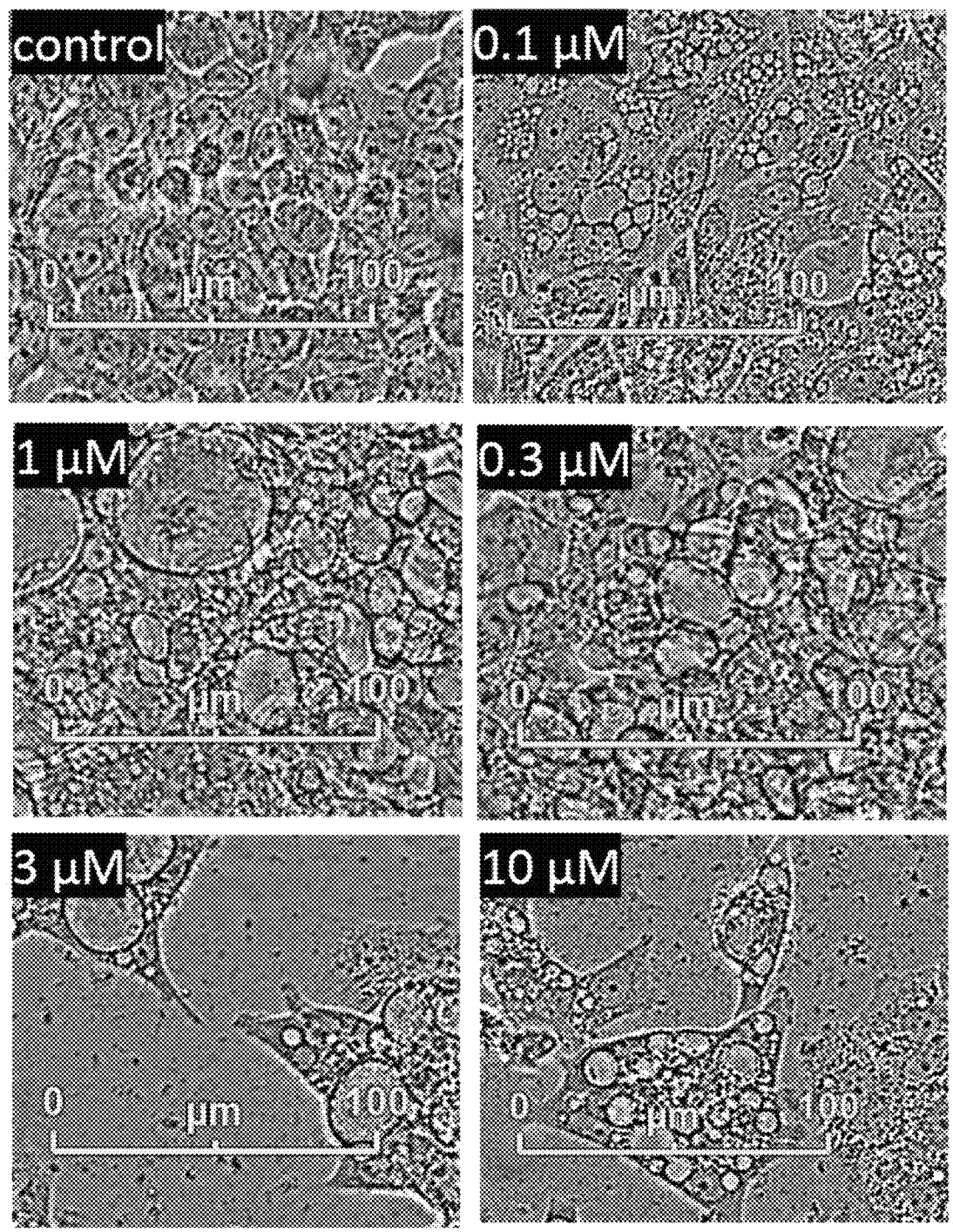
FIG. 26: Morphological assessment of dose dependent vacuolization induced by BAPT-36 in HCT-116, BT-20 (triple negative breast cancer) and U-251 (glioblastoma) cells.
Figure 26:
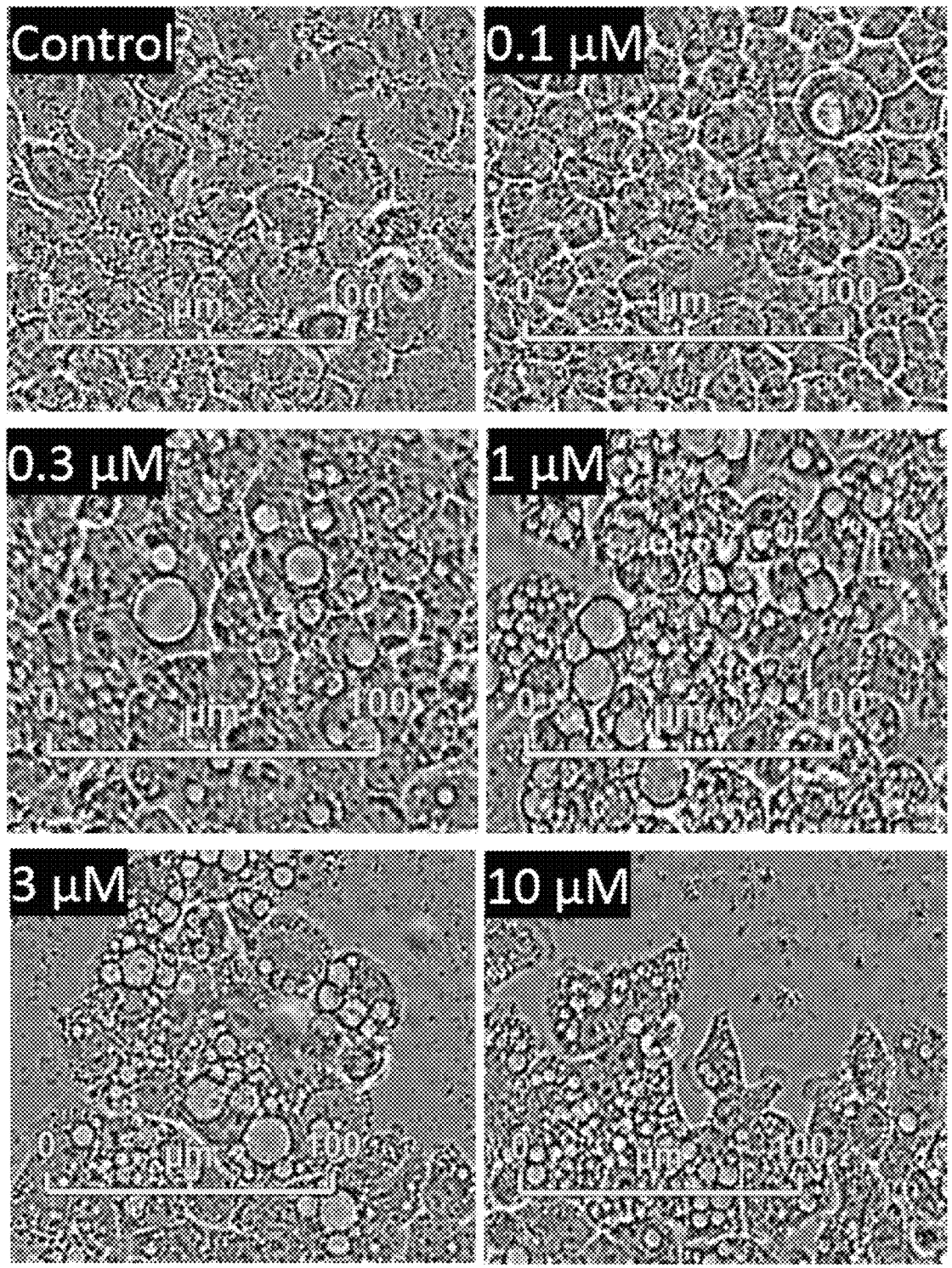
Figure 26:
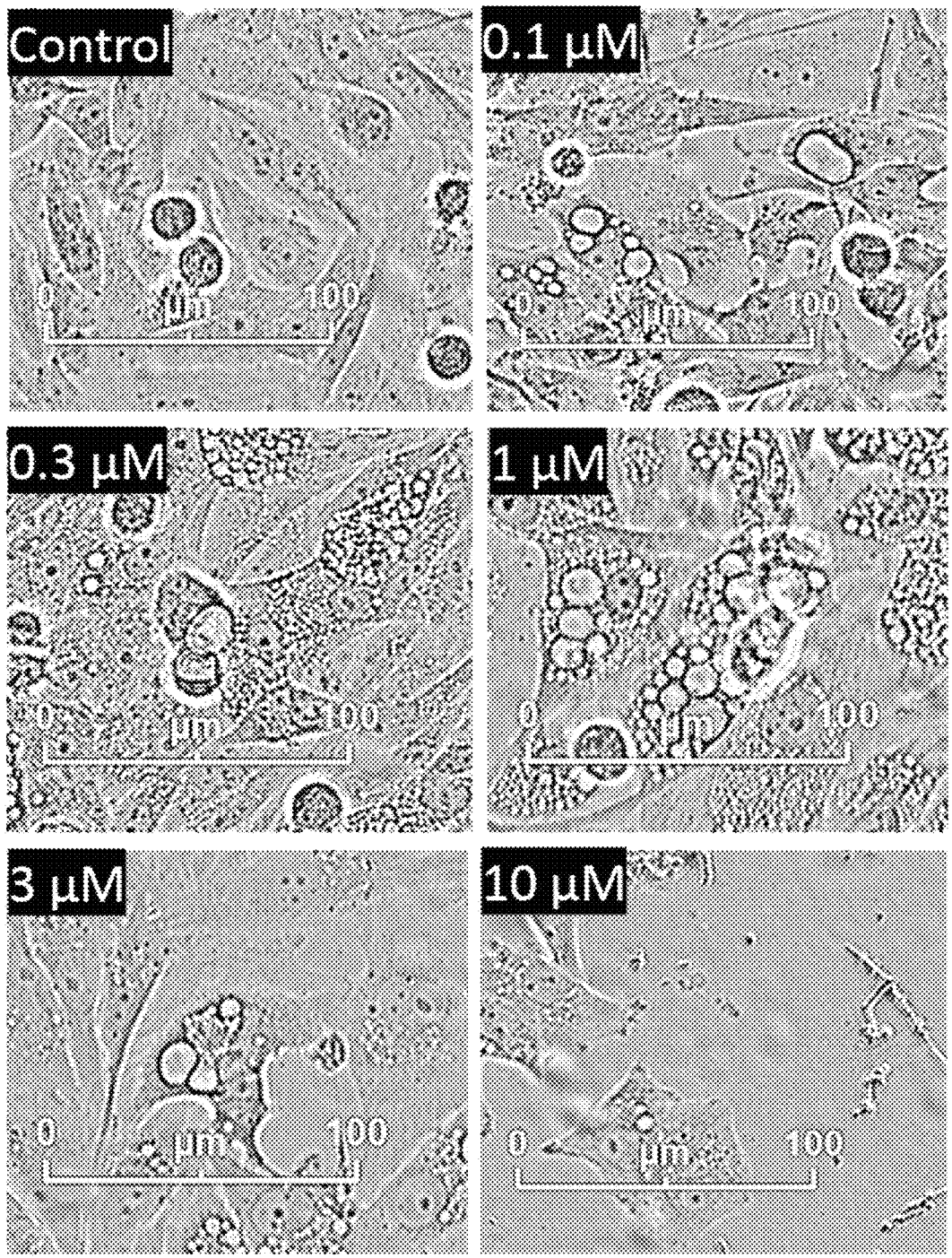
Figure 27:
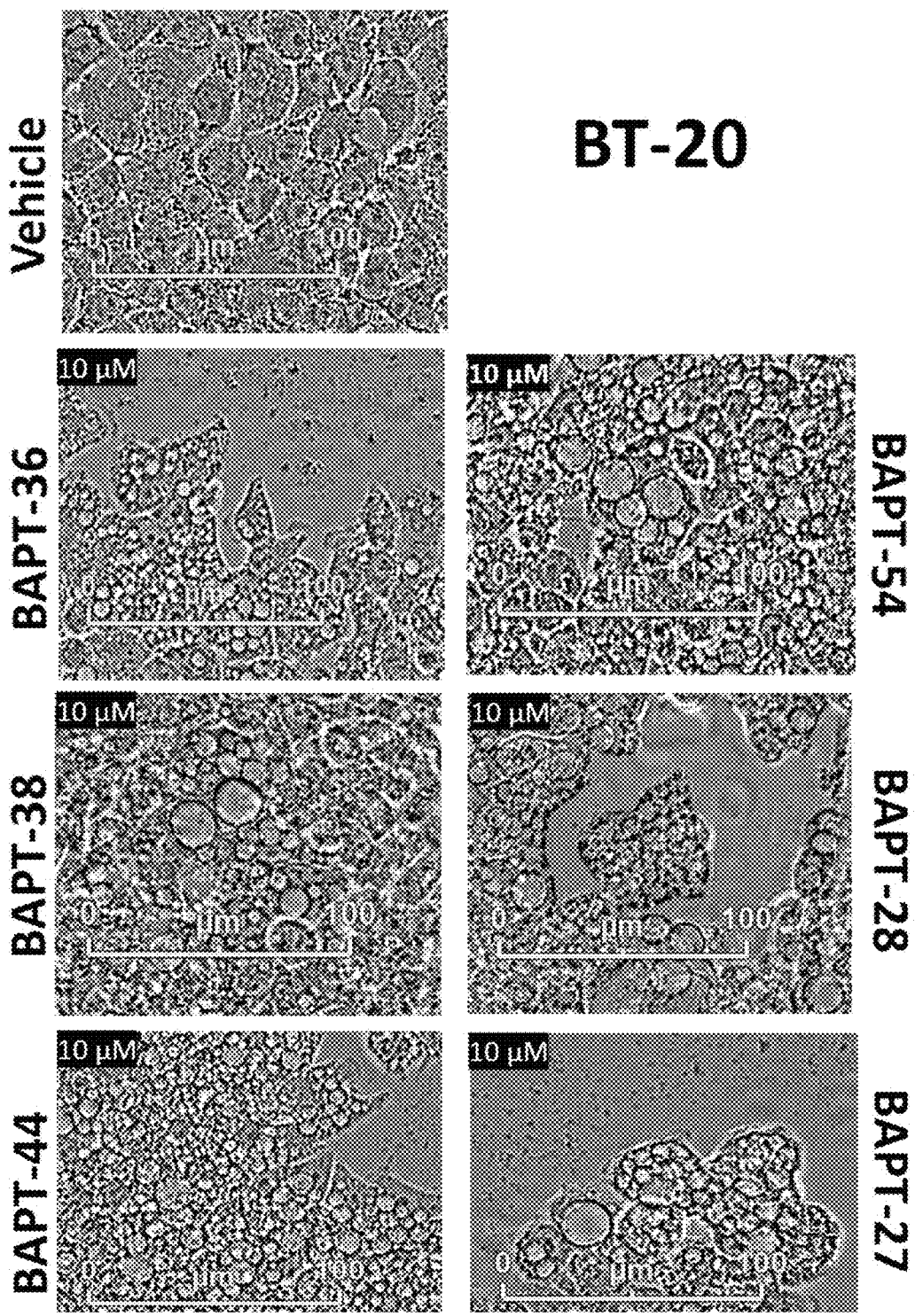
FIG. 27: Morphological assessment of BAPT Derivatives induced vacuolization in BT-20 and U-251 cells.
Figure 27:
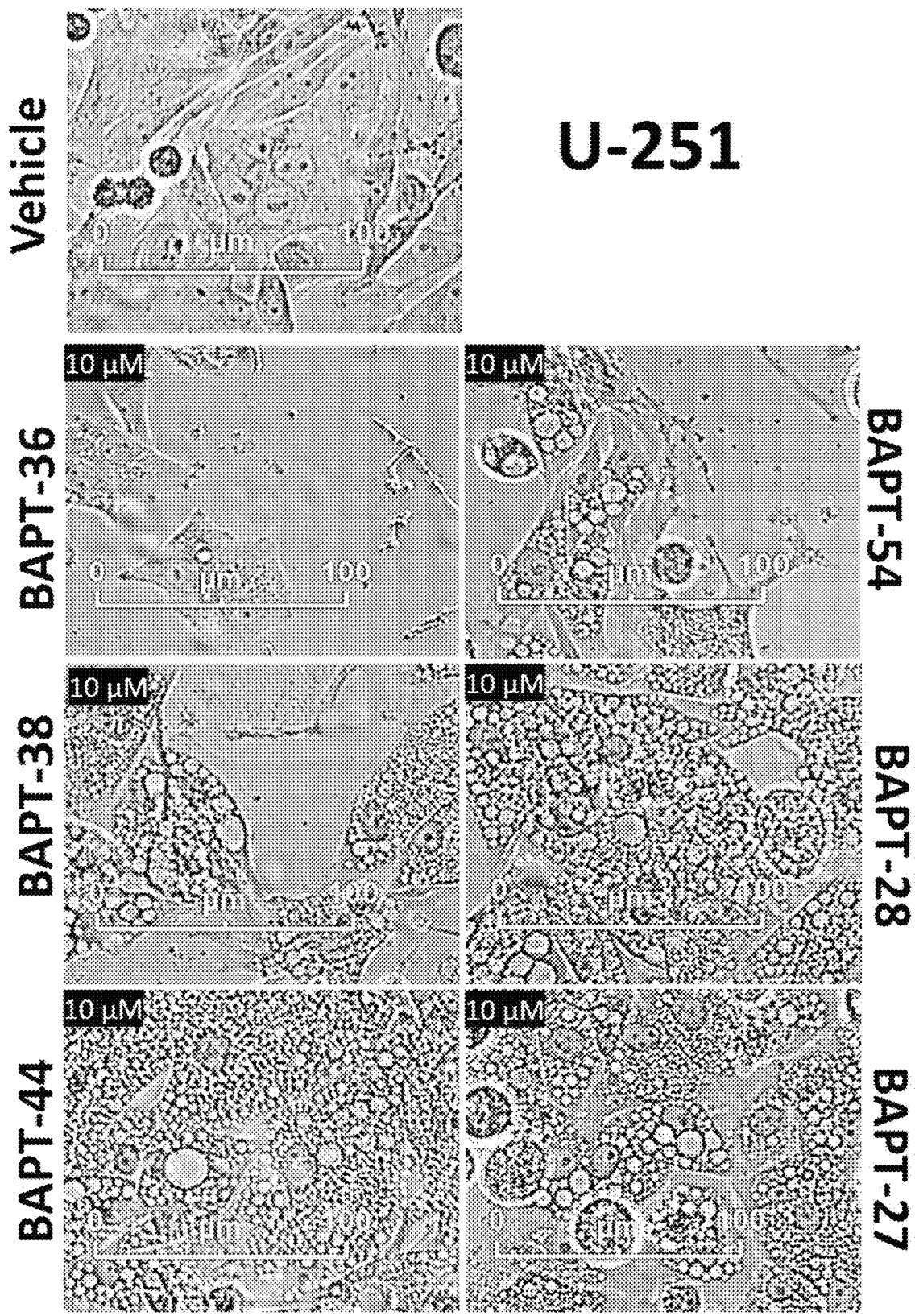

The morphological assessment of HCT-116 (colon cancer), BT-20 (triple negative breast cancer) and U-251 (glioblastoma) cells treated with BAPT derivatives showed extreme vacuolization (FIGS. 25-27).

Figure 28A:
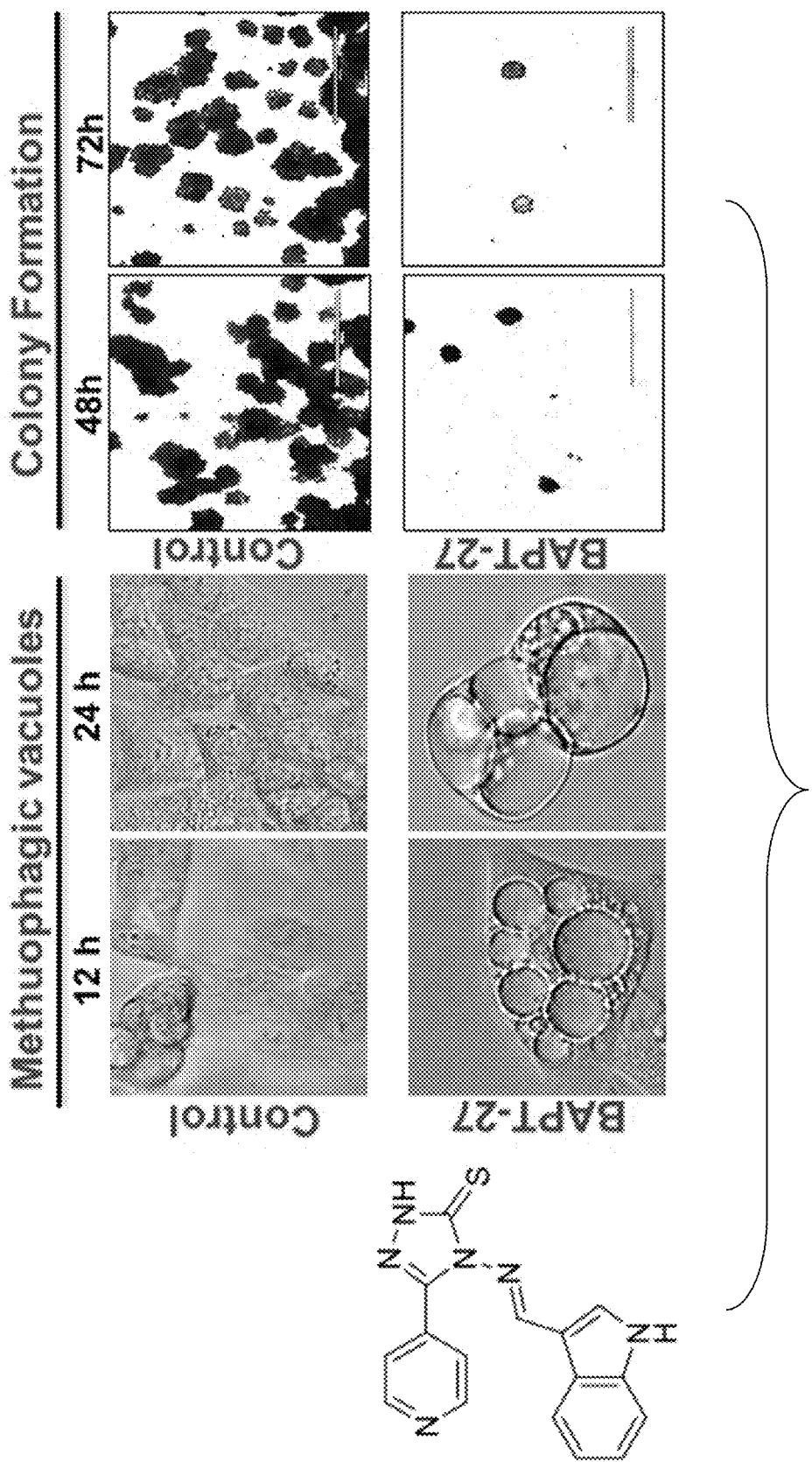
FIG. 28A: Colony formation assay of BAPT-27 in the long-term capacity of the compound to inhibit cell proliferation and viability. The formation of methuophagic vacuoles at 12 h and 24 h are shown. In addition, the cells were treated for 2 or 3 days and allowed to grow in compound free medium for up to two weeks. BAPT-27 significantly inhibited colony formation at two and three day's treatment. It was also observed that a higher concentration was needed to reduce the colony formation at 48 h compared to longer treatment (72 h).

The cytotoxic efficacy of BAPT-27 was also confirmed by colony formation assay. Colony formation assay was used to determine the long-term capacities of the compound to inhibit cell proliferation and viability. The cells were treated for 2 or 3 days and allowed to grow in compound free medium for up to two weeks. BAPT-27 significantly inhibited colony formation at two and three days treatments (FIG. 28A). It was also observed that a higher concentration of BAPT-27 was needed to reduce the colony formation at 48 h compared to longer treatment (72 h). (FIG. 28A).

Figure 28B:
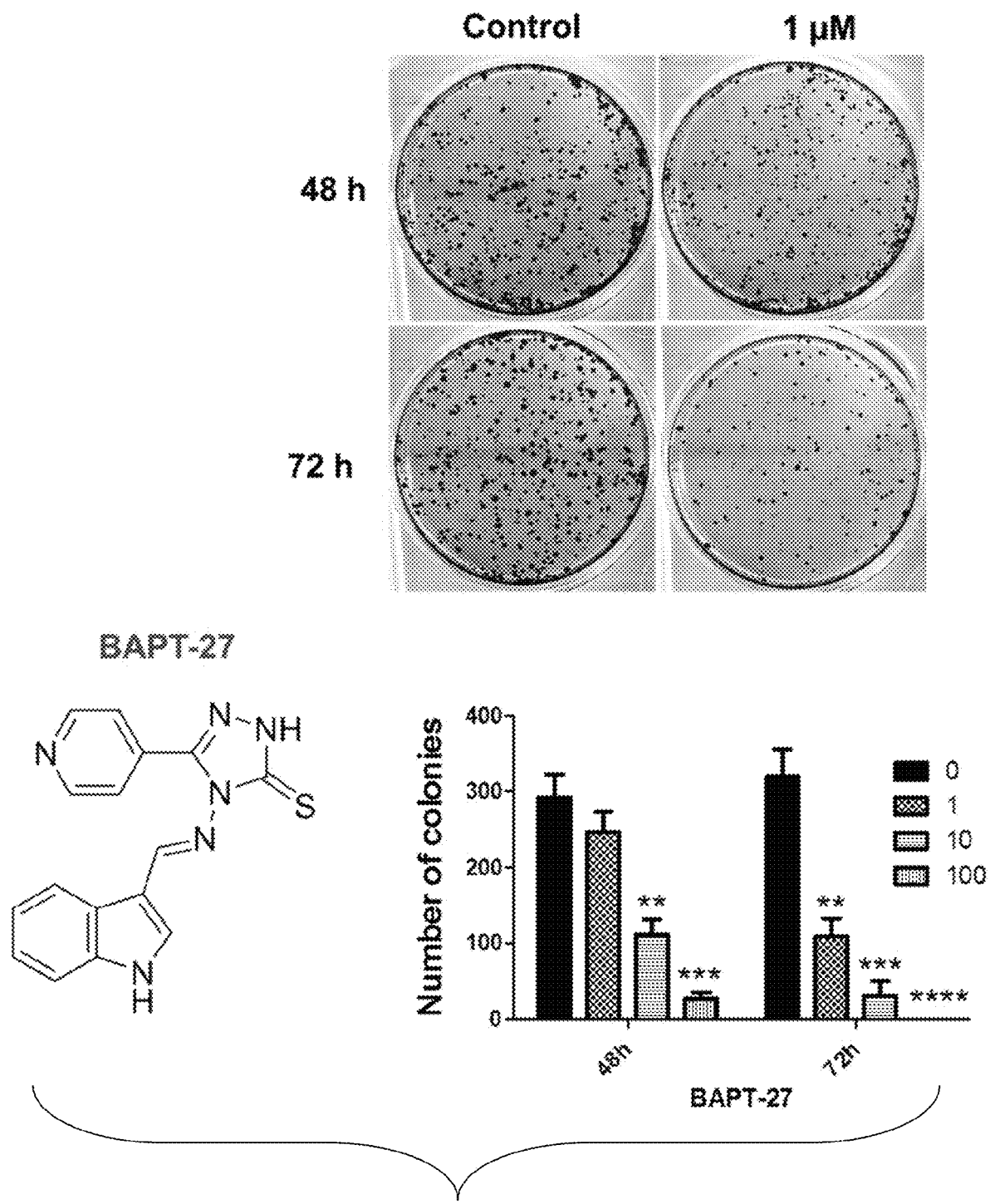
FIG. 28B: BAPT-27 colony formation assay at 48 and 72 h in HCT116 colon cancer cells. The cells were treated for 2 or 3 days and allowed to grow in compound free medium for up to two weeks. BAPT-27 produced significant inhibition in the colonies number and size, especially after 72 h treatment. The number of colonies formed/concentration is shown in the bar graph at each time point.

FIG. 28B shows a BAPT-27 colony formation assay at 48 h and 72 h in HCT116 colon cancer cells. The cells were treated for 2 or 3 days and allowed to grow in compound free medium for up to two weeks. BAPT-27 produced significant inhibition in the colonies number and size especially after 72 h treatment. The number of colonies formed/concentration at each time point is shown in the bar graph in FIG. 28B.

Figure 29:
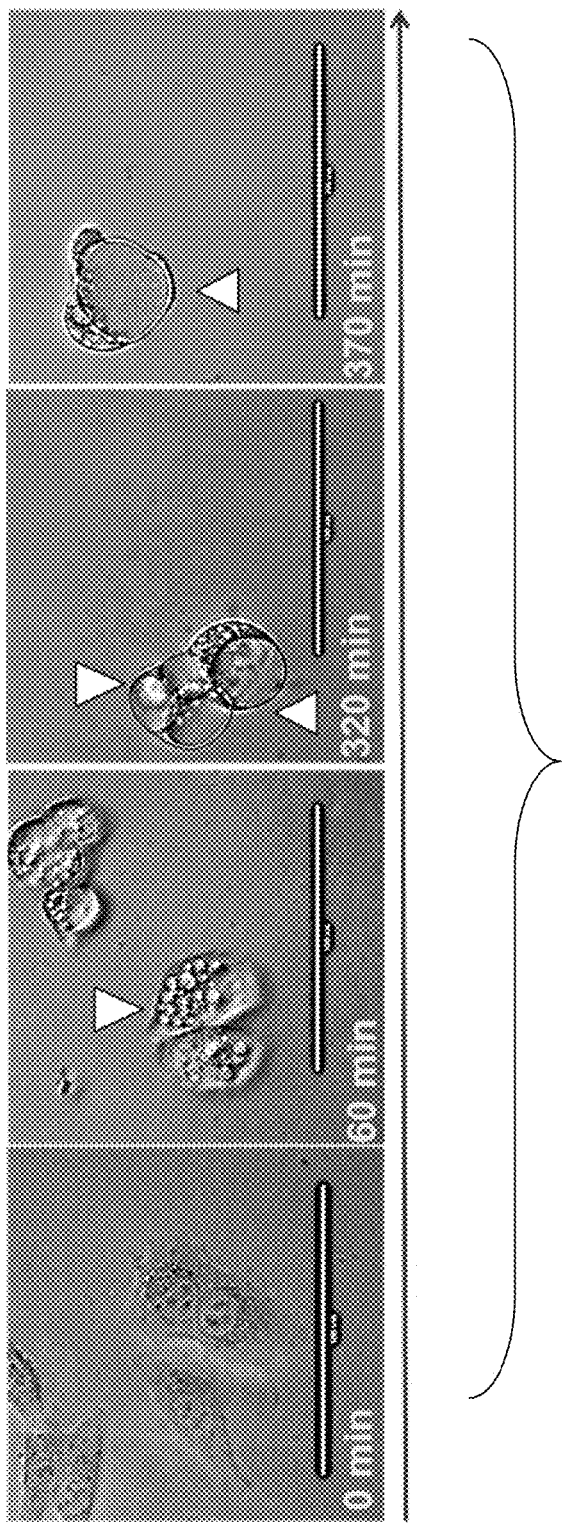
FIG. 29: Images showing the vacuoles generated by BAPT-27 (10 μM) are formed by macropinocytosis as small fluid-filled, heterogeneous, single-membrane vacuoles that undergo fusion events with time producing larger vacuoles. The white arrows are indicating to the vacuoles that fused over different time points.
Figure 30:
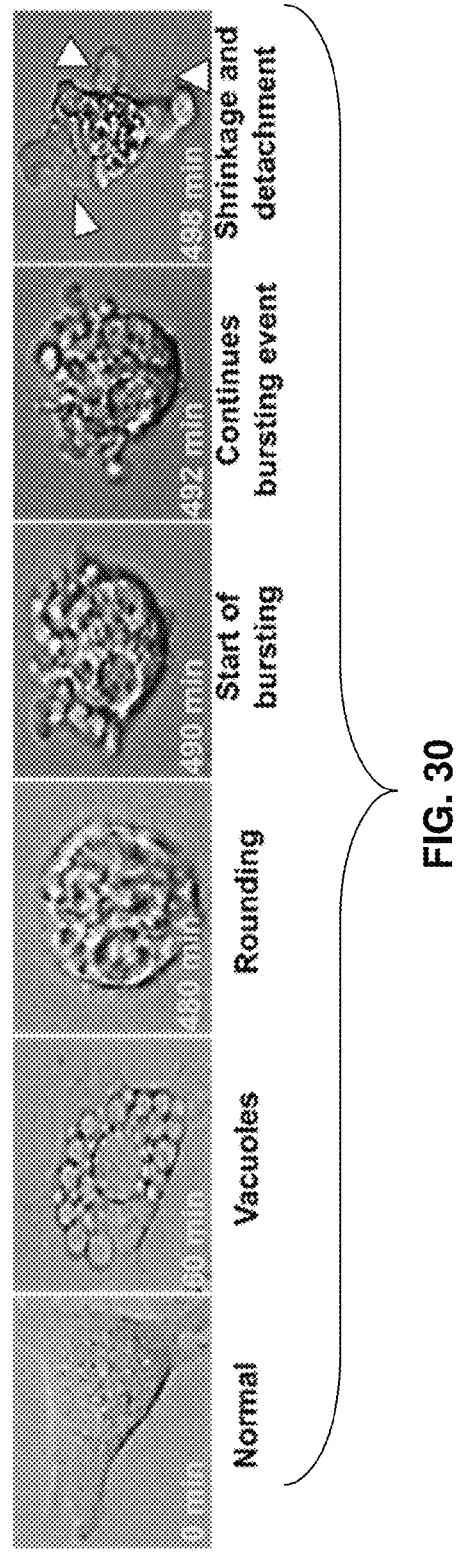
FIG. 30: Images showing the large vacuoles eventually force the cells to enter in the stage of death events. The vacuoles disturb the cell membrane integrity; accordingly, the cells will burst releasing all the cellular fluids and contents, shrink, detach, and commit death.

The vacuoles generated by BAPT-27 (10 μM) were formed by macropinocytosis as small fluid-filled, heterogeneous, single-membrane vacuoles that undergo fusion events with time producing larger vacuoles. The white arrows in FIG. 29 point to the vacuoles that fused over different time points. There is an accumulation of heterogeneous vacuoles of different sizes that are initially small in number and size. Then, the vacuoles merge with time to produce larger fluid filled vacuoles (FIG. 29). The large vacuoles eventually force the cells to enter in the stage of death events. The vacuoles disturb the cell membrane integrity; accordingly, the cells will burst, releasing all the cellular fluids and contents, shrink, detach, and commit death. (FIG. 30).

Figure 31:
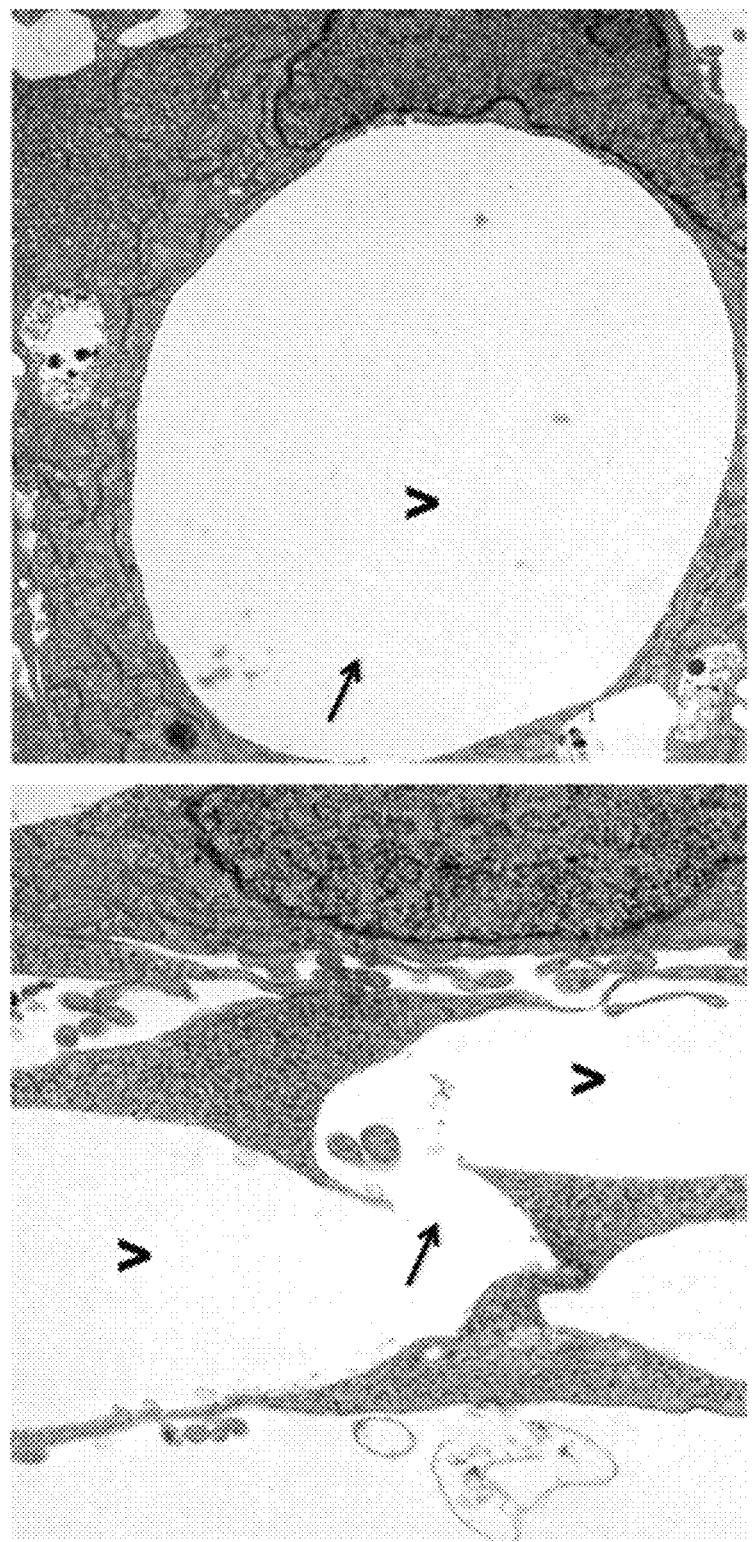
FIG. 31: Electron microscopy showing the vacuole fusion events. The vacuoles are indicated by V, and the destruction of the single membranes of the vacuoles is indicated by arrows.
Figure 31:
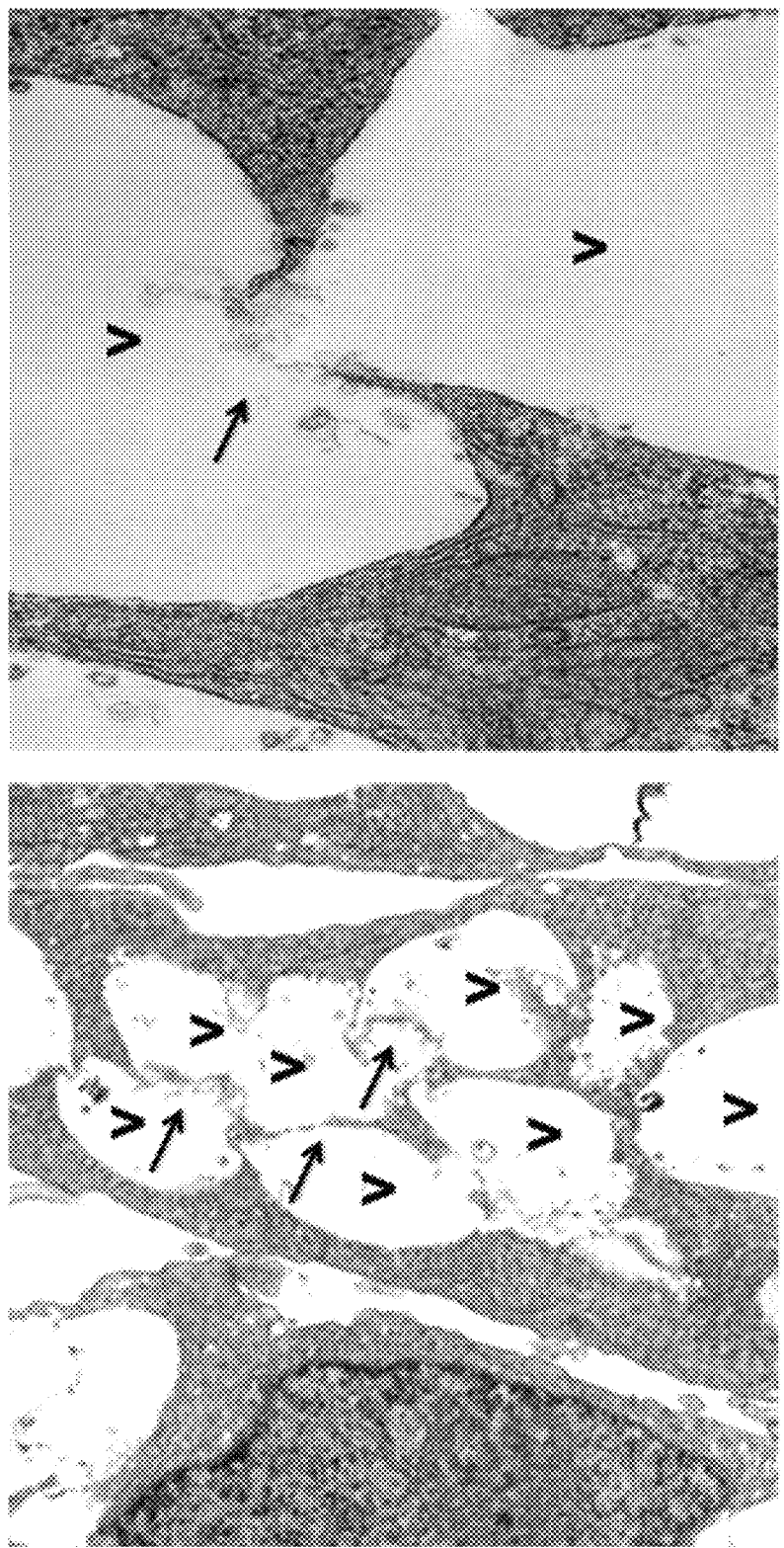

As seen in FIG. 31, electron microscopy showed the vacuole fusion events. The vacuoles are indicated by V in FIG. 31. The single membranes of the vacuoles are destroyed (indicated by arrows in FIG. 31), allowing small vacuoles to merge, forming bigger vacuoles. However, the nucleus is healthy and shows no change, indicating a nonapoptotic process.

Figure 32:
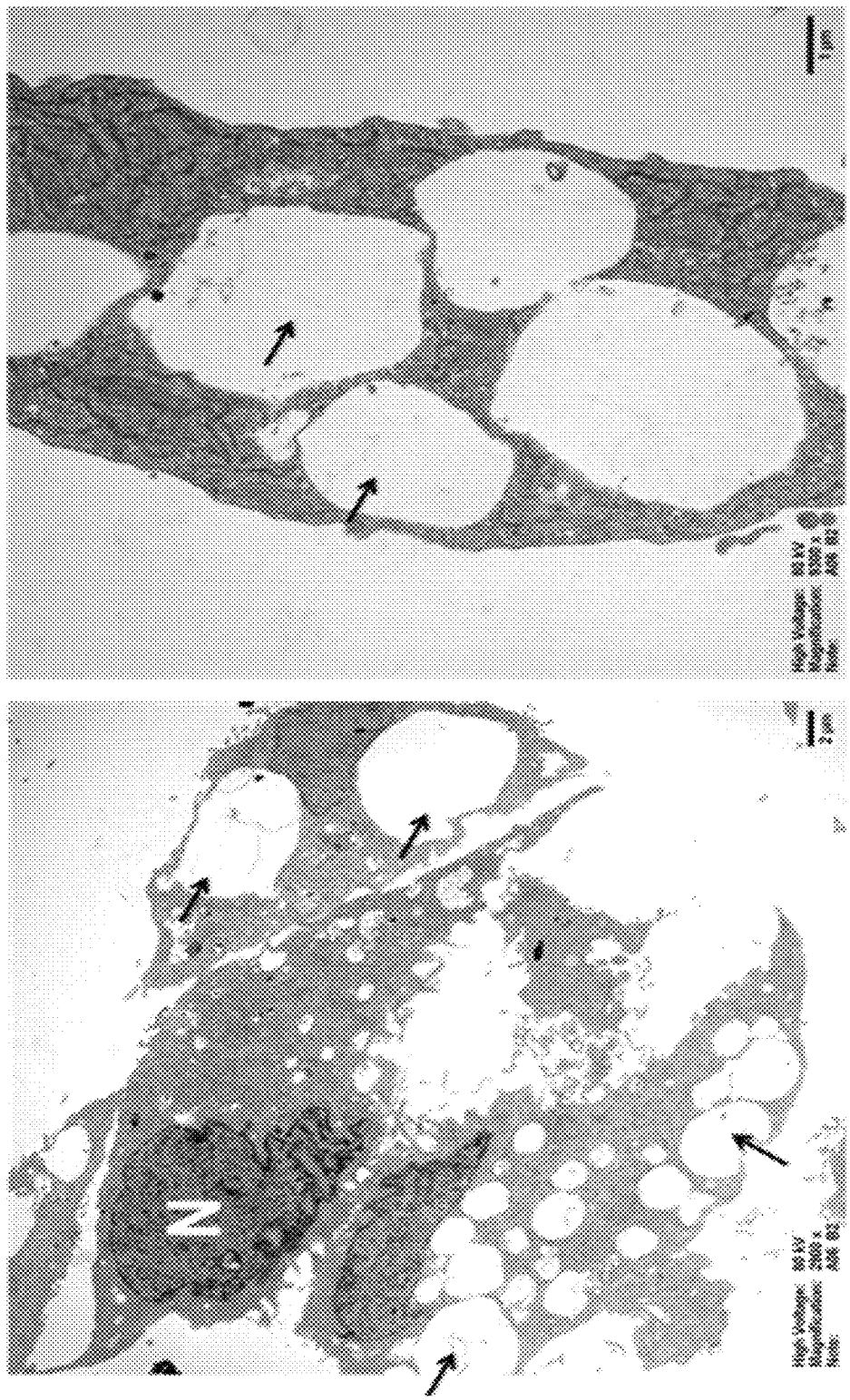
FIG. 32: Electron microscopy images of HCT116 cells showing extensive formation of single membrane vacuoles at 10 μM of BAPT-27. The nuclei are indicated by white N, and the vacuoles are indicated by black arrows.
Figure 32:
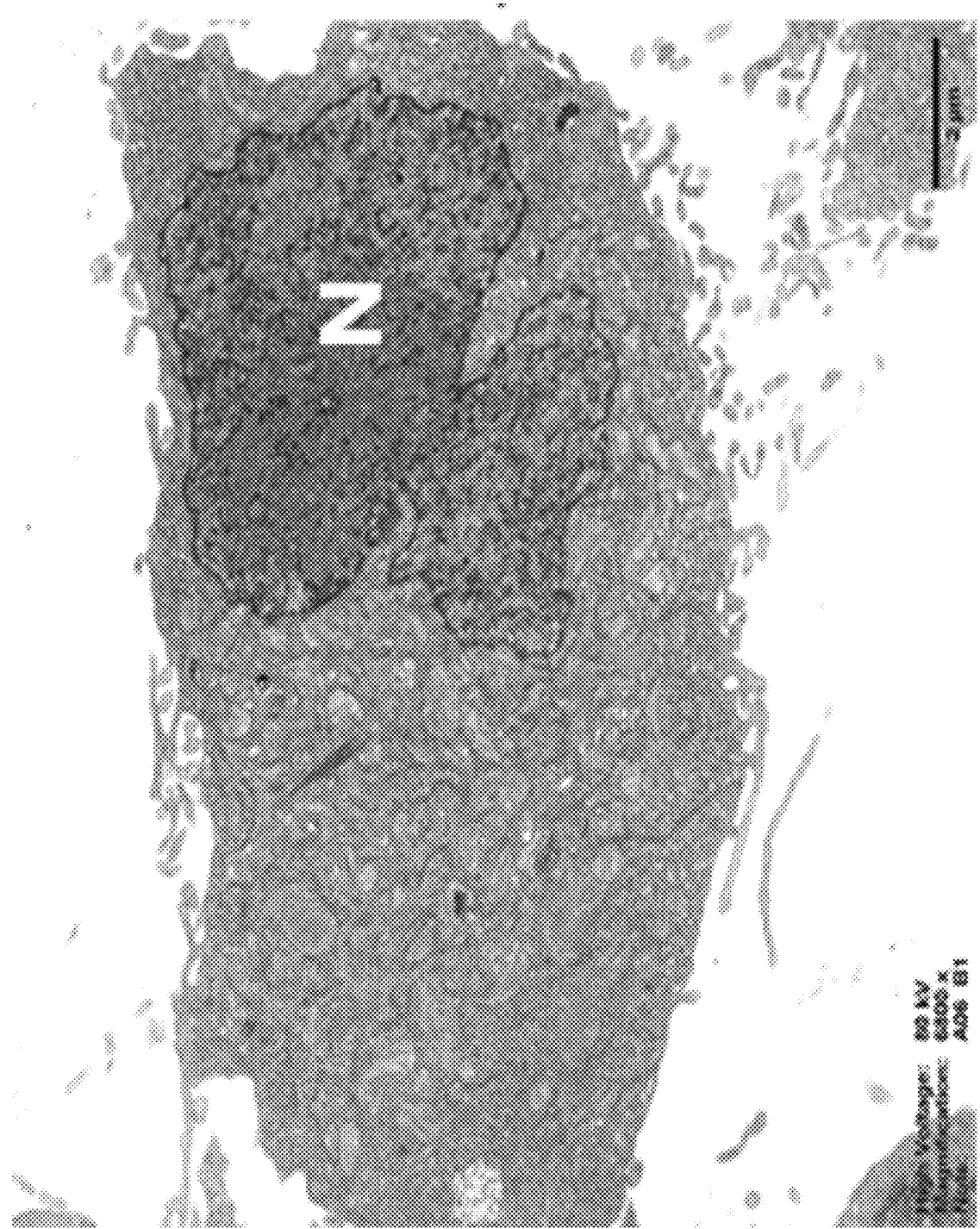

Electron microscopy of HCT116 cells showed extensive formation of single membrane vacuoles at 10 μM of BAPT-27 (FIG. 32). The vacuoles are fluid filled with traces of membranes due to vacuoles fusion events. The nuclei are healthy with no signs of chromatin condensation and are unaffected at even a high concentration (30 μM). However, as the vacuoles coalesce and grow in size, the nuclei are pushed on the edges of the cells. The nuclei are indicated by white N, and the vacuoles are indicated by black arrows, in FIG. 32.

Figure 33:
FIG. 33: Electron microscopy showing the macropinosomes formation and how vacuoles are originated from macropinosomes.

FIG. 33 shows an electron microscopy image showing the macropinosomes formation and how vacuoles are originated from macropinosomes.

Figure 34:
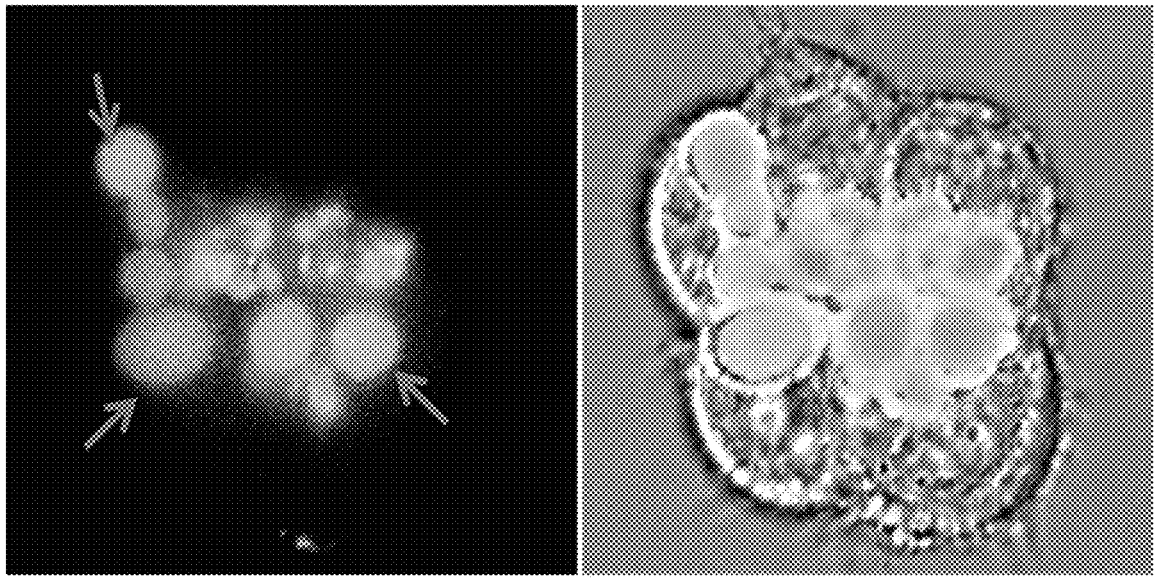
FIG. 34: Extensive accumulation of Lucifer yellow dye was detected in the formed vacuoles from BAPT-27 (10 μM) after 6 h treatment indicating active micropinocytosis.

Extensive accumulation of Lucifer yellow dye was detected in the formed vacuoles from BAPT-27 (10 μM) after 6 h treatment, indicating active micropinocytosis (FIG. 34).

Figure 35A:
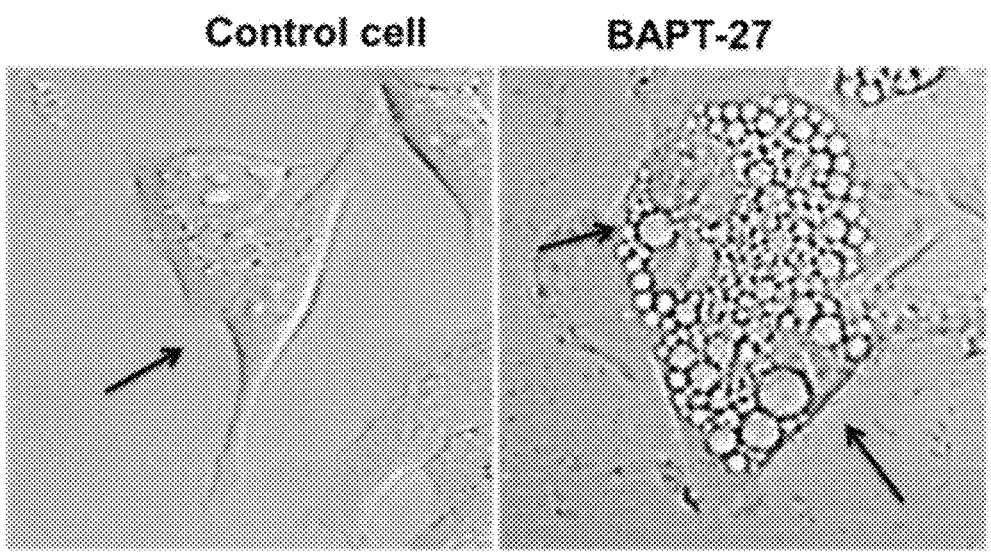
FIGS. 35A-35D: BAPT-27 induces cell death by nonapoptotic cell death mechanisms.
Figure 35B:
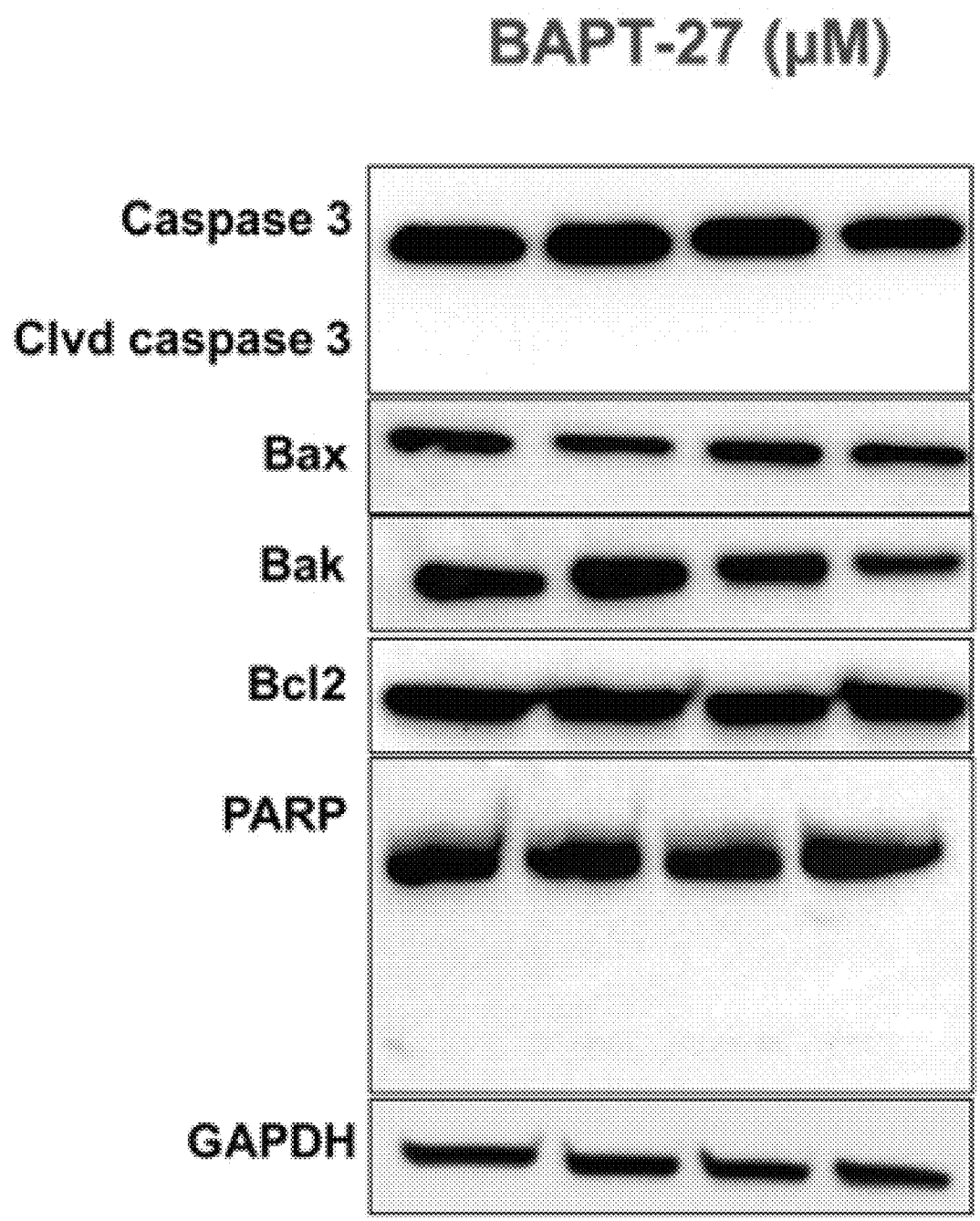
Figure 35C:
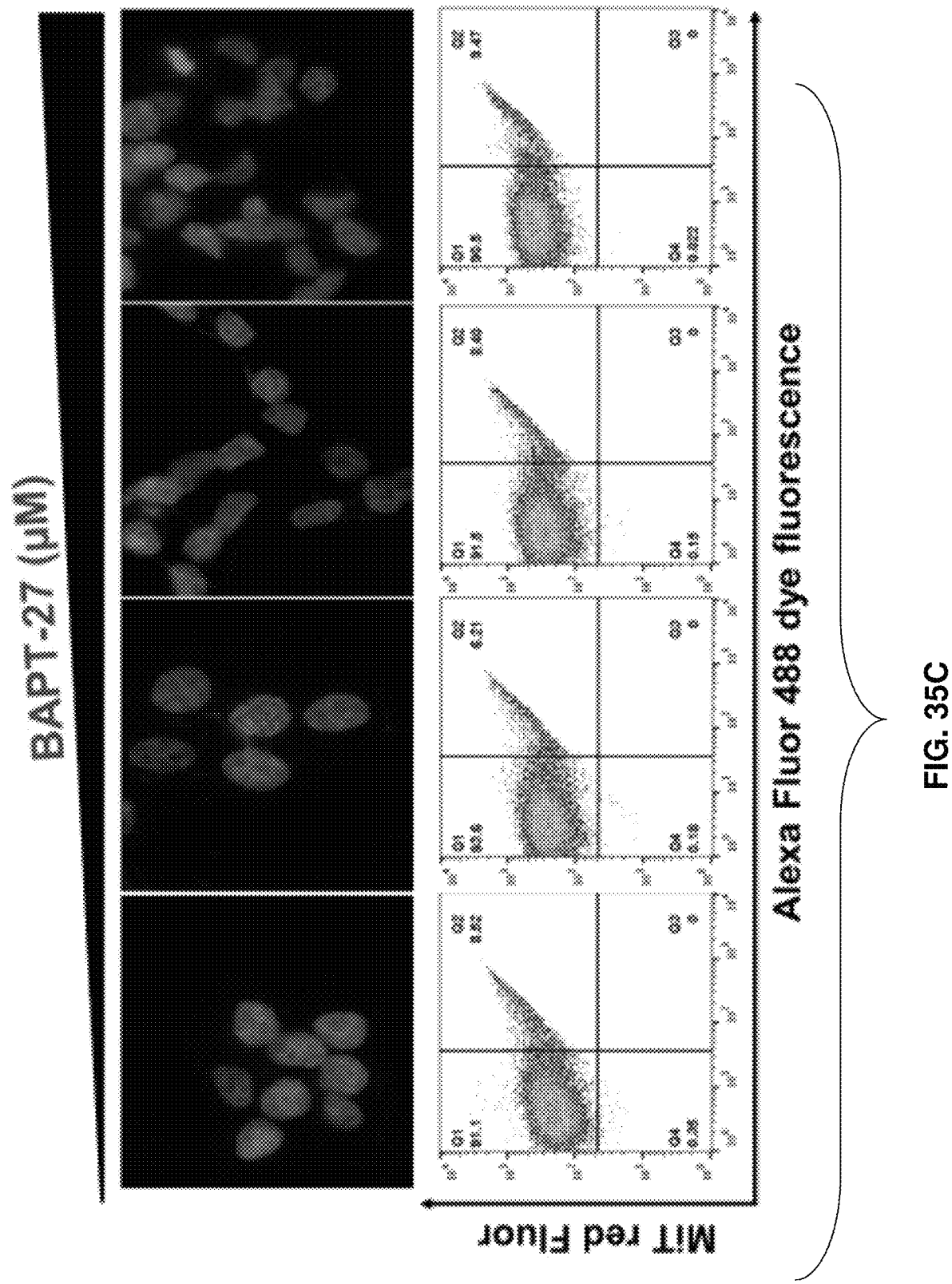
Figure 35D:
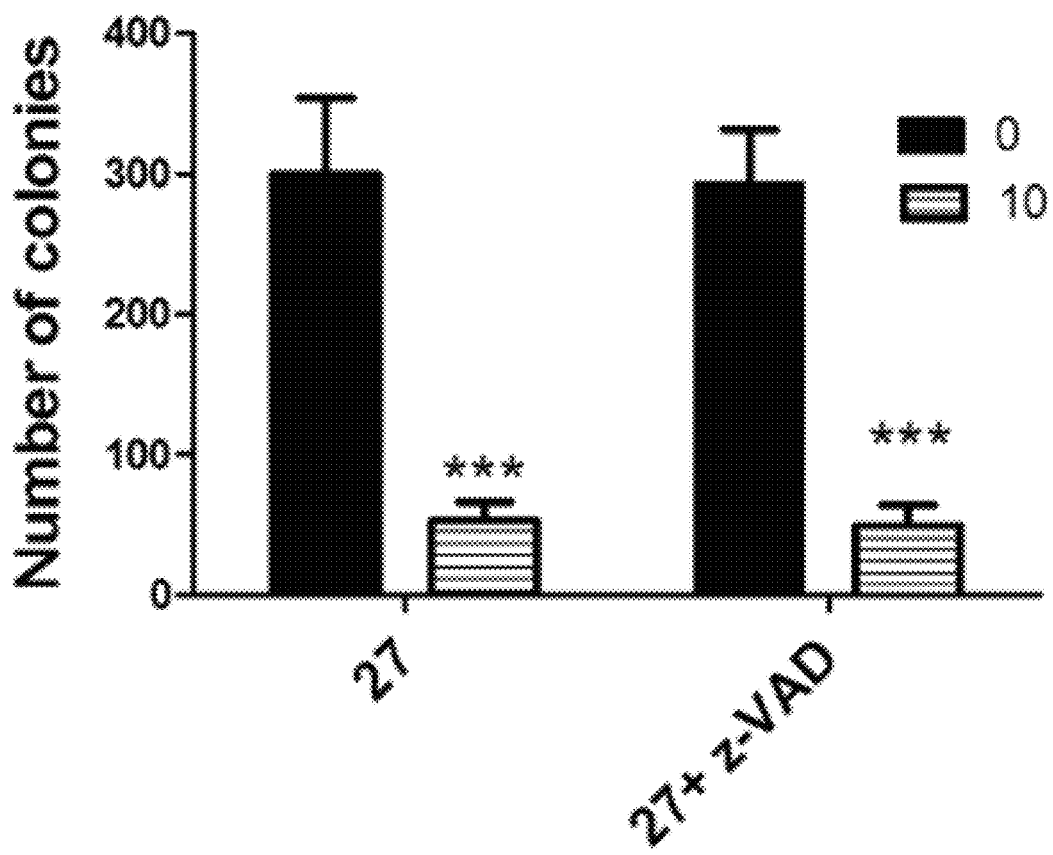

BAPT-27 induces cell death by nonapoptotic cell death mechanisms where cells show vacuoles accumulation, cell expansion, and no shrinkage (FIG. 35A), the BAPT-27 produces no alteration in the intrinsic apoptoic pathways (no activation of proapotic proteins and no inhibition of antiapoptotic proteins) (FIG. 35B), and the nuclei show no apoptotic changes (no chromatin condensation or DNA fragmentation) (FIG. 35C). The annexin fluorescence was not changed upon treatment with BAPT-27 (FIG. 35D), and the inhibition of caspase activity by z-VAD-fmk (pan-caspase inhibitor) did not protect the cells from death, which further confirmed nonapoptotic cell death mechanisms.

Figure 36:
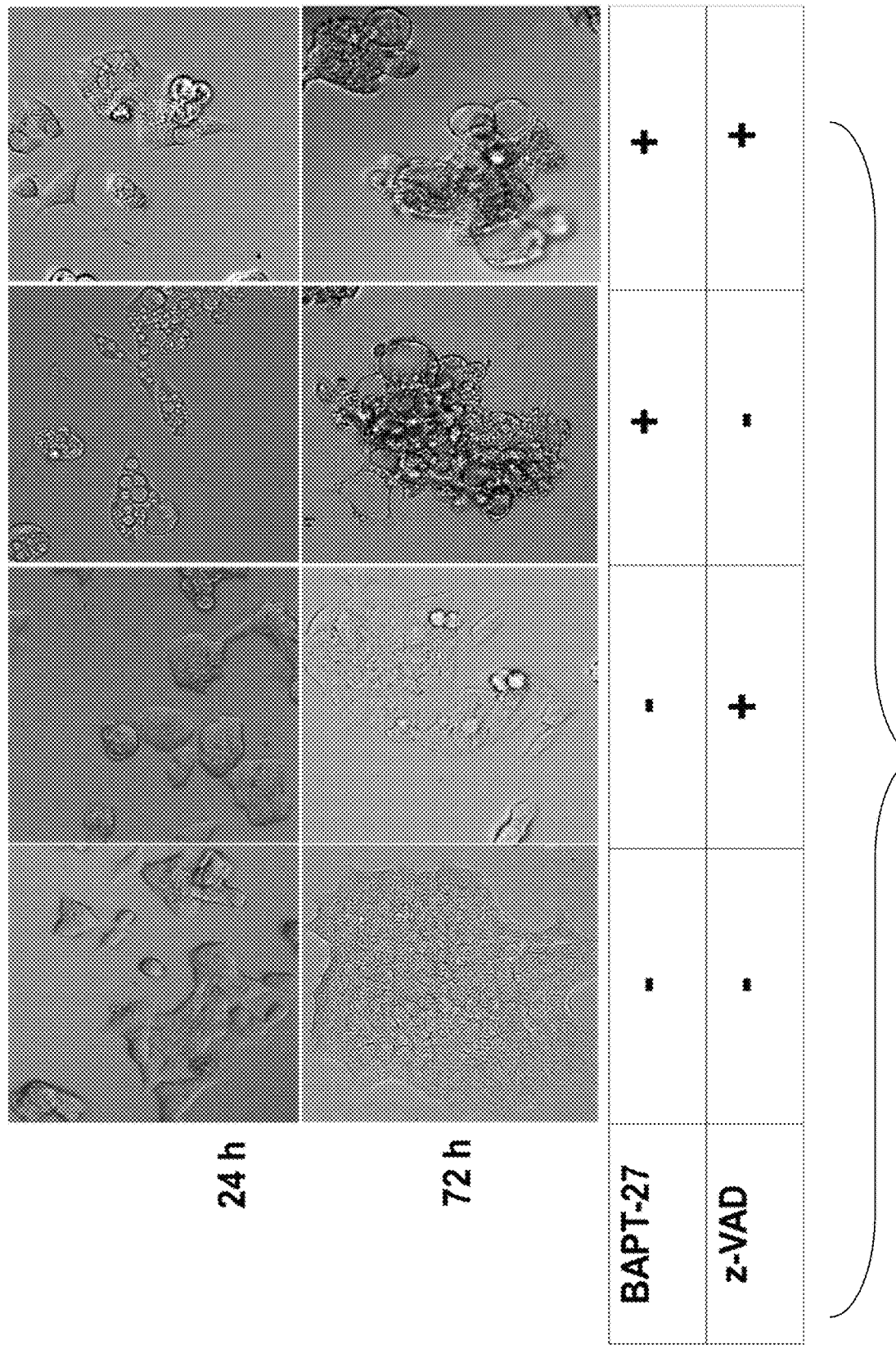
FIG. 36: The z-VAD (100 μM) does not block the formation of vacuoles generated by BAPT-27 (10 μM) at 24 h and 72 hr.

The z-VAD (100 μM) does not block the formation of vacuoles generated by BAPT-27 (10 μM) at 24 h and 72 hr (FIG. 36).

Figure 37:
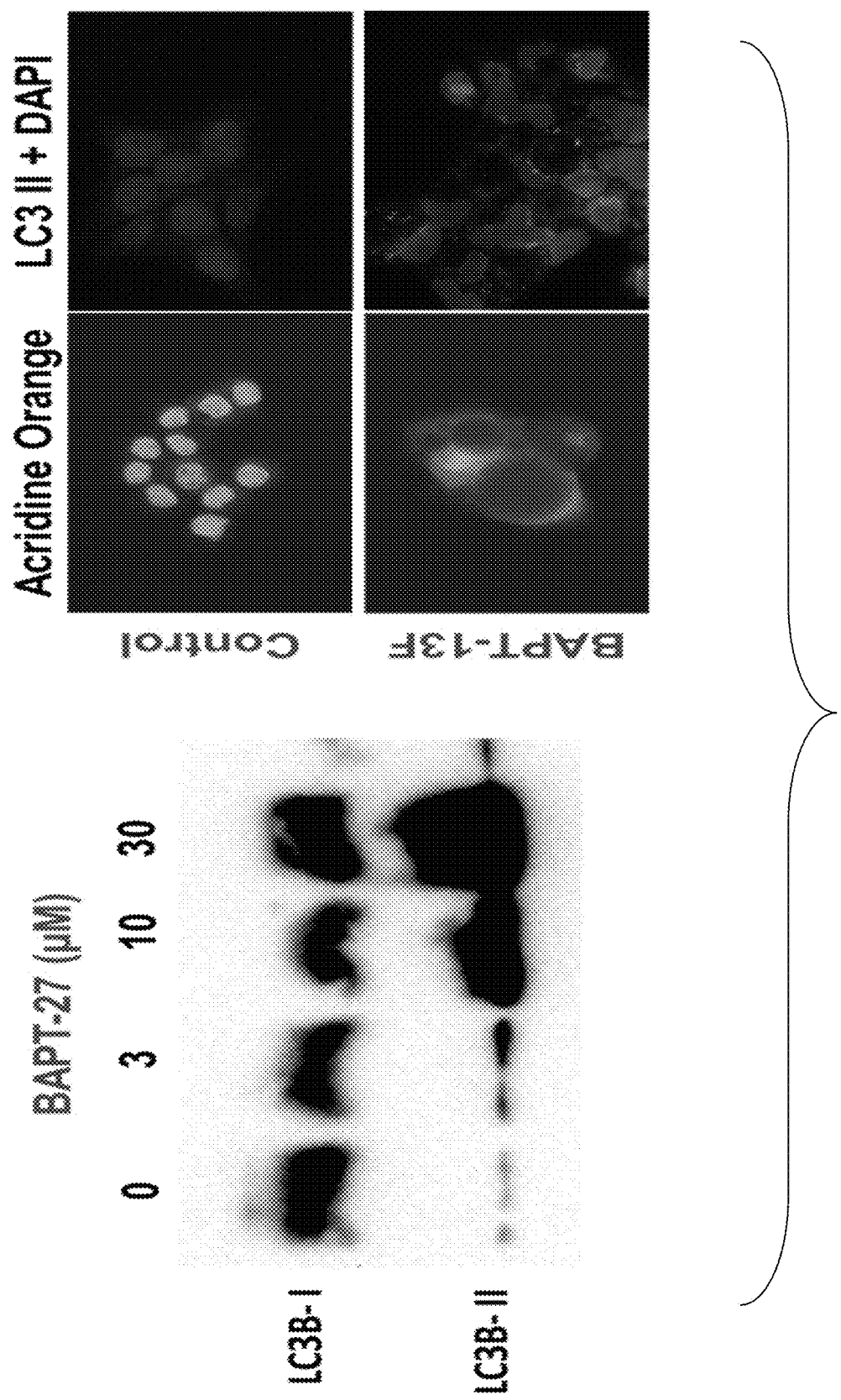
FIG. 37: Significant alteration in autophagic signaling resulting in the accumulation of autophagic markers such as LC3 II and acridine orange.

Without wishing to be bound by theory, it is believed that the mechanism by which BAPT-27 is produces its activities is due to alteration in key signaling pathways and several cellular events: (1) significant activation of macropinocytosis (FIGS. 32-33), and (2) significant alteration in autophagic signaling resulting in the accumulation of autophagic markers such as LC3 II and acridine orange (FIG. 37).

Figure 38:
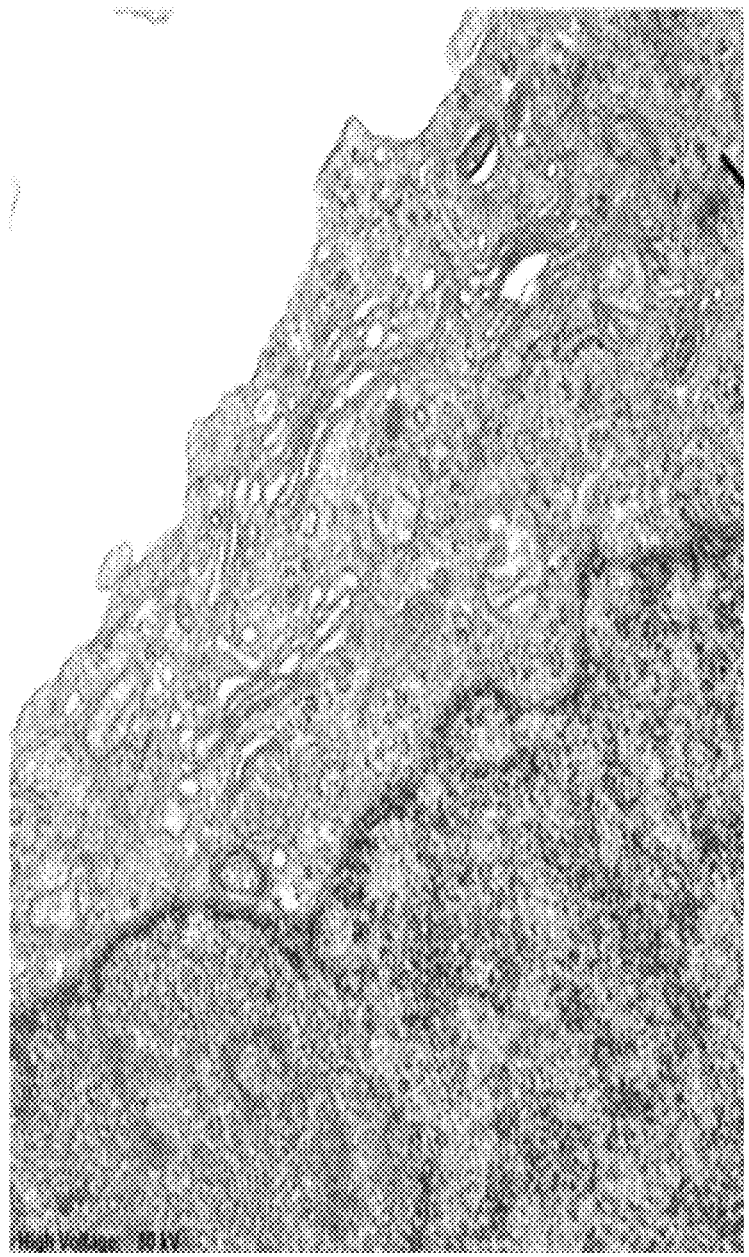
FIG. 38: Electron microscopy showing that endoplasmic reticulum (ER) is normal and not stressed even at the highest concentrations of BAPT-27 (100 μM). The ER is indicated by black arrows.
Figure 38:
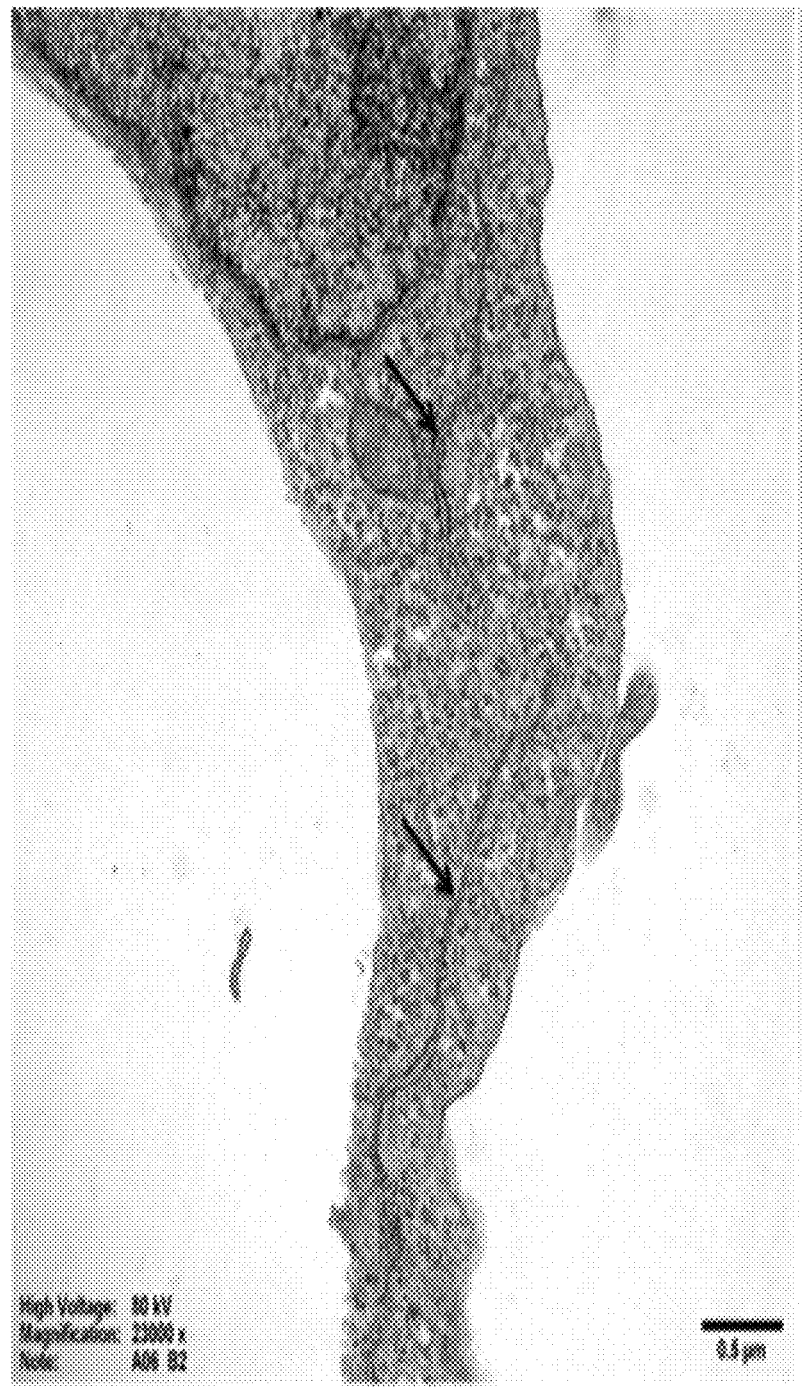
Figure 38:

Electron microscopy showed that endoplasmic reticulum (ER) is normal and not stressed even at the highest concentrations of BAPT-27 (100 μM). (FIG. 38). The ER is indicated by black arrows.

Figure 39:
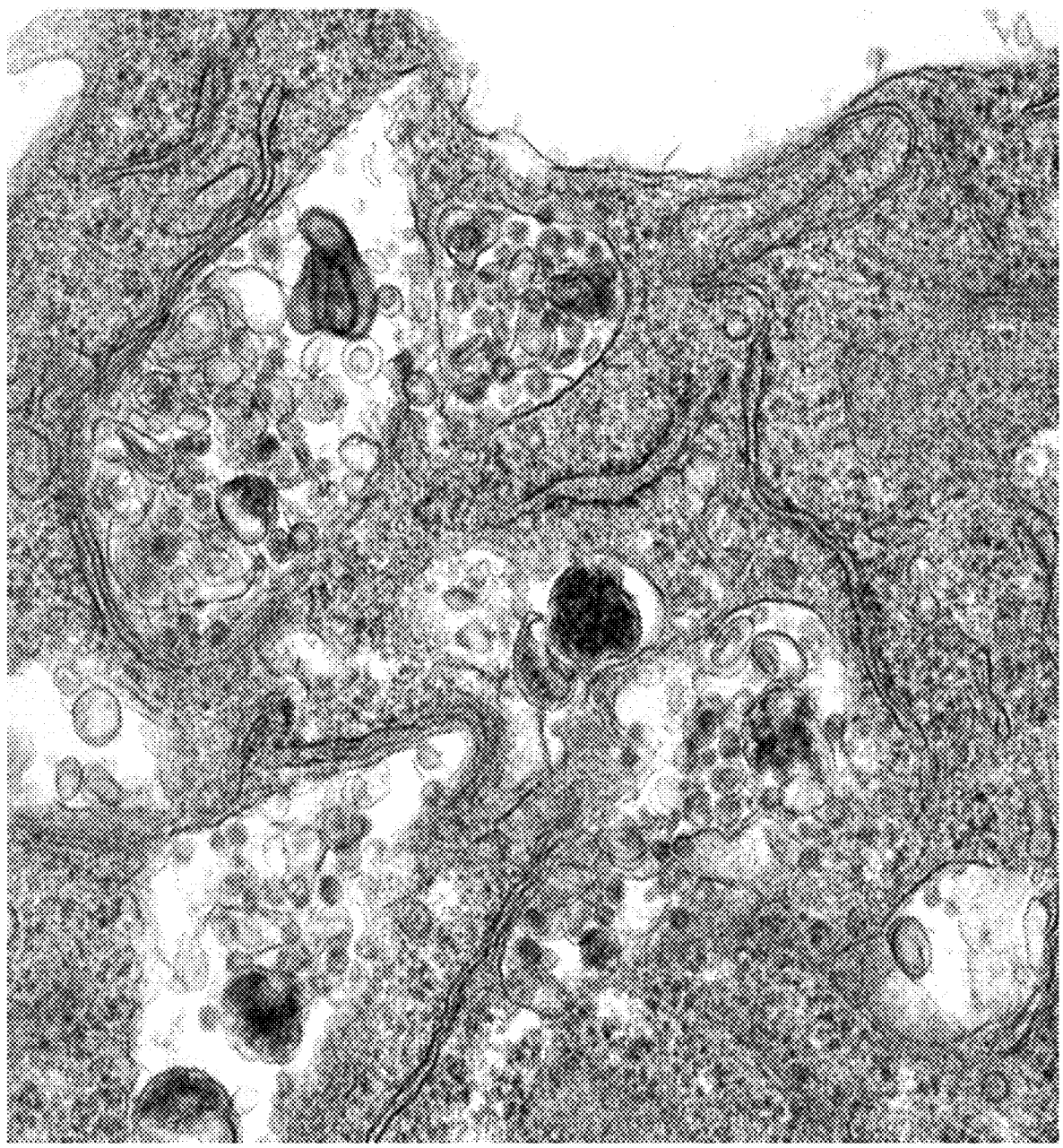
FIG. 39: Electron microscopy showing significant increase in the number of lysosomes, increased lysosomal activity, and increased size of lysosomes.

Electron microscopy showed a significant increase in the number of lysosomes, increased lysosomal activity, and increased size of lysosomes. (FIG. 39). This is an interesting phenomenon not observed previously. Increase in lysosomal activity is a goal of pro-drug formulations. This indicates that BAPT compounds can also be used as a delivery vehicles for pro-drugs.

Figure 40:
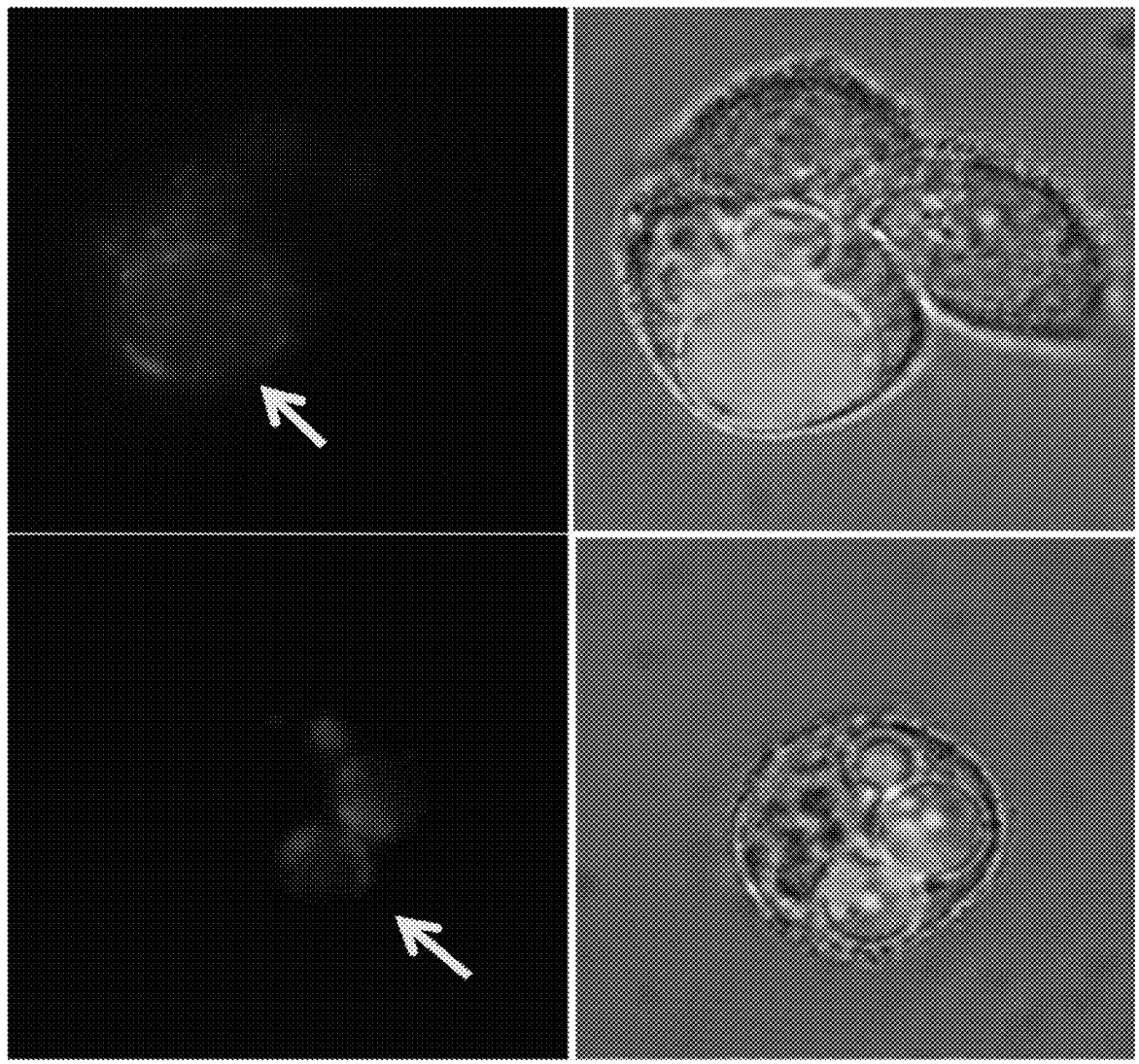
FIG. 40: BAPT-27 resulted in significant accumulation of the lysotracker red dye inside the formed vacuoles, indicating activation of lysosomes.

BAPT-27 resulted in significant accumulation of the lysotracker red dye inside the formed vacuoles, indicating activation of lysosomes. (FIG. 40).

Figure 41:
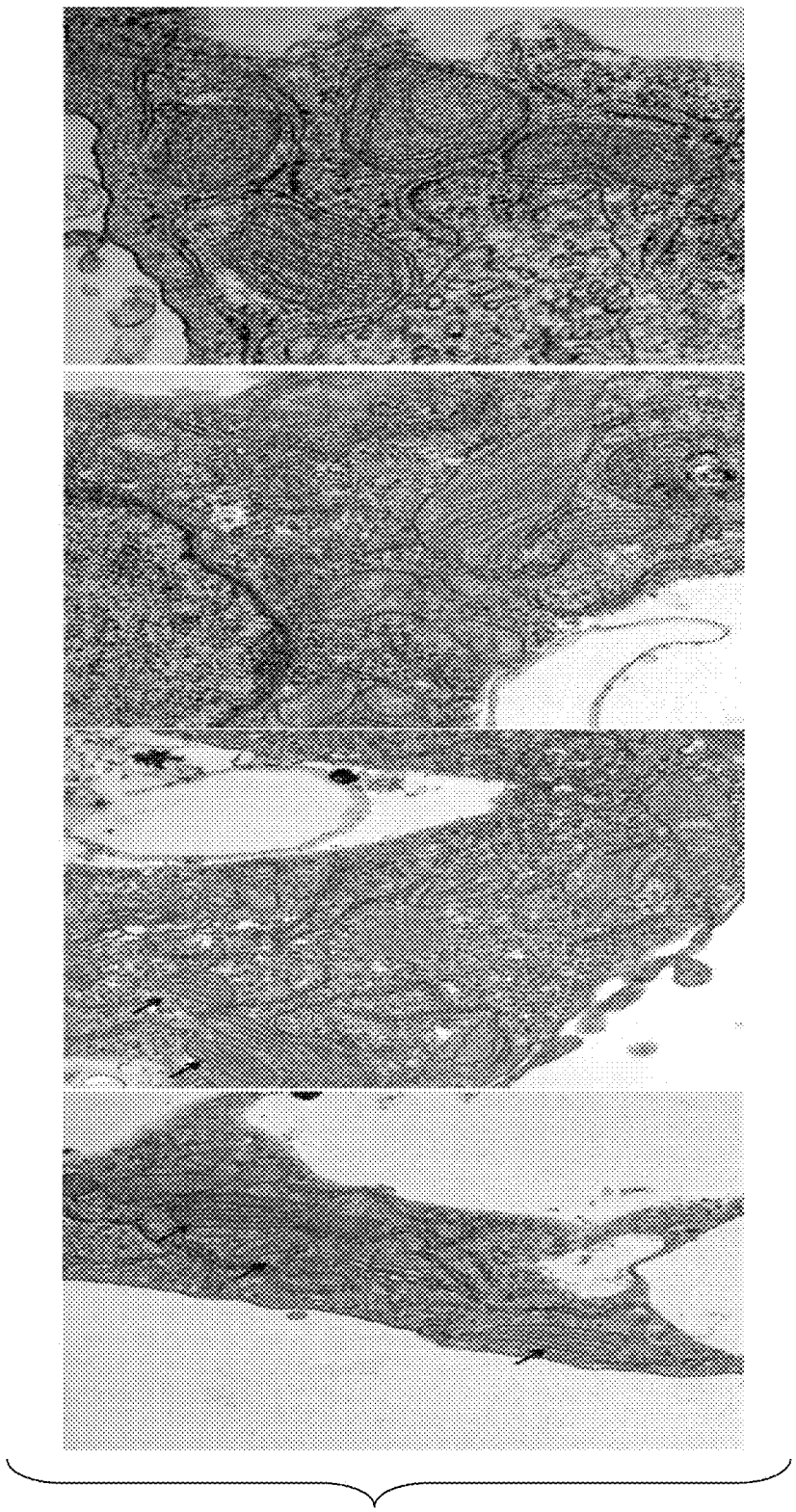
FIG. 41: Electron microscopy showing that at a very high concentration, in almost 50% of mitochondria, mitochondrial cisternae starts to dissolve with influx of fluid resulting in mitochondrial swelling (indicated by red arrow). Normal mitochondria are indicated by black arrows.

Electron microscopy showed that at a very high concentration, in almost 50% of mitochondria, mitochondrial cisternae starts to dissolve with influx of fluid resulting in mitochondrial swelling (indicated by red arrow in FIG. 41). Normal mitochondria are indicated by black arrows in FIG. 41.

Figure 42:
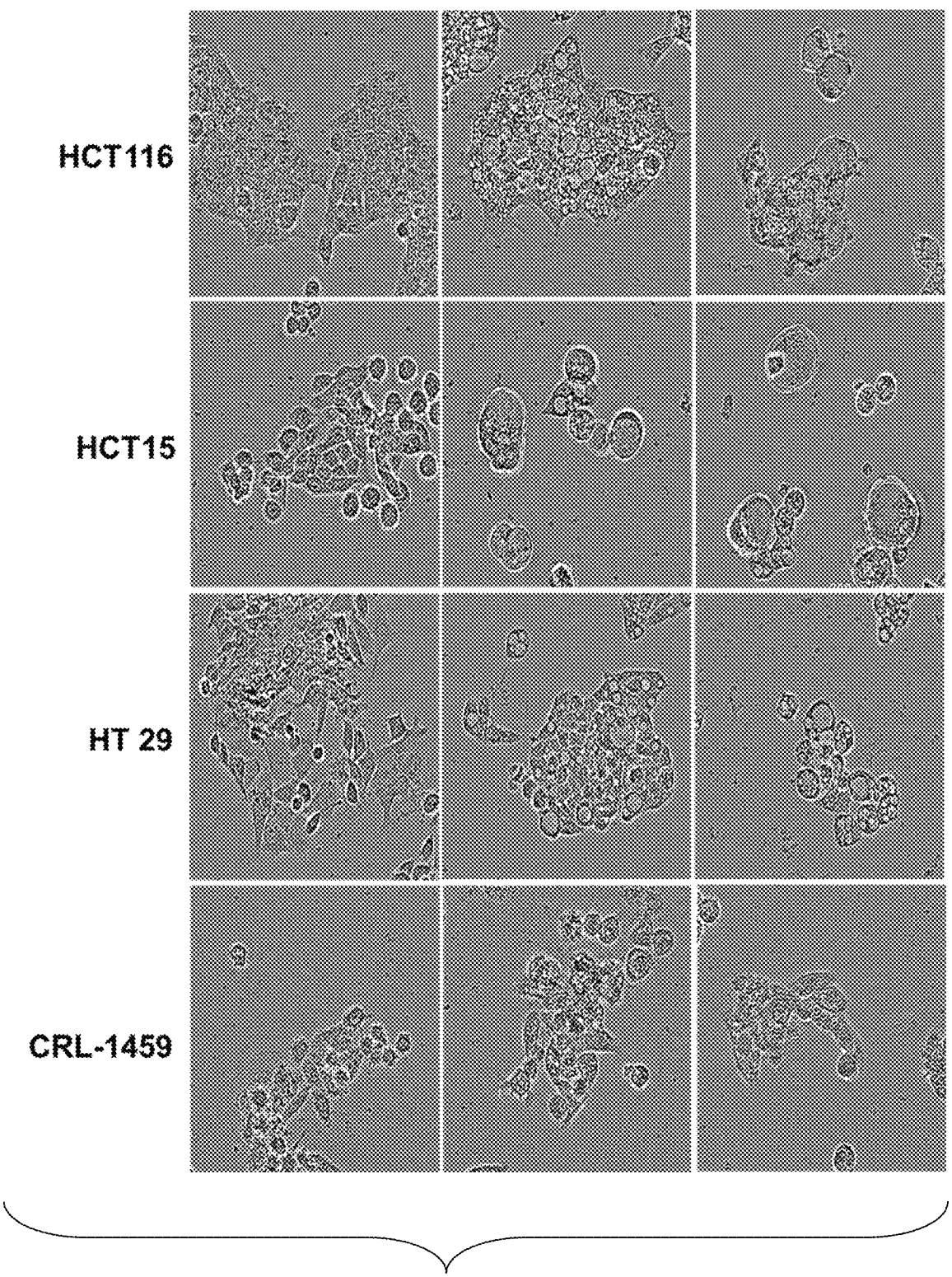
FIG. 42: The methuophagy inducing activities of BAPT-27 were prominent in the colon cancer cell lines HCT116, HCT15, and HT29, but vacuoles formation was not prominent in normal epithelial colon cells (CRL-1459).

The methuophagy inducing activities of BAPT-27 were also prominent in different colon cancer cell lines with different genetic profiles. BAPT-27 showed extensive vacuoles formation other in colon cancer cell lines (HCT116, HCT15, HT29). (FIG. 42). However, the vacuoles formation was not prominent in normal epithelial colon cells (CRL-1459). (FIG. 42).

Figure 43:
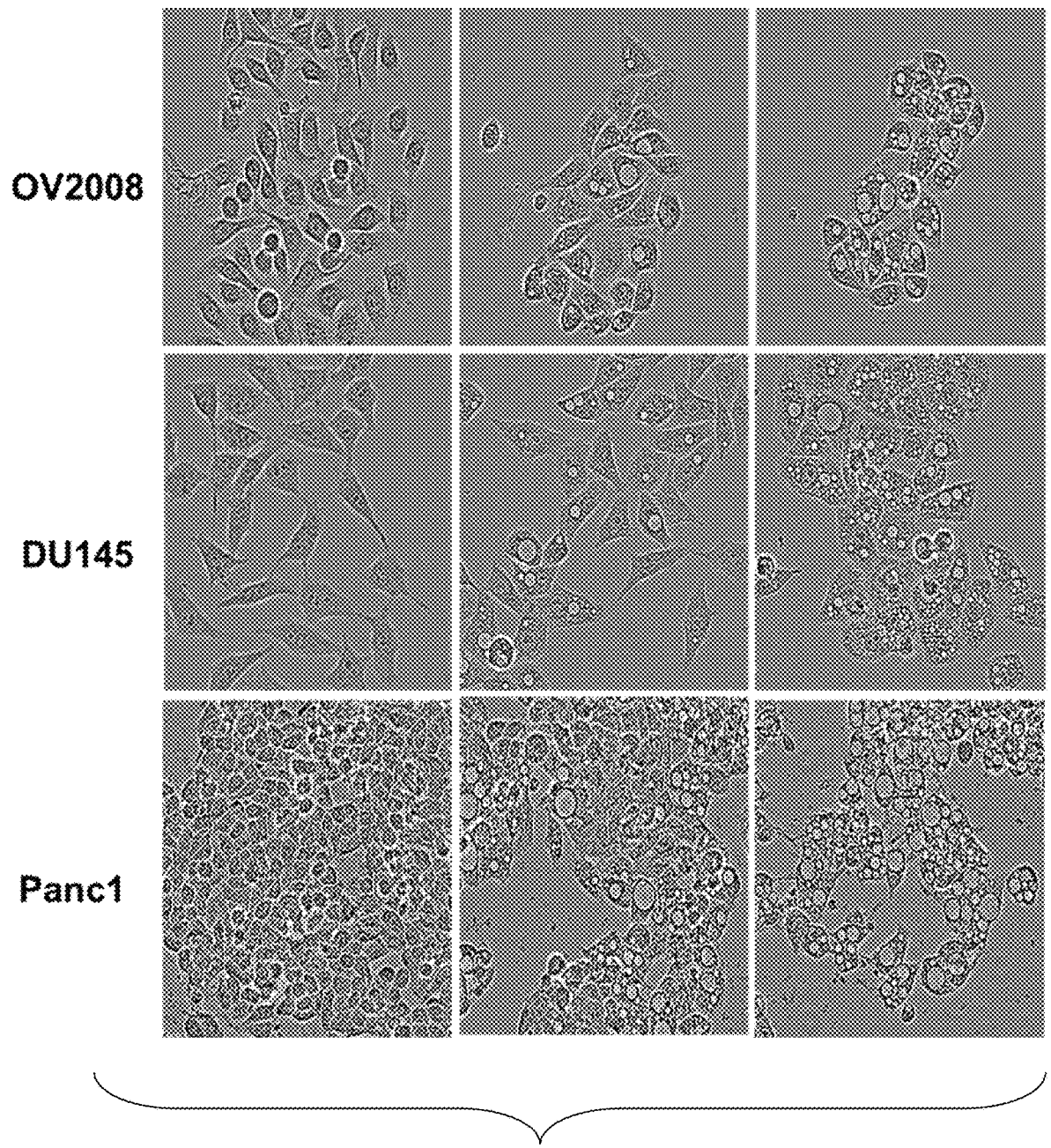
FIG. 43: The methuophagy was observed in ovarian cancer cell lines (OV2008), prostate cancer cell lines (DU-145), and a pancreatic cell line (Panc 1).

The methuophagy was also observed in ovarian cancer cell lines (OV2008), prostate cancer cell lines (DU-145), and a pancreatic cell line (Panc 1). (FIG. 43).

Figure 44:
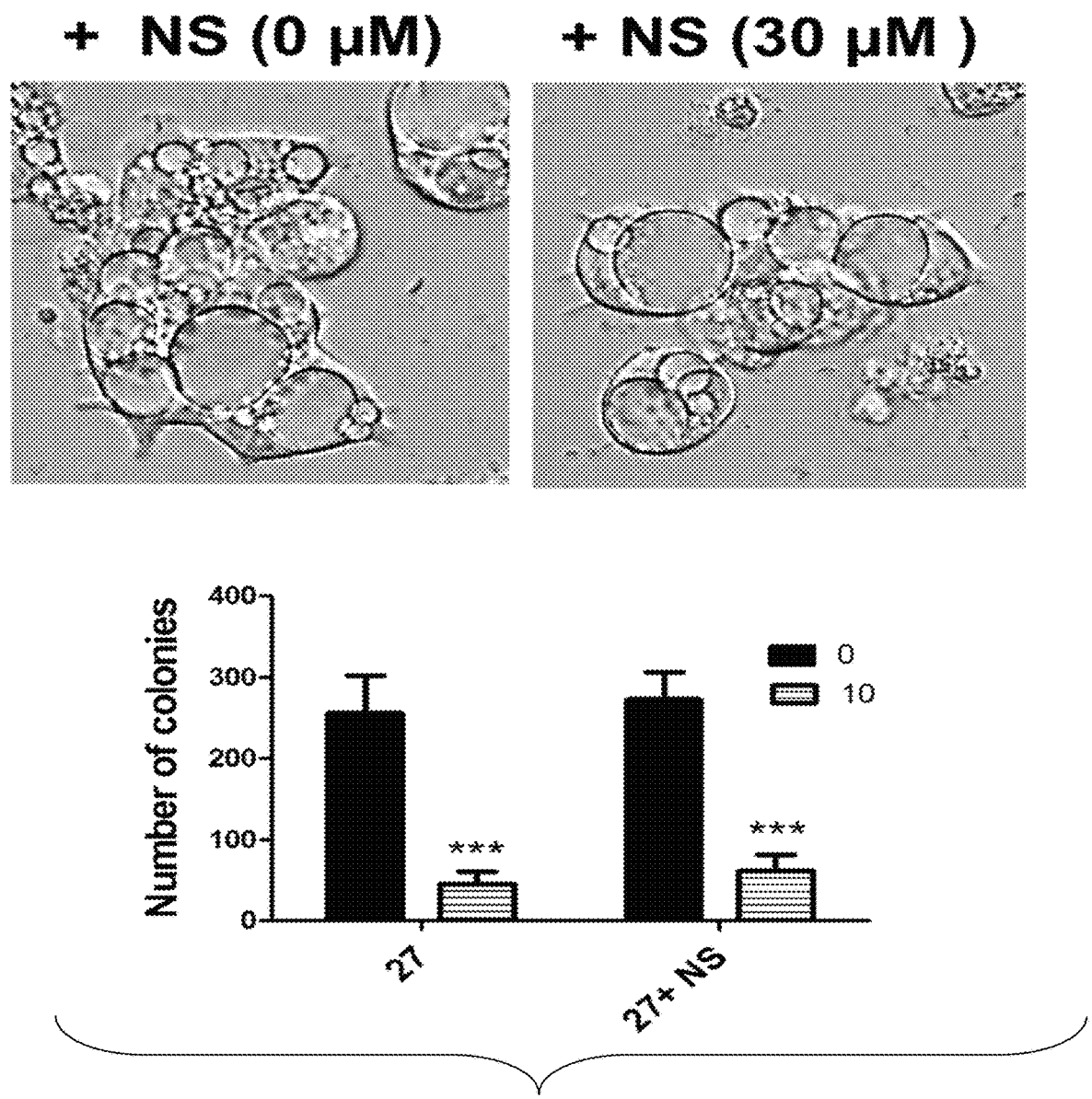
FIG. 44: Images and graph showing the vacuoles formation and cell death was not inhibited by the addition of necrostatin-1, a necroptosis inhibitor, even at high concentrations (up to 30 μM).

BAPT-27 induces a type of death that is independent of necrosis or necroptosis. The vacuoles formation and cell death was not inhibited by the addition of necrostatin-1, a necroptosis inhibitor, even at high concentrations (up to 30 μM). (FIG. 44).

Figure 45:
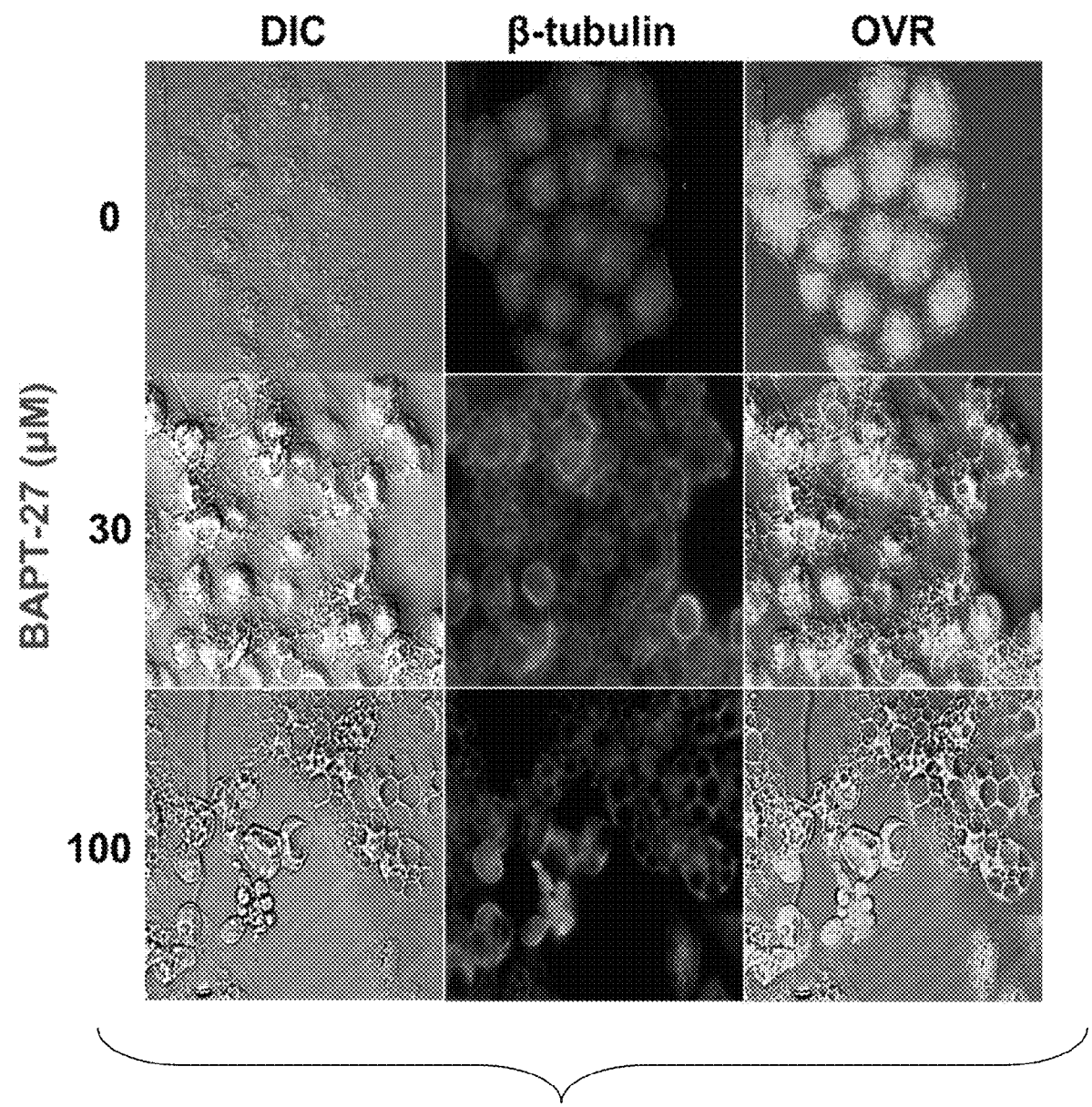
FIG. 45: Images showing BAPT-27 produced no significant change in β-tubulin expression levels at even up to 100 μM concentrations. BAPT-27 only induced significant disturbance in the microtubules dynamics at 24 h.

BAPT-27 produced no significant change in β-tubulin expression levels at even up to 100 μM concentrations. BAPT-27 only induced significant disturbance in the microtubules dynamics at 24 h. (FIG. 45).

Figure 46:
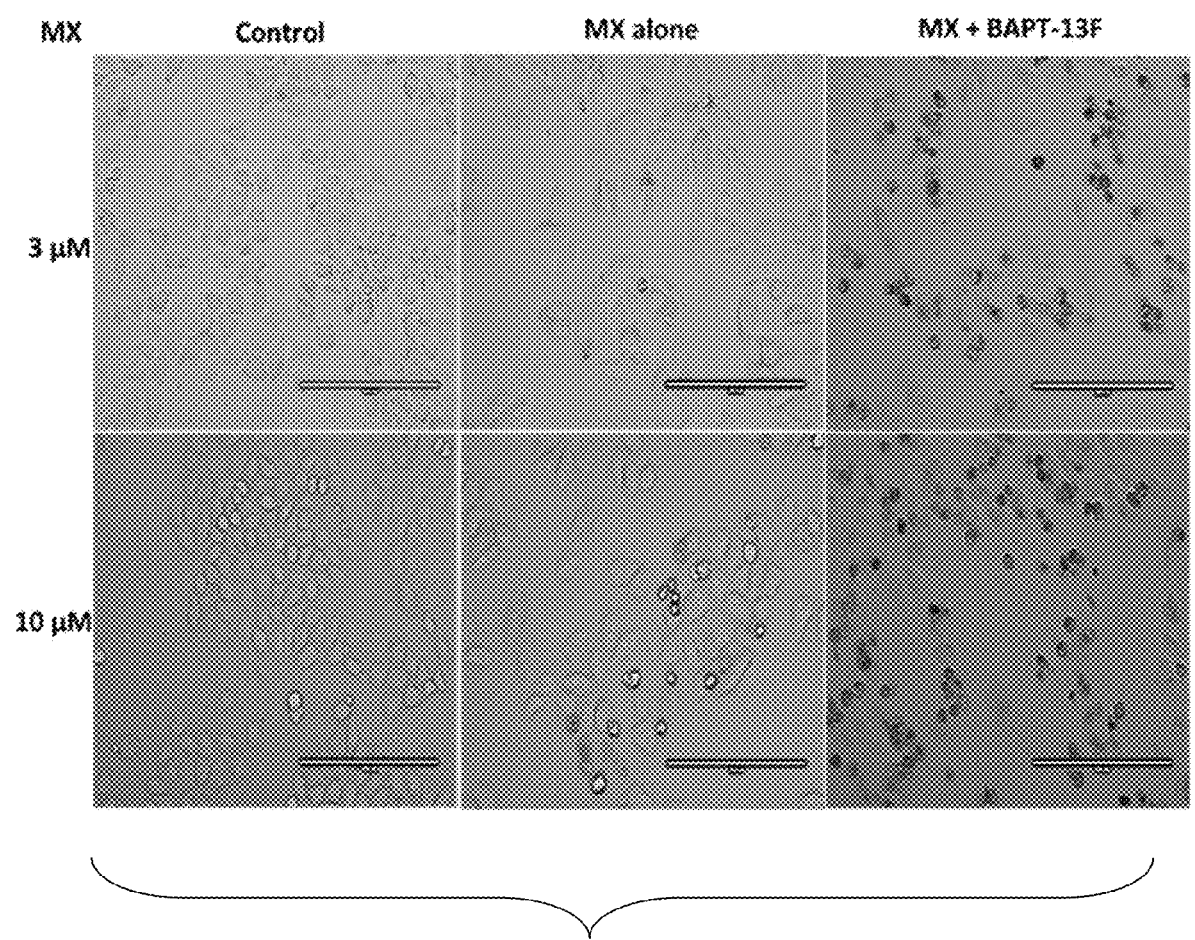
FIG. 46: Images showing the methuophagy inducing activities of BAPT-27 also extended to increase the delivery and enhanced sensitivity of anticancer agents doxorubicin and mitoxantrone in resistant cancer cell lines (H460-MX20), non-small cell lung cancer (NSCLC) cells resistant to mitoxantrone (MX) and doxorubicin (dox), and S1M180, colon cancer cells resistant to dox and MX. NSCLC cells resistant to apoptosis are also sensitive to the activities of BAPT-27.

The methuophagy inducing activities of BAPT-27 also extended to increase the delivery and enhanced sensitivity of anticancer agents doxorubicin and mitoxantrone in resistant cancer cell lines H460-MX20, non-small cell lung cancer (NSCLC) cells resistant to mitoxantrone (MX) and doxorubicin (dox), and S1M180, colon cancer cells resistant to dox and MX. (FIG. 46). NSCLC cells resistant to apoptosis are also sensitive to the activities of BAPT-27.

Figure 47:
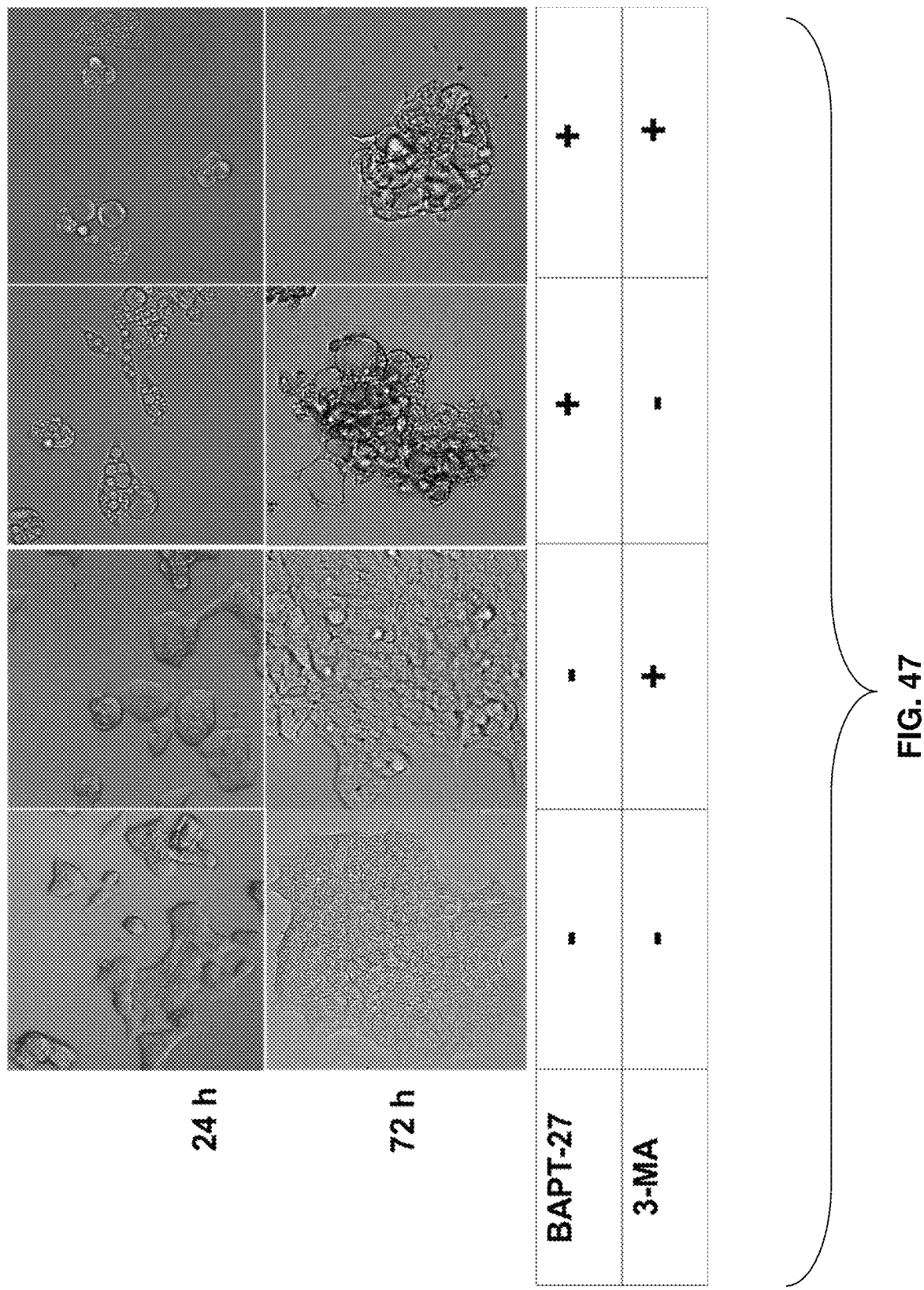
FIG. 47: Images showing that 3-methyl adenine (3-MA, 300 μM) does not block the formation of vacuoles generated by BAPT-27 (10 μM) at 24 h and 72 hr.

FIG. 47 shows that 3-methyl adenine (3-MA, 300 μM) does not block the formation of vacuoles generated by BAPT-27 (10 μM) at 24 h and 72 hr.

Figure 48:
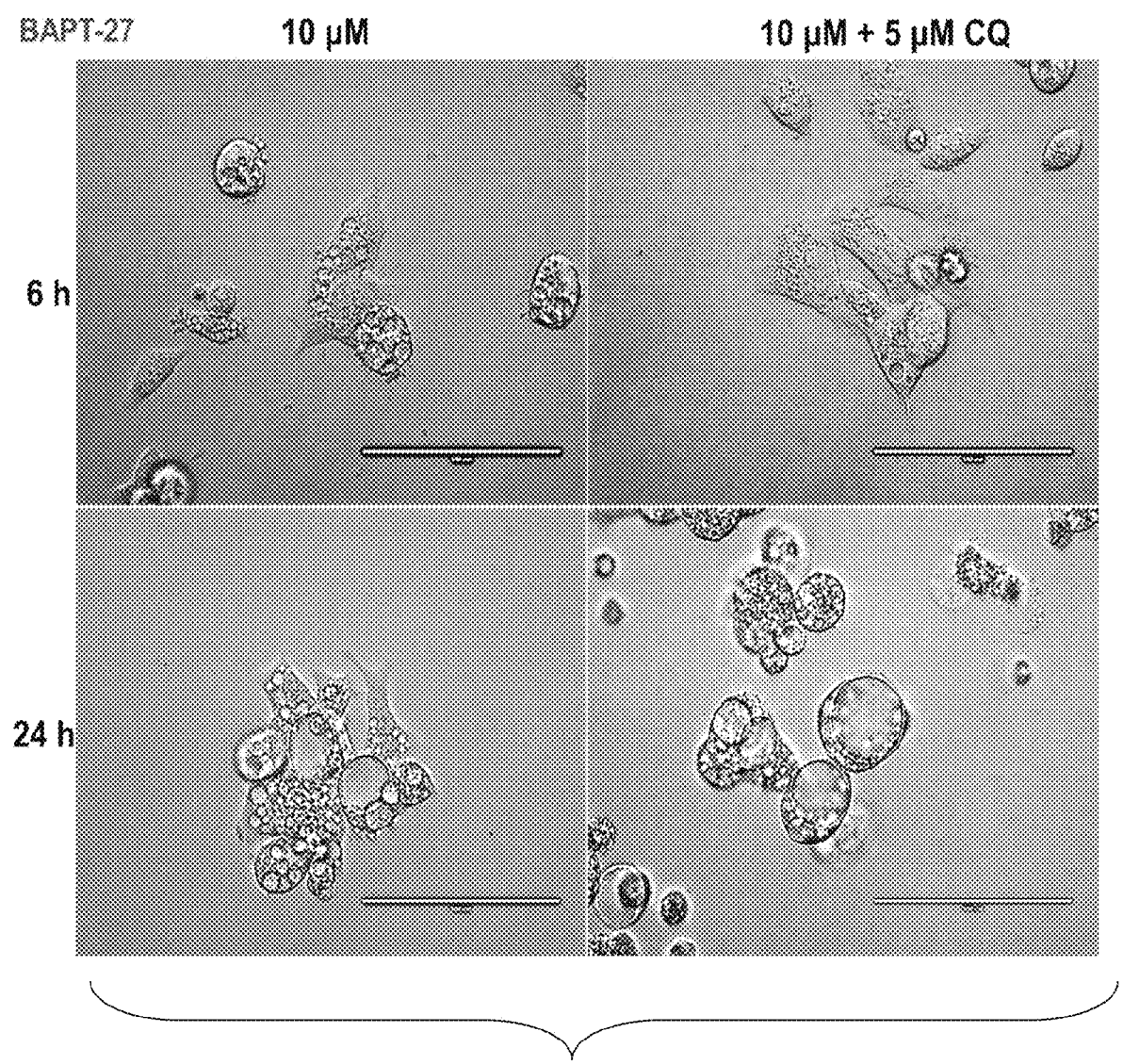
FIG. 48: Images showing that addition of 5 μM chloroquine (CQ) to BAPT-27 (10 μM) results in a delay of vacuoles formation, making them smaller, but does not prevent their formation. At 6 h treatment, the vacuoles were tiny and smaller in size in combination compared to BAPT-27 alone. However, at 24 h, chloroquine treatment could not prevent vacuoles regaining their normal size as those treated with BAPT-27 alone.

Addition of chloroquine (CQ) 5 μM to BAPT-27 (10 μM) results in a delay of vacuoles formation, making them smaller, but does not prevent their formation. At 6 h treatment, the vacuoles were tiny and smaller in size in combination compared to BAPT-27 alone. (FIG. 48). However, at 24 h, chloroquine treatment could not prevent vacuoles from regaining their normal size as those treated with BAPT-27 alone. (FIG. 48).

Figure 49A:
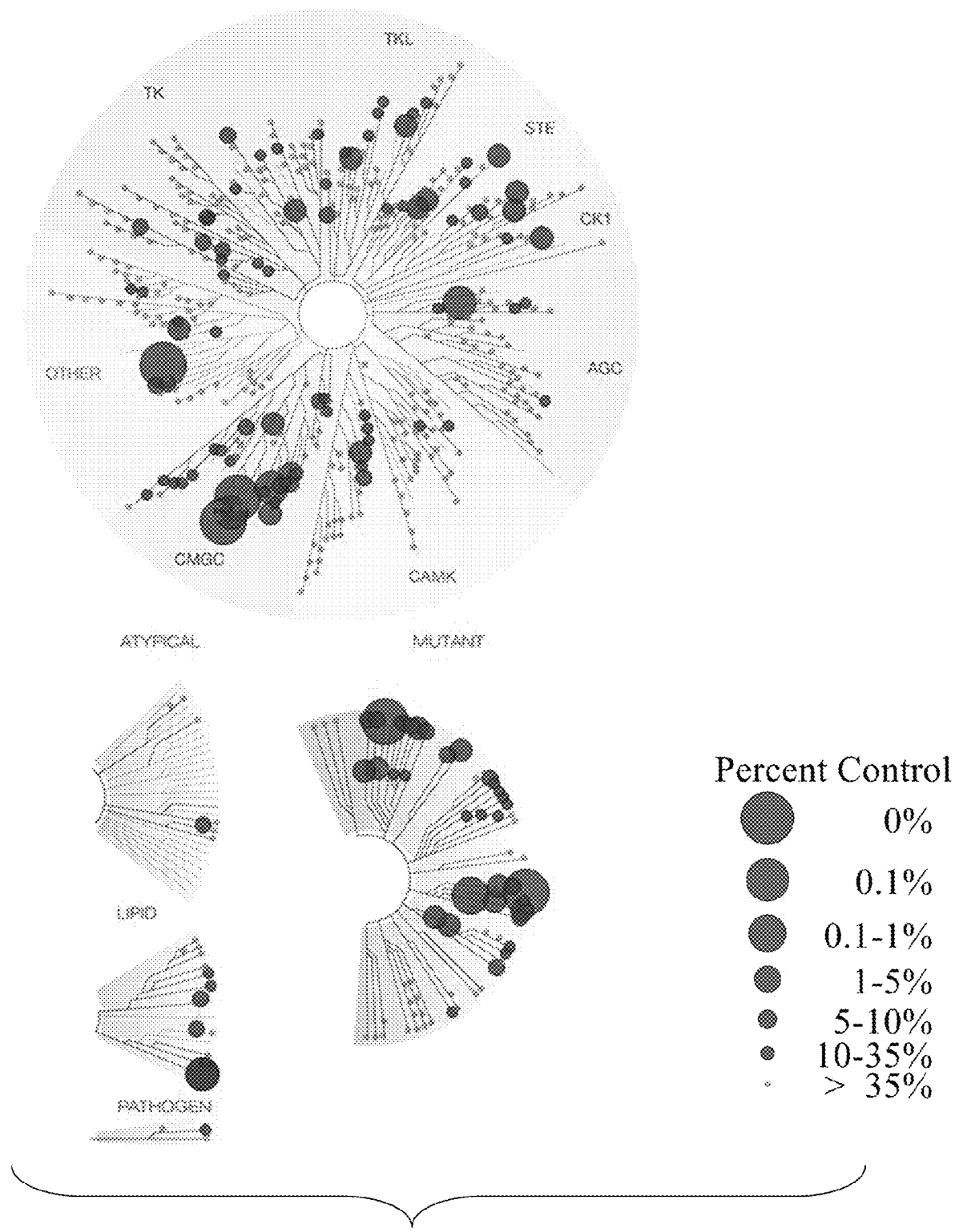
FIG. 49A: Image showing the effect of Image was generated using TREEspot™ Software Tool and reprinted with permission from KINOMEscan®, a division of DiscoveRx Corporation, © DISCOVERX CORPORATION 2010. Selectivity Score or S-score is a quantitative measure of compound selectivity. It was calculated by dividing the number of kinases that BAPT-27 bind to by the total number of distinct kinases tested, excluding mutant variants.
Figure 49B:
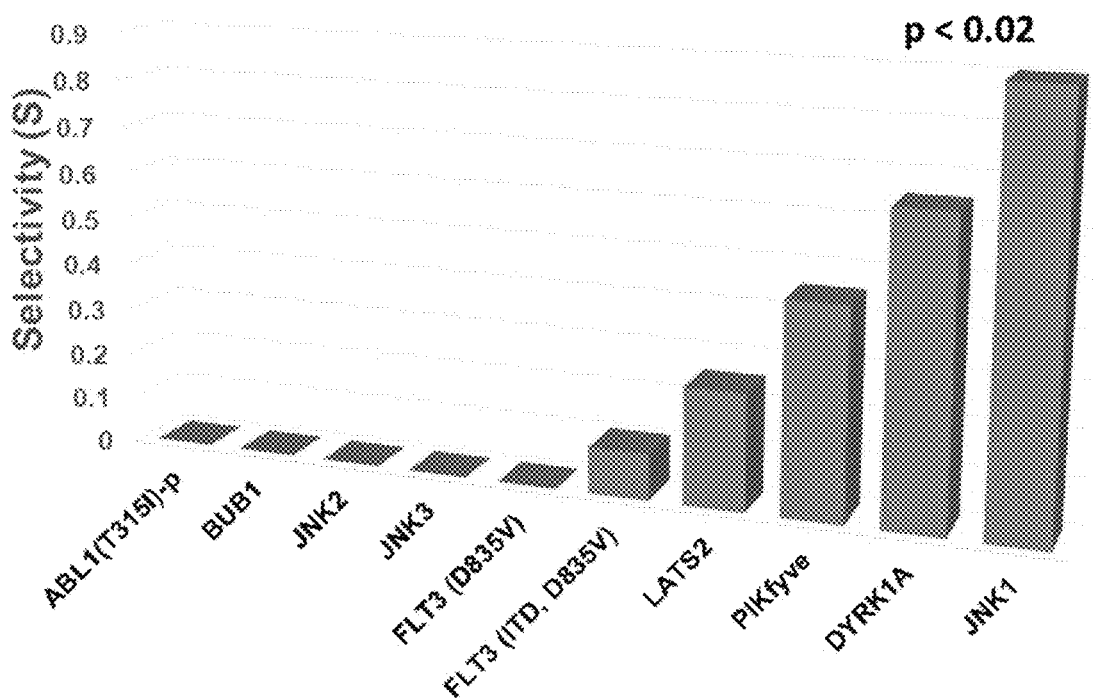
FIG. 49B: Image generated using TREEspot™ Software Tool and reprinted with permission from KINOMEscan®, a division of DiscoveRx Corporation, © DISCOVERX CORPORATION 2010. Selectivity Score or S-score is a quantitative measure of compound selectivity. It is calculated by dividing the number of kinases that BAPT-27 bind to by the total number of distinct kinases tested, excluding mutant variants.

Kinome screening (DiscoverX) of BAPT-27 against 468 kinases revealed that BAPT-27 shows inhibitory potency against phosphoinositide 5-kinase (PlKfyve) that regulates endosome-linked pathways (FIG. 49A & FIG. 49B.).

BAPT-27 also shows inhibitory potency against kinases implicated in cancer (JNK1, JNK2, JNK3, mutant kinase implicated in chronic myelogeneous leukemia (ABL1 T315I), fms-related tyrosine kinase 3 (FLT3(D835V) & FLT3(ITD, D835V)) and neurodegenerative diseases (DYRK1A) (FIG. 49A & FIG. 49B).

Figures 50A, 50B, 50C:
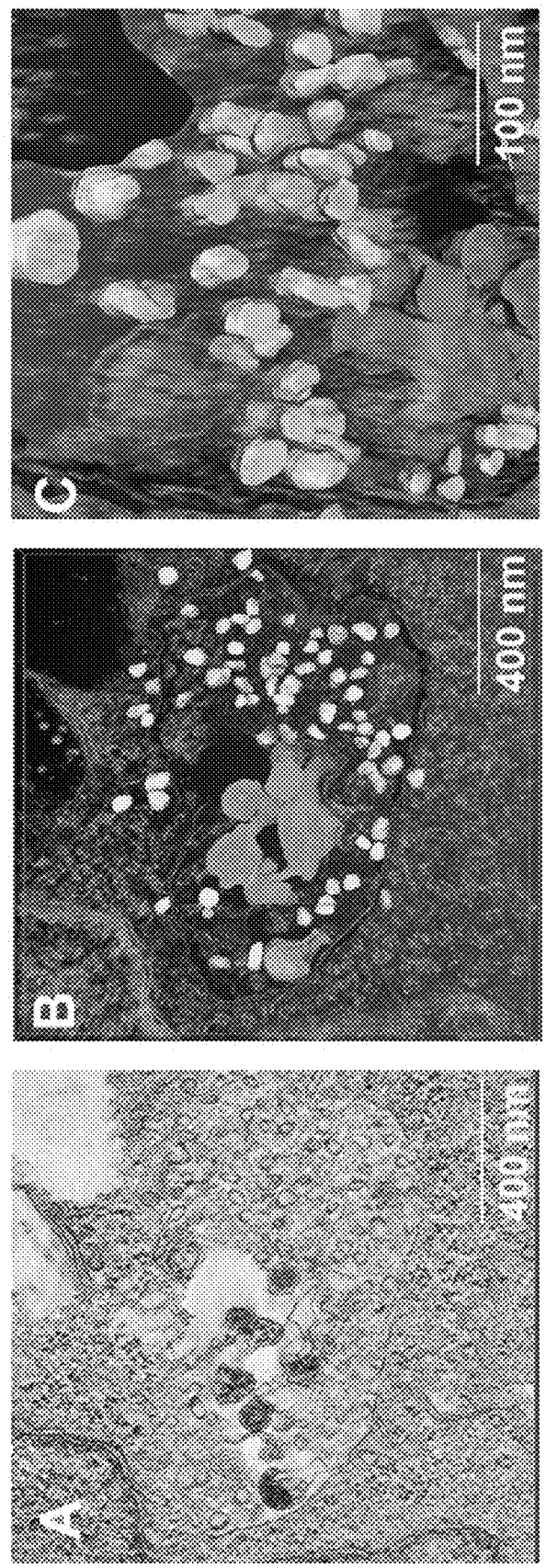
FIGS. 50A-50C: In HCT-116 cells, BAPT-27 produced significant increase in lysosomal size, as shown in FIGS. 50A-50C, using a 3D transmission electron tomographic image of a single vacuole, based on a tilt series Ceta Camera of FEI Talos L120C. The 3D reconstruction was loaded into the Avizo 3D Visualization software to reveal lysosomal structure through volume rendering and segmentation.

BAPT-27 produces significant increase in lysosomal size, as shown in FIGS. 50A-50C. FIGS. 50B-50C shows increased autophagic vesicles and increased lysosomal cargo suggesting that BAPT-27 may be blocking lysosomal clearance resulting in cell death. (FIG. 50A & FIG. 50B & FIG. 50C).

Figures 51A, 51B, 51C:
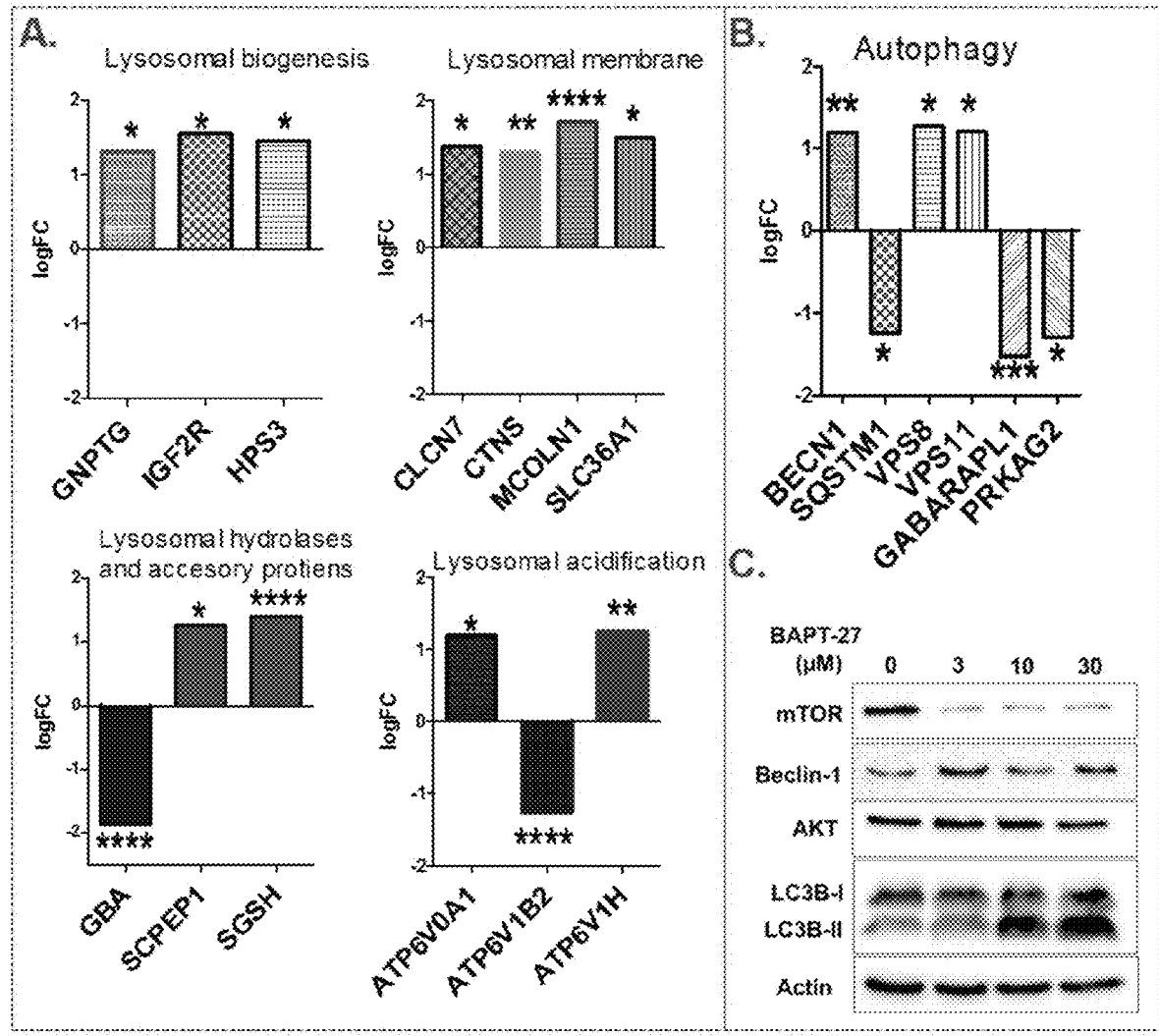
FIGS. 51A-C: Transcription factor EB (TFEB)—associated lysosomal and autophagy genes are upregulated in FIG. 51A and FIG. 51B as shown by RNA-seq analysis (Next-Seq500 with Illumina v2 chemistry) following the incubation of HCT-116 cells with BAPT-27 (10 μM, 6 h).

Autophagosome and lysosomal homeostasis is governed by transcription factor EB (TFEB)-mTOR signaling pathways (TFEB-mTOR pathway). Supporting FIGS. 50A-50C, it was seen that BAPT-27 significantly modulates lysosomal and autophagy associated genes (FIG. 51A-FIG. C). Further, BAPT-27 significantly downregulated mTOR and increased Beclin-1 and LC3B-II autophagy related markers indicating significant autophagy. (FIG. 51A & FIG. 51B & FIG. 51C).

Figure 52:
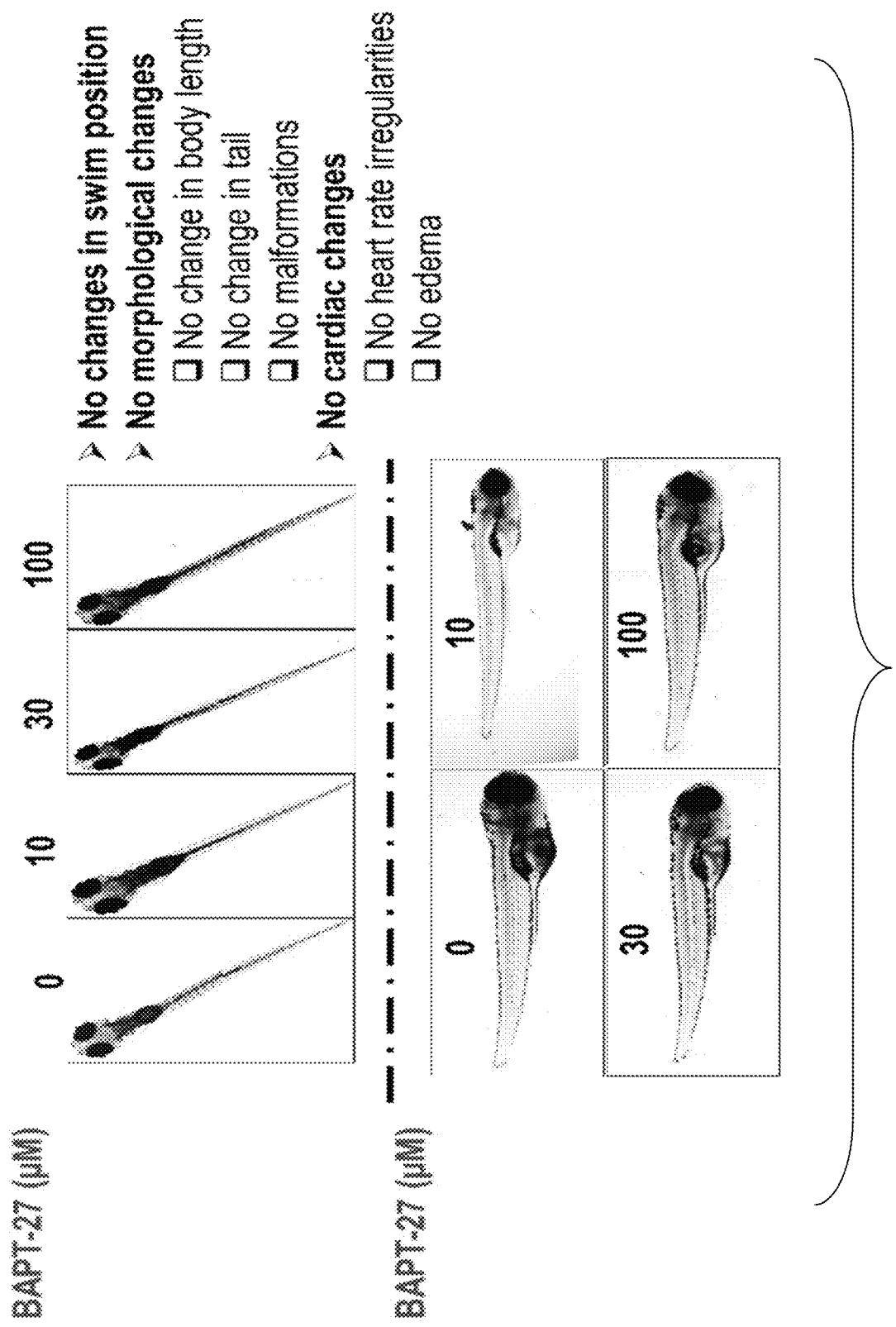
FIG. 52: BAPT-27 is safe in zebrafish even at a very high concentration of 100 μM. The fish were healthy with no changes in their morphology, swim positions, or their cardiac parameters.

The safety of BAPT-27 was studied in zebrafish. BAPT-27 is safe in zebrafish even at a very high concentration of 100 μM. The fish were healthy with no changes in their morphology, swim positions, or their cardiac parameters. (FIG. 52).

Figure 53A:
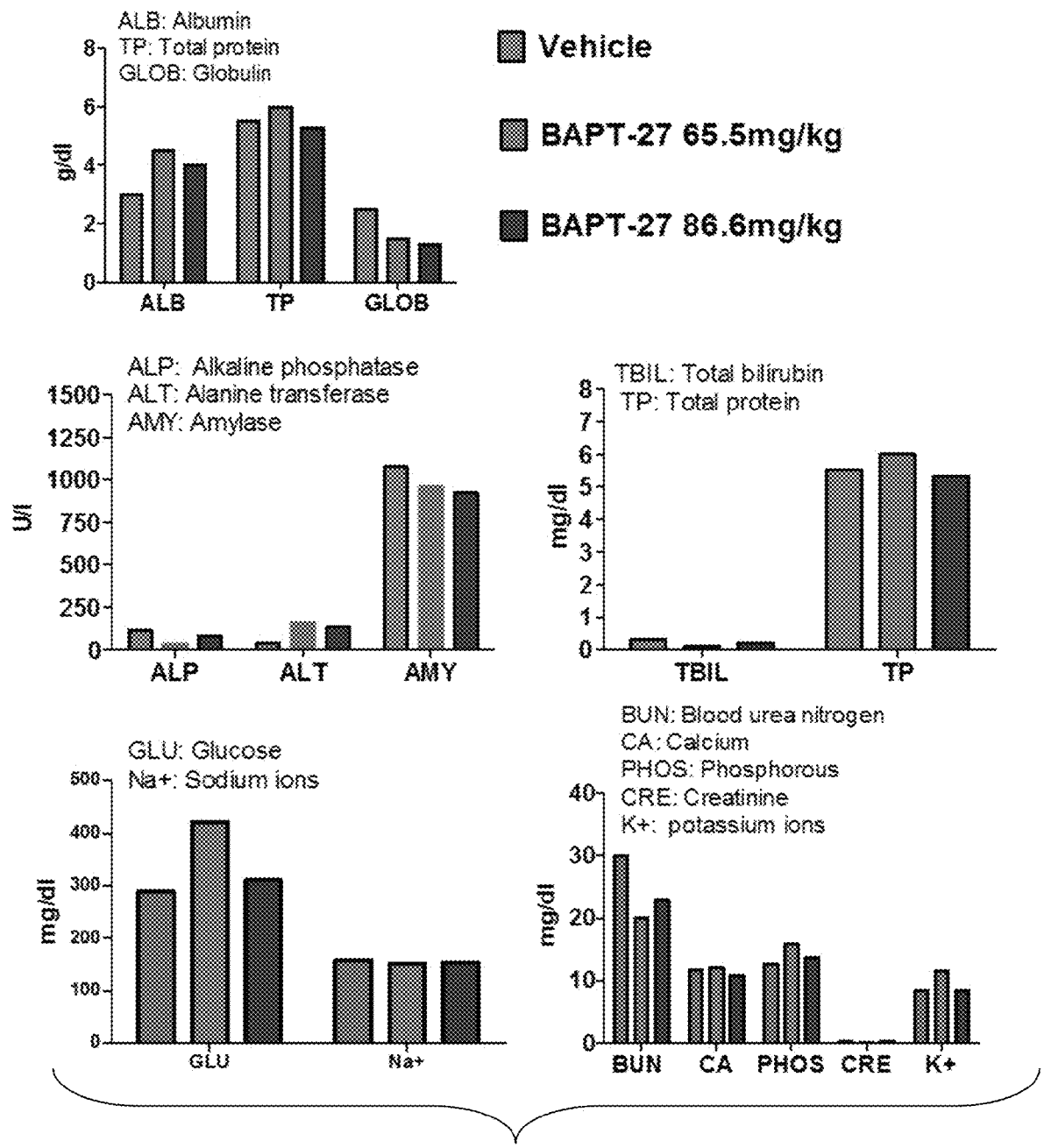
FIG. 53A: C57BL/6J mice (8-10 weeks old) were treated intraperitoneally with indicated concentration of BAPT-27 or vehicle (saline) for 14 days. At the end of 14 days, blood was collected in heparin-coated tubes for blood chemistry analysis using abaxis veterinary chemistry analyzer (VETS-CAN vs2). No behavioral or phenotypic toxicity was noted at the highest dose tested.
Figure 53B:
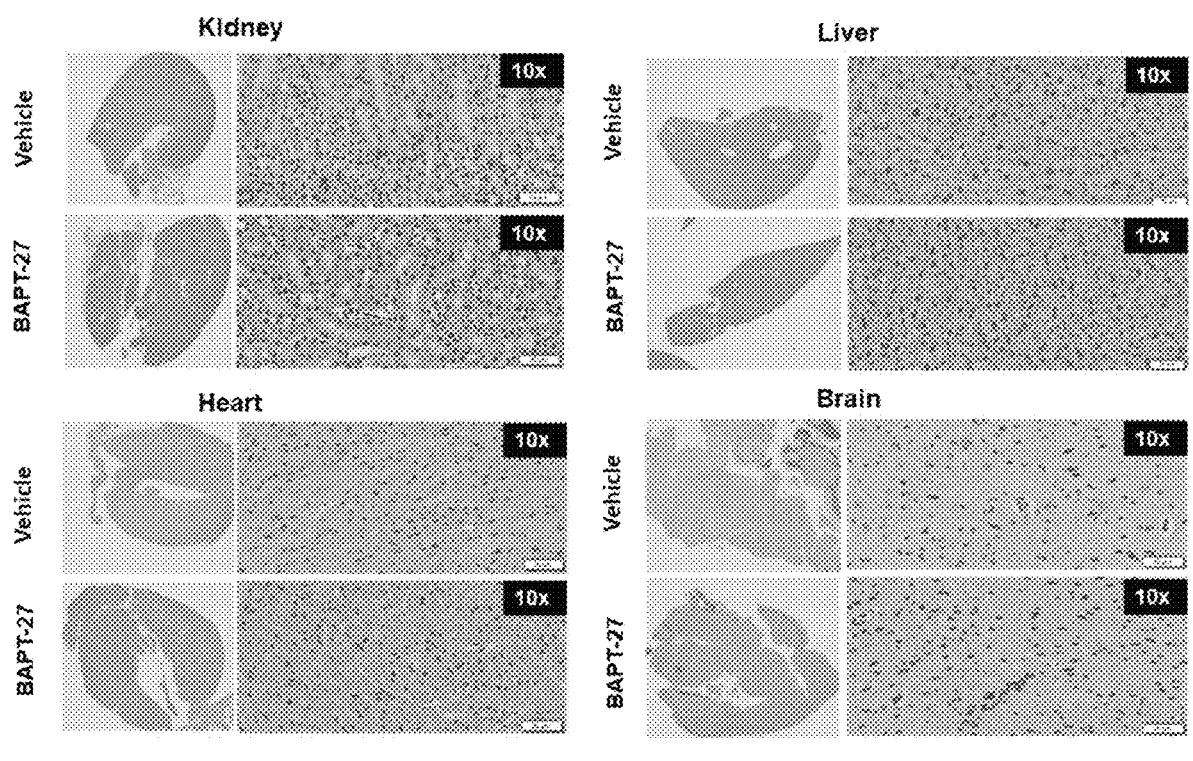
FIG. 53B: Representative immunohistochemical slides are shown for kidney, liver, heart and brain for C57BL/6mice treated intraperitoneally with vehicle (saline) or BAPT-27 at 86.6 mg/kg. The whole tissue section and 10× magnification slides are shown.

Safety studies done in in C57BL/6, (6-8 week old) wild type mice indicated that BAPT-27 is safe even at high doses (86.6 mg/kg given intraperitoneally) (FIG. 53A & FIG. 53B.). In addition, no behavioral or phenotypic toxicity was observed in BAPT-27 treated mice for up to 14 days.

Table 1 in FIG. 54 shows treatment of different BAPT compounds on HCT-116 (colon cancer), BT-20 (triple negative breast cancer) and U-251 (glioblastoma) cancer cell lines at 72 h. Formation of small or large vacuoles by different BAPT compounds leading to dell death at different concentrations, were observed and recorded. Vac or V; Vacuoles.

Table 2 in FIG. 55 shows treatment of different BAPT compounds on HCT-116 (colon cancer), BT-20 (triple negative breast cancer) and U-251 (glioblastoma) cancer cell lines at 72 h. Formation of small or large vacuoles by different BAPT compounds leading to dell death at different concentrations, were observed and recorded. Vac or V; Vacuoles.

Certain embodiments of the compounds, compositions, and methods disclosed herein are defined in the above examples. It should be understood that these examples, while indicating particular embodiments of the invention, are given by way of illustration only. From the above discussion and these examples, one skilled in the art can ascertain the essential characteristics of this disclosure, and without departing from the spirit and scope thereof, can make various changes and modifications to adapt the compositions and methods described herein to various usages and conditions. Various changes may be made and equivalents may be substituted for elements thereof without departing from the essential scope of the disclosure. In addition, many modifications may be made to adapt a particular situation or material to the teachings of the disclosure without departing from the essential scope thereof.

What is claimed is:

1. A compound comprising BAPT-54:

BAPT-54

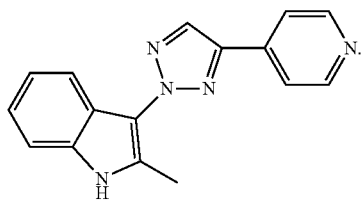

2. A pharmaceutical composition comprising:
   a therapeutically effective amount of a compound of claim 1; and
   a pharmaceutically acceptable carrier, adjuvant, or diluent.

3. The pharmaceutical composition of claim 2, further comprising an anticancer agent which induces cancer cell death by an apoptotic process.

4. A method of inducing cell death in a cancer cell, sensitizing a resistant cancer cell to cytotoxicity, inhibiting cell growth inhibiting cell growth, treating or ameliorating a cancer, or activating lysosomes in a cell,
   the method comprising
   administering an effective amount of the compound of claim 1 to a cancer cell and inducing death of the cancer cell by methuosis, autophagy, or a combination of methuosis and autophagy.

5. The method of claim 4, wherein the cancer cell is missing a pro-apoptotic gene comprising Bax, Bak, or both Bax and Bak.

6. The method of claim 4, wherein the compound induces rapid accumulation of extensive fluid filled cytoplasmic vacuoles in the cancer cell.

7. The method of claim 4, further comprising administering an apoptosis and non-apoptosis-inducing agent to the cancer cell.

8. The method of claim 4, wherein the cancer is resistant to mitoxantrone and/or doxorubicin.

9. The method of claim 4, wherein the cancer cell is refractory to death by apoptosis-inducing anticancer agents.

10. The method of claim 4, wherein the cancer is colon cancer, lung cancer, ovarian cancer, prostate cancer, breast cancer, brain cancer or pancreatic cancer.

11. The method of claim 4, wherein sensitizing a resistant cancer cell to cytotoxicity comprises:
    administering to a resistant cancer cell a combination therapy and sensitizing the resistant cancer cell to cytotoxicity,
    wherein the combination therapy comprises an antineoplastic agent in combination with the compound BAPT-54.

12. The method of claim 11, wherein the antineoplastic agent comprises mitoxantrone.

13. The method of claim 11, wherein the cancer is colon cancer or lung cancer.

* * * * *